(12) United States Patent
Draper et al.

(10) Patent No.: US 10,124,048 B2
(45) Date of Patent: Nov. 13, 2018

(54) ADENOVIRUS VECTORS

(71) Applicant: ISIS INNOVATIONS LIMITED, Oxford (GB)

(72) Inventors: Simon Draper, Oxford (GB); Arturo Reyes, Oxford (GB); Saranya Sridhar, Oxford (GB); Adrian Hill, Oxford (GB); Sarah Gilbert, Oxford (GB); Anna Goodman, Oxford (GB)

(73) Assignee: Oxford University Innovation Limited, Oxford (GB)

( * ) Notice: Subject to any disclaimer, the term of this patent is extended or adjusted under 35 U.S.C. 154(b) by 0 days.

(21) Appl. No.: 14/697,373

(22) Filed: Apr. 27, 2015

(65) Prior Publication Data

US 2015/0297700 A1    Oct. 22, 2015

Related U.S. Application Data

(63) Continuation of application No. 12/595,574, filed as application No. PCT/GB2008/001262 on Apr. 10, 2008, now Pat. No. 9,017,696.

(30) Foreign Application Priority Data

Apr. 10, 2007    (GB) .................................... 0706914.9

(51) Int. Cl.
| | | |
|---|---|---|
| A61K 39/00 | (2006.01) |
| A61K 39/39 | (2006.01) |
| C07K 16/20 | (2006.01) |
| C07K 14/445 | (2006.01) |
| A61K 39/015 | (2006.01) |
| C12N 15/861 | (2006.01) |
| C12N 15/86 | (2006.01) |
| C07K 14/78 | (2006.01) |

(52) U.S. Cl.
CPC ............ A61K 39/015 (2013.01); A61K 39/39 (2013.01); C07K 14/445 (2013.01); C07K 14/78 (2013.01); C07K 16/205 (2013.01); C12N 15/86 (2013.01); A01K 2227/105 (2013.01); A01K 2267/0337 (2013.01); A61K 2039/5256 (2013.01); A61K 2039/545 (2013.01); A61K 2039/55561 (2013.01); C12N 2710/10334 (2013.01); C12N 2710/10343 (2013.01); Y02A 50/412 (2018.01); Y10S 435/975 (2013.01)

(58) Field of Classification Search
None
See application file for complete search history.

(56) References Cited

U.S. PATENT DOCUMENTS

2005/0009118 A1    1/2005    Zhang
2009/0285852 A1    11/2009    Rybicki

FOREIGN PATENT DOCUMENTS

| WO | 1996/18616 | 6/1996 |
|---|---|---|
| WO | 2001/02607 | 1/2001 |
| WO | 2001/21201 | 3/2001 |
| WO | 2002/04493 | 1/2002 |
| WO | 2004/082605 | 9/2004 |
| WO | 20051071093 | 8/2005 |
| WO | 2006/029153 | 3/2006 |
| WO | 2006/031675 | 3/2006 |
| WO | 2007/027860 | 3/2007 |
| WO | 2007/100584 | 9/2007 |
| WO | 2008/020902 | 2/2008 |
| WO | 2008-112159 | 9/2008 |

OTHER PUBLICATIONS

Kerry et al. J. Virol. 69: 3868-3872, 1992.*
Boshart et al. Cell 41: 521-530, 1985.*
Facciabene, Andrea, et al. "Vectors encoding carcinoembryonic antigen fused to the B subunit of heat-labile enterotoxin elicit antigen-specific immune responses and antitumor effects" Vaccine, vol. 26(1), Nov. 20, 2007, 47-58.
Gilbert, Sarah C., et al. "Enhanced CD8 T cell immunogenicity and protective efficacy in a mouse malaria model using a recombinant adenoviral vaccine in heterologous prime-boost immunisation regimes" Vaccine, vol. 20(7-8), Jan. 15, 2002, 1039-1045.
Shiver, John W., et al. "Replication-incompetent adenoviral vaccine vector elicits effective anti-immunodeficiency virus immunity" Nature, vol. 415, 2002, 331-335.
Wang, Jun, et al. "Single mucosa!, but not parenteral, immunization with recombinant adenoviral-based vaccine provides potent protection from pulmonary tuberculosis" Journal of Immunology, vol. 173(10), Nov. 15, 2004, 6357-6365.
Gilbert, Sarah C., et al. "Synergistic DNA-MVA prime-boost vaccination regimes for malaria and tuberculosis" Vaccine, vol. 24 (21) May 22, 2006, 4554-4561.
Kobinger, Gary P., et al. "Simian adenoviral vector based-vaccine fully protect against ebola virus even in the presence of pre-existing immunity to human adenovirus" Molecular Therapy, vol. 9(1) May 2004, p. 142 [Abstract].
Fitzgerald, Julie C., et al. "A simian replication-defective adenoviral recombinant vaccine to HIV-1 Gag" The Journal of Immmunology, vol. 170, Feb. 2003, 1416-1422.
Pinto, A.R., et al. "Induction of CD8+ T cells to an HIV-1 antigen upon oral immunization of mice with a simian E1-deleted adenoviral vector" Vaccine, vol. 22(5-6), 2004, 697-703.

(Continued)

*Primary Examiner* — Sarvamangala Devi

(74) *Attorney, Agent, or Firm* — Kathleen D. Rigaut; Dann, Dorfman, Herrell and Skillman, P.C.

(57) ABSTRACT

An adenoviral vector comprising a promoter further comprising a fragment of the 5' untranslated region of the CMV IE1 gene including intron A and a nucleic acid sequence encoding a pathogen or tumor antigen for use as a medicament.

7 Claims, 16 Drawing Sheets

Specification includes a Sequence Listing.

(56) References Cited

OTHER PUBLICATIONS

McConkey, Samuel J., et al. "Enhanced T-cell immunogenicity of plasmid DNA vaccines boosted by recombinant modified vaccinia virus Ankara in humans" Nature Medicine, vol. 9(6), Jun. 2003, 729-735.

Schneider, Jorg, et al. "Enhanced immunogenicty for CD8+ T Cell induction and complete protective efficacy of malaria DNA vaccination by boosting with modified vaccinia virus Ankara" Nature Medicine, vol. 4(4), Apr. 1998, 397-402.

Hill, Adrian V.S. "Pre-erythrocytic malaria vaccines: towards greater efficacy" Nature Reviews/Immunology, vol. 6(1) Jan. 2006, 21-32.

Peruzzi, Daniela, et al. "A chimpanzee serotype-based adenoviral vector as vaccine for CEA" AACR Meeting, vol. 47, Apr. 2006, p. 330 [Abstract].

Oh, Seong-Taek, et al. "Dendritic cells transduced with recombinant adenoviruses induce more efficient anti-tumor immunity than dendritic cells pulsed with peptide" Vaccine, vol. 24(15), 2006, 2860-2868.

Chapman, Barbara S., et al. "Effect of intron A from human cytomegalovirus (Towne) immediate-early gene on heterologous expression in mammalian cells" Nucleic Acids Research, vol. 19(14), 1991, 3979-3986.

Montgomery, Donna L., et al. "Heterologous and Homologous Protection Against Influenza A by DNA Vaccination: Optimization of DNA Vectors" DNA and Cell Biology, vol. 12(9), 1993, 777-783.

Xu, Zhi-Li, et al. "Strength evaluation of transcriptional regulatory elements for transgene expression by adenovirus vector" Journal of Controlled Release, vol. 81(1-2), 2002, 155-163.

Xu, Zhi-Li, et al. "Woodchuck hepatitis virus post-transcriptional regulation element enhances transgene expression from adenovirus vectors" Biochimica et Biophysics Acta, vol. 1621(3), 2003, 266-271.

Roy, Soumitra, et al."Complete nucleotide sequences and genome organization of four chimpanzee adenoviruses" Virology, vol. 324,(2) 2004, 361-372.

Li, Shengqiang, et al. Viral Vectors for malaria vaccine development, Vaccine, vol. 25(14), Mar. 2007, 2567-2574.

Xiang, Zhiquan, et al., "Novel, chimpanzee serotype 68-based adenoviral vaccine carrier for induction of antibodies to a transgene product," J Virol., vol. 76(6), Mar. 2002; 2667-7.

Rodrigues, "Single immunizing dose of recombinant adenovirus efficiently induces CD8+ T cell-mediated protective immunity against malaria," J Immunol, vol. 158, 1997, 1268-74.

Wille-Reese, "Toll-like receptor agonists influence the magnitude and quality of memory T cell responses after prime-boost immunization in nonhuman primates," J Exp Med., vol. 203(5), May 2006, 1249-58.

* cited by examiner

Uninfected control

Ad.H5.MSP1-42 SP

Ad.H5.MSP1-42 LP

US 10,124,048 B2

ADENOVIRUS VECTORS

FIELD OF THE INVENTION

This invention relates to novel immunogenic adenovirus vector compositions and to their use in immunisation.

BACKGROUND

Vaccination has proved to be one of the most effective means of preventing diseases, particularly infectious diseases. Most vaccines work by inducing antibodies that are protective against infection by the relevant pathogen. However many new vaccines target the cellular arm of the immune system and work by inducing effector and memory T cells. These can target intracellular pathogens and tumours. Many new T cell inducing vaccines that may be used either prophylactically or therapeutically are in development.

T cells induced by vaccination may be useful in various ways. As well as reducing risk of diseases in the vaccinee they may be used in adoptive transfer protocols to reduce risk of infection or disease in those receiving these cells. They may also be useful diagnostically.

An increasingly widely used method of inducing an immune response is to clone an antigen or epitope of interest into a vector. Vectors may be plasmid, bacterial or viral. Plasmid DNA vaccines are under intensive development and a variety of viral vectors appear useful for vaccination. These include poxviruses such as modified vaccinia virus Ankara (MVA), avipox vectors such as fowlpox and canarypox and ALVAC, herpesvirus vectors (including herpes simplex and CMV), alphaviruses and adenoviruses. There is increasing interest in the use of adenoviruses as vaccine vectors because of their ability to induce strong cellular and antibody responses.

Diseases that might be targeted by improved adenovirus vectors include but are not limited to malaria, tuberculosis, HIV/AIDS, HCV, HBV, HSV, HPV, CMV, diseases caused by encapsulated bacteria such as the pneumococcus, parasitic diseases such as leishmaniasis, and a wide range of tumours and cancers, such as lymphoma, leukaemias, melanoma, renal, breast, lung, prostate, pancreatic and colorectal cancers.

SUMMARY OF THE INVENTION

The present invention is based on the inventors surprising discovery that in adenoviral vector vaccines increasing the length of the heterologous promoter which controls expression of the antigen of interest enhances adenoviral vector immunogenicity and protective efficacy.

Adenoviruses form the family Adenoviridae and are classified into five genera (1). First isolated in 1953 from human adenoid tissue removed during tonsillectomy (2), a vast number of species have now been described that are infective to humans and a wide range of animals. All adenoviruses have a similar virion—medium-sized (60-90 nm), non-enveloped, icosahedral particles, with a protein capsid (240 hexons and 12 pentons) enclosing a ~34-43 kbp double-stranded DNA genome within the core (3). Fifty-one human adenovirus (AdHu) serotypes have so far been described, based on serological studies of cross-neutralising antibody responses to the hexon protein and terminal knob of the penton fibre. These serotypes have been further grouped into six subgroups or species (A-F) within the Mastadenovirus genus, based on phylogenetic analysis and their haemagglutination reaction (1). Adenoviruses show a broad tropism with most human serotypes, including the widely studied AdHu5 (subgroup C), initially binding to the Coxsackie adenovirus receptor (CAR) (4), followed by internalisation of the virion upon the interaction of Arg-Gly-Asp (RGD) motifs in the penton base with $\alpha_v\beta_3$- or $\alpha_v\beta_5$-integrins (5). CAR is widely expressed on many cell types, but only on dendritic cells (DCs) at low levels. Some viruses within subgroup B do not bind CAR. AdHu35, for example, binds the complement regulatory protein membrane cofactor protein (MCP/CD46) (6), whilst AdHu3 attaches to the costimulatory molecules CD80 (B7.1) and CD86 (B7.2) expressed by APCs (7). Some serotypes are ubiquitous and infect most children during early infancy, such as AdHu1, 2 and 5, causing acute mild upper respiratory infections. Others, however, can lead to serious and even fatal infections, such as pneumonia (AdHu3 and 7), especially in immunocompromised individuals (8) and children (9).

Adenoviruses were initially developed as vehicles for gene therapy. Attempts to replace missing or faulty genes by adenoviral gene transfer were largely unsuccessful in experimental animals and human volunteers alike due to innate and adaptive immune responses induced by the adenoviral antigens (3). However, the demonstration by gene therapists of the induction of potent cellular and humoral transgene-specific immune responses pioneered the use of these viruses as vaccine vectors with highly successful results first demonstrated using a recombinant rabies virus glycoprotein (10). The adenoviral genome is well characterised and comparatively easy to manipulate (11, 12). Deletion of crucial regions of the viral genome, such as E1, renders the vectors replication-defective, which increases their predictability and eliminates unwanted pathogenic side effects. Replication-deficient adenoviruses can be grown to high titre in tissue culture, using cell lines that provide the missing essential E1 gene products in trans (13). They can be applied systemically as well as through mucosal surfaces and their relative thermostability facilitates their clinical use. Whilst bovine, porcine, and ovine adenoviruses are being explored for veterinary use (3), studies of adenovirus vectors of differing human serotype have shown variable immunogenicity. The majority of studies now focus on the most promising candidates, including AdHu5, AdHu35 and AdHu11. These vectors can induce potent and protective T and B cell-mediated responses against a range of viral and parasitic encoded antigens (10, 14-17). However, problems surrounding pre-existing immunity to ubiquitous viruses such as AdHu5 and AdHu35 remain a big hurdle to the clinical deployment of these vectors. Depending on the region under study, 35-80% of human adults carry AdHu5-neutralising antibodies, and 5-15% AdHu35-neutralising antibodies (18).

E1-deleted replication-defective adenovirus vectors can be generated from "molecular clones", in which the entire genome is carried within a bacterial plasmid (11). Vaccine constructs can be ligated into the E1-deletion site using commercially available kits. Upon removal of the bacterial sequences by restriction enzyme digest, and exposure of the inverted terminal repeats (ITRs), the plasmid can be transfected into a packaging cell line that supplies the essential E1 gene product in trans, thus generating the pure recombinant virus.

The adenoviral capsid will only allow a 5% increase in genome size before efficient packaging and viral stability is disrupted—an extra 1.8 kbp in the case of the well-studied vector AdHu5 (3). Vectors deleted of E1 and the nonessential E3 region (21) can accommodate up to 7.5 kbp of foreign DNA and remain the leading choice for vaccine studies using this vector.

Therefore, according to a first aspect of the present invention there is provided ann immunogenic composition comprising an adenoviral vector, said adenoviral vector further comprising a promoter comprising a fragment of the 5' untranslated region of the CMV IE1 gene including intron A and a nucleic acid sequence encoding a pathogen or tumour antigen under the control of said promoter; wherein said antigen is not a murine malaria parasite antigen.

In one embodiment, the composition may be a vaccine composition. Preferably, the vaccine composition is suitable for human administration and can be used to elicit a protective immune response against the encoded antigen.

In a preferred embodiment, the adenoviral vector is a simian adenoviral vector. More preferably, the simian adenoviral In a preferred embodiment, the adenoviral vector is a simian adenoviral vector. More preferably, the simian adenoviral vector is AdC6 (C6), AdC7 (C7), AdC9 (C9) vector. These viruses are detailed by S. Roy et al. Virology (2004) Volume 324, pp 361-372. Therein AdC6 is referred to as SAdV-23; AdC7 is referred to as SAdV-24; and AdC9 is referred to as SAdV-25. In other publications AdC9 is also called AdC68 (e.g. Fitzgerald et al. J Immunology 2003, 170:1416-22).

It will be understood that the development of simian adenovirus vectors, for example, chimpanzee adenoviruses, against which pre-existing immunity is prevalent neither in humans (1-2%) nor in some other simian species, such as rhesus macaques, often used for pre-clinical testing (19, 20) is desirable.

It will be further understood that in many applications it is preferable for the adenovirus vector to be replication deficient meaning that they have been rendered incapable of replication because of a functional deletion, or complete removal, of a gene encoding a gene product essential for viral replication. By way of example, the vectors of the invention may be rendered replication defective by removal of all or a part of the E1 gene, and optionally also the E3 region and/or the E4 region.

It should be understood that CMV promoters are well known in the art. Numerous versions of the CMV Immediate Early (IE) promoter exist as shown in FIG. 1. It is known that these can be used to drive antigen expression in host eukaryotic cells (22). The CMV IE enhancer-promoter has been shown to cause high levels of transgene expression in eukaryotic tissues when compared with other promoters. A DNA vaccine expressing the HIV-1 antigens Gag/Env under the control of the CMV promoter, rather than the endogenous AKV murine leukaemia virus long terminal repeat, was shown to be more immunogenic in macaques (23).

It is further known that inclusion of the CMV intron A results in enhanced transgene expression over the CMV IE enhancer-promoter alone in vitro and in vivo (24, 25) using plasmid DNA vectors.

However, no assessments of the comparative immunogenicity of these vectors with different promoters has been undertaken.

More recently expression of a firefly luciferase gene has been assessed using an AdHu5 vector and better expression observed with the addition of the intron A sequence (26). Again no studies of immune responses were undertaken. It has been suggested that inclusion of the intron may enhance the rate of polyadenylation and/or nuclear transport associated with splicing of pre-mRNA primary transcripts (27).

Such research on promoter function with adenovirus and plasmid vectors has been directed at enhancing transgene expression in order to improve the efficacy of gene therapy vectors, where the desired outcome is high level prolonged expression of the transgene.

It will be apparent to the skilled person that, although some expression is required for immunogenicity, increased expression of a gene does not correlate with increased immunogenicity. Indeed increased expression of a transgene may lead to vector instability or non-viability of the recombinant virus.

It will be apparent that the antigen can be any antigen of interest either exogenous or endogenous. Exogenous antigens include all molecules found in infectious organisms. For example bacterial immunogens, parasitic immunogens and viral immunogens.

Bacterial sources of these immunogens include those responsible for bacterial pneumonia, meningitis, cholera, diphtheria, pertussis, tetanus, tuberculosis and leprosy.

Parasitic sources include malarial parasites, such as *Plasmodium*, as well as trypanosomal and *leishmania* species.

Viral sources include poxviruses, e.g., smallpox virus, cowpox virus and orf virus; herpes viruses, e.g., herpes simplex virus type 1 and 2, B-virus, varicella zoster virus, cytomegalovirus, and Epstein-Barr virus; adenoviruses, e.g., mastadenovirus; papovaviruses, e.g., papillomaviruses such as HPV16, and polyomaviruses such as BK and JC virus; parvoviruses, e.g., adeno-associated virus; reoviruses, e.g., reoviruses 1, 2 and 3; orbiviruses, e.g., Colorado tick fever; rotaviruses, e.g., human rotaviruses; alphaviruses, e.g., Eastern encephalitis virus and Venezuelan encephalitis virus; rubiviruses, e.g., rubella; flaviviruses, e.g., yellow fever virus, Dengue fever viruses, Japanese encephalitis virus, Tick-borne encephalitis virus and hepatitis C virus; coronaviruses, e.g., human coronaviruses; paramyxoviruses, e.g., parainfluenza 1, 2, 3 and 4 and mumps; morbilliviruses, e.g., measles virus; pneumovirus, e.g., respiratory syncytial virus; vesiculoviruses, e.g., vesicular stomatitis virus; lyssaviruses, e.g., rabies virus; orthomyxoviruses, e.g., influenza A and B; bunyaviruses e.g., LaCrosse virus; phiebovi-ruses, e.g., Rift Valley fever virus; nairoviruses, e.g., Congo hemorrhagic fever virus; hepadnaviridae, e.g., hepatitis B; arenaviruses, e.g., 1 cm virus, Lasso virus and Junin virus; retroviruses, e.g., HTLV I, HTLV II, HIV-1 and HIV-2; enteroviruses, e.g., polio virus 1,-2 and 3, coxsackie viruses, echoviruses, human enteroviruses, hepatitis A virus, hepatitis E virus, and Norwalk-virus; rhinoviruses e.g., human rhinovirus; and filoviridae, e.g., Marburg (disease) virus and Ebola virus.

Antigens from these bacterial, viral and parasitic sources can be considered as exogenous antigens because they are not normally present in the host and are not encoded in the host genome.

In contrast, endogenous antigens are normally present in the host or are encoded in the host genome, or both. The ability to generate an immune response to an endogenous antigen is useful in treating tumours that bear that antigen, or in neutralising growth factors for the tumour. An example of the first type of endogenous antigen is HER2, the target for the monoclonal antibody called Herceptin. An example of the second, growth factor, type of endogenous antigen is gonadotrophin releasing hormone (called GnRH) which has a trophic effect on some carcinomas of the prostate, gland.

Preferably, the antigen is an antigen from an infectious pathogen of humans or livestock.

In one preferred embodiment, the antigen is from a pathogen which causes malaria. Preferably, the antigen is a *P. falciparum* antigen.

Preferably, the malaria antigen is a pre-erythrocytic or blood-stage malaria antigen.

In particularly preferred embodiments of the present invention, the malaria antigen is ME-TRAP, CSP, MSP-1 or fragments thereof, or AMA1.

Preferably, when the malaria antigen is an MSP-1 antigen it has the sequence of PfM117 (SEQ ID NO. 1) or PfM128 (SEQ ID NO. 3).

Malaria is a disease against which it has been very difficult to generate protective immunity in both humans and small animal models. Thus the results discussed below indicate that the use of the immunisation approaches described herein have general potential for use in generating very potent vaccines in humans and other species.

In a further preferred embodiment, the antigen in a mycobacterial antigen. Preferably, the antigen is a *M. tuberculosis* antigen. More preferably, the antigen is *M. tuberculosis* antigen 85A.

The inventors have found that the enhanced antigen expression resulting from the presence of the long CMV promoter including intron A leads to a remarkably large and surprising increase in the immunogenic potency of these vaccine vectors, and to enhanced protective efficacy against pathogen challenge.

The above immunogenic viral vector compositions, may be formulated into pharmaceutical dosage forms, together with suitable pharmaceutically acceptable carriers, such as diluents, fillers, salts, buffers, stabilizers, solubilizers, etc. The dosage form may contain other pharmaceutically acceptable excipients for modifying conditions such as pH, osmolarity, taste, viscosity, sterility, lipophilicity, solubility etc.

Suitable dosage forms include solid dosage forms, for example, tablets, capsules, powders, dispersible granules, cachets and suppositories, including sustained release and delayed release formulations. Powders and tablets will generally comprise from about 5% to about 70% active ingredient. Suitable solid carriers and excipients are generally known in the art and include, e.g. magnesium carbonate, magnesium stearate, talc, sugar, lactose, etc. Tablets, powders, cachets and capsules are all suitable dosage forms for oral administration.

Liquid dosage forms include solutions, suspensions and emulsions. Liquid form preparations may be administered by intravenous, intracerebral, intraperitoneal, intradermal, parenteral or intramuscular injection or infusion. Sterile injectable formulations may comprise a sterile solution or suspension of the active agent in a non-toxic, pharmaceutically acceptable diluent or solvent. Suitable diluents and solvents include sterile water, Ringer's solution and isotonic sodium chloride solution, etc. Liquid dosage forms also include solutions or sprays for intranasal administration.

Aerosol preparations suitable for inhalation may include solutions and solids in powder form, which may be combined with a pharmaceutically acceptable carrier, such as an inert compressed gas.

Also encompassed are dosage forms for transdermal administration, including creams, lotions, aerosols and/or emulsions. These dosage forms may be included in transdermal patches of the matrix or reservoir type, which are generally known in the art.

Pharmaceutical preparations may be conveniently prepared in unit dosage form, according to standard procedures of pharmaceutical formulation. The quantity of active compound per unit dose may be varied according to the nature of the active compound and the intended dosage regime.

The active agents are to be administered to human subjects in "therapeutically effective amounts", which is taken to mean a dosage sufficient to provide a medically desirable result in the patient. The exact dosage and frequency of administration of a therapeutically effective amount of active agent will vary, depending on such factors as the nature of the active substance, the dosage form and route of administration.

The medicaments and pharmaceutical compositions of the present invention may be administered systemically or locally. This is applicable to both the use and method aspects of the invention equally. Systemic administration may be by any form of systemic administration known, for example, orally, intravenously or intraperitoneally. Local administration may be by any form of local administration known, for example topically.

In particularly preferred embodiments the pharmaceutical composition includes at least one pharmaceutically acceptable excipient.

According to a second aspect of the present invention there is provided an adenoviral vector comprising a promoter further comprising a fragment of the 5' untranslated region of the CMV IE1 gene including intron A and a nucleic acid sequence encoding a pathogen or tumour antigen under the control of said promoter for use as a medicament.

Preferably, the adenoviral vector is a simian adenoviral vector.

Preferably the adenoviral vector is replication deficient.

Preferably, the antigen is an antigen from an infectious pathogen of humans or livestock.

According to a third aspect of the present invention there is provided the use of an adenoviral vector comprising a promoter further comprising a fragment of the 5' untranslated region of the CMV IE1 gene including intron A and a nucleic acid encoding a malarial antigen in the manufacture of a vaccine or immunotherapeutic for the prevention or treatment of malaria.

Preferably, the malaria antigen is not from a murine parasite.

Preferably, the adenoviral vector is a simian adenoviral vector.

Preferably the adenoviral vector is replication deficient.

In a preferred embodiment, the encoded malaria antigen is a *P. falciparum* antigen. More preferably, the malarial antigen is a pre-erythrocytic or blood-stage malaria antigen. Even more preferably, the malarial antigen is ME-TRAP, CSP, MSP-1 or fragments thereof, or AMA1.

In a most preferred embodiment, when the malarial antigen is an MSP-1 antigen it has the sequence of PfM117 (SEQ ID NO. 1) or PfM128 (SEQ ID NO. 3).

According to a fourth aspect of the present invention there is provided the use of an adenoviral vector comprising a promoter further comprising a fragment of the 5' untranslated region of the CMV IE1 gene including intron A and a nucleic acid encoding a *M. tuberculosis* antigen in the manufacture of a vaccine or immunotherapeutic for the prevention or treatment of tuberculosis.

Preferably, the adenoviral vector is a simian adenoviral vector.

Preferably the adenoviral vector is replication deficient.

In a preferred embodiment, the encoded antigen is the *M. tuberculosis* antigen 85A.

According to a fifth aspect of the present invention there is provided an adenoviral vector comprising a promoter further comprising a fragment of the 5' untranslated region of the CMV IE1 gene including intron A and a nucleic acid encoding a malarial antigen for use in the prevention or treatment of malaria.

Preferably, the malaria antigen is not from a murine parasite.

Preferably, the adenoviral vector is a simian adenoviral vector.

Preferably the adenoviral vector is replication deficient.

Preferably, the malaria antigen is a *P. falciparum* antigen.

Preferably, the malaria antigen is a pre-erythrocytic or blood-stage malaria antigen.

Preferably, the malaria antigen is ME-TRAP, CSP, MSP-1 or fragments thereof, or AMA1. More preferably, the malaria antigen is an MSP-1 antigen has the sequence of PfM117 (SEQ ID NO, 1) or PfM128 (SEQ ID NO. 3).

According to a sixth aspect of the present invention, there is provided an adenoviral vector comprising a promoter further comprising a fragment of the 5' untranslated region of the CMV IE1 gene including intron A and a nucleic acid encoding a *M. tuberculosis* antigen for use in the prevention or treatment of tuberculosis.

Preferably, the adenoviral vector is a simian adenoviral vector.

Preferably, the adenoviral vector is replication deficient.

In a preferred embodiment, the encoded antigen is *M. tuberculosis* antigen 85A.

It will be readily apparent that the medicaments described in any of the above aspects may comprise one or more pharmaceutically acceptable vehicles, carriers, diluents, excipients or adjuvants.

According to a seventh aspect of the present invention there is provided a product, combination or kit comprising;
a) a priming composition comprising an adenoviral vector, said adenoviral vector further comprising a long heterologous promoter, wherein the promoter is a fragment of the 5' untranslated region of the CMV IE1 gene including intron A, and at least one nucleic acid sequence encoding a pathogen or tumour antigen, wherein the antigen is not a murine malaria parasite antigen; and
b) boosting composition comprising a recombinant pox virus vector, said pox virus vector further comprising at least one nucleic acid sequence encoding a pathogen or tumour antigen which is the same as at least one antigen of the priming composition.

Preferably, the adenoviral vector is a simian adenoviral vector. More preferably, the simian adenoviral vector is AdC6 (C6), AdC7 (C7), or AdC9 (C9) vector.

Preferably, the antigen is not a murine malaria parasite antigen.

In a preferred embodiment, the promoter excludes Exon B.

Preferably, the antigen is an antigen from an infectious pathogen of humans or livestock.

In one preferred embodiment, the antigen is from a pathogen which causes malaria. Preferably, the antigen is a *P. falciparum* antigen. More preferably, a pre-erythrocytic or blood-stage malarial antigen. Even more preferably, the malarial antigen is ME-TRAP, CSP, MSP-1 or fragments thereof, or AMA1.

When the malarial antigen is an MSP-1 antigen preferably it has the sequence of PfM117 (SEQ ID NO. 1) or PfM128 (SEQ ID NO. 3).

In a further preferred embodiment, the antigen in a mycobacterial antigen. More preferably, the antigen is a *M. tuberculosis* antigen. Even more preferably, the antigen is *M. tuberculosis* antigen 85A.

Also provided is the use of the combination for production of a kit for generating a protective T cell response against at least one target antigen of a pathogen or tumour in a subject.

According to an eighth aspect of the present invention there is provided a method of eliciting an immune response in a subject comprising administering an effective amount of an immunogenic composition or vaccine according to the first aspect of the present invention sufficient to elicit an immune response.

It will be apparent that the subject can be administered the composition or vaccine for either prophylactic or immunotherapeutic purposes, depending on the antigen.

In a preferred embodiment, the subject is immunised using a heterologous prime-boost regimen.

The skilled person will understand that heterologous prime-boost refers to a regimen wherein an effective amount of a first immunogenic composition or vaccine according to the present invention is administered to an individual at a first time point and subsequently an effective amount of a second immunogenic composition or vaccine encoding the same antigen as the immunogenic composition or vaccine according to the present invention is administered at a second time point. It will be understood that in an heterologous prime-boost regimen the first and second immunogenic composition or vaccines are different.

Preferably, the second immunogenic composition or vaccine is administered 2-8 weeks after the first immunogenic composition or vaccine.

It will be readily apparent to the skilled person that the term subject as used in the present invention relates to any animal subject. This may particularly be a mammalian subject, including a human.

Thus products of the invention may be useful not only in human use but also in veterinary uses, for example in the treatment of domesticated mammals including livestock (e.g. cattle, sheep, pigs, goats, horses or in the treatment of wild mammals, such as those captive in zoos).

In another aspect, the product of the invention may be used for the treatment of non-mammalian subjects, including fowl such as chickens, turkeys, duck, geese and the like.

According to a ninth aspect of the present invention there is provided a simian adenoviral vector comprising a long heterologous promoter, wherein the promoter is a fragment of the 5' untranslated region of the CMV IE1 gene including intron A and at least one nucleic acid sequence encoding a pathogen or tumour antigen of interest.

Preferably, the promoter does not include exon B.

Preferably the simian adenoviral vector is replication deficient.

Preferably, the antigen is an antigen from an infectious pathogen of humans or livestock.

In one preferred embodiment, the antigen is from a pathogen which causes malaria. Preferably, the antigen is a *P. falciparum* antigen. More preferably, a blood-stage malarial antigen. Even more preferably, the malarial antigen is ME-TRAP, CSP, MSP-1 or fragments thereof, or ANAL When the malarial antigen is an MSP-1 antigen preferably it has the sequence of PfM117 (SEQ ID NO. 1) or PfM128 (SEQ ID NO. 3).

In a further preferred embodiment, the antigen in a mycobacterial antigen. More preferably, the antigen is a *M. tuberculosis* antigen. Even more preferably, the antigen is *M. tuberculosis* antigen 85A.

According to a tenth aspect of the present invention there is provided a method for enhancing the T cell immunogenicity of an immunogenic adenoviral vector composition or vaccine according to the first aspect, comprising administering said vaccine in combination with a CpG adjuvant.

It will be apparent that the CpG adjuvant can be administered prior to, concomitantly with, or subsequently to said immunogenic composition or vaccine.

According to an eleventh aspect of the present invention there is provided a composition comprising an immunogenic adenoviral vector composition or vaccine according to first aspect and a CpG adjuvant.

According to a twelfth aspect of the present invention there is provided the composition according to the eleventh aspect for use as a medicament.

According to a thirteenth aspect there is provided a kit comprising the immunogenic adenoviral vector composition or vaccine of first aspect and a CpG adjuvant for use in generating an immune response in a subject against at least one pathogen or tumour antigen.

It will be understood that an immunogenic composition referred to in any of the above aspects may in certain embodiments be a vaccine.

It will be apparent that the antigen according to any aspect of the present invention may be any antigen of interest as described in relation to the first aspect.

It will be apparent that any feature described as preferred in connection with one aspect of the invention is also preferred in relation to other aspects of the invention unless otherwise stated, and that preferred embodiments relating to one feature are disclosed in combination with preferred embodiments relating to other features.

The invention will now be further described with reference to the following examples and figure in which:—

BRIEF DESCRIPTION OF THE DRAWINGS

FIG. 8A-FIG. 8B shows P. yoelii sporozoite challenge of AdM42 (8 wks) immunised BALB/c mice. BALC/c mice were immunised as described in table 1, and challenged with 50 P. yoelii sporozoites 14 days after the final immunisation (day 0). Blood-stage parasitaemia was monitored daily by Giemsa-stained thin-blood smear from day 5, and percentage pRBCs calculated. Results are shown for: (FIG. 8A) unimmunised naïve controls n=6; (FIG. 8B) AdM42 (8 wks) n=6. Unprotected mice which succumbed to infection or were sacrificed (at ≥80% blood-stage parasitaemia) are indicated by the cross symbol †.

(FIG. 9B) Kinetics of the immune response to ME.TRAP. BALB/c mice were immunized with adenoviral ($1 \times 10^{10}$ vp) and poxviral vectors ($1 \times 10^{7}$ pfu). The magnitude of the immune response was measured after stimulation of splenocytes with Pb9 peptide and detection of IFNgamma$^+$-producing CD8$^+$ T cells by flow cytometry at different intervals. (FIG. 9C) Total number of IFNgamma$^+$ CD8$^+$ T cells per spleen during the peak of the effector and memory responses for each vector. Calculations were performed in the same groups of mice from FIG. 1b. (FIG. 9D) the percent of IFNgamma$^+$ CD8$^+$ T cells from representative mice upon Pb9 peptide stimulation. Upper panel shows the peak of the effector response for each vector (20 days post-prime for adenoviral vectors and 7 days post-prime for poxviral vectors). The memory phase was measured at day 60 post-prime. Data are mean±s.e.m. for three mice per group.

(FIG. 10A) Breadth of the immune response. Mice were immunized with $1 \times 10^9$ vp of adenoviral vectors coding for ME.TRAP. Immune responses were measured 2 weeks later by ELISPOT after stimulation of cells with overlapping peptides covering the whole sequence of the ME.TRAP transgene. Data are mean±s.d. for three mice per group. (FIG. 10B) The percent of IFNgamma$^+$ CD8$^+$ and CD4$^+$ T cells from a pool of 3 mice upon peptide stimulation. Upper panel shows the CD8$^+$ T-cell response for each vector (20 days post-prime) and lower panel shows the CD4$^+$ T-cell response.

BALB/c mice were immunized as described in FIG. 1. Data show percentage of CD8$^+$ IFNgamma$^+$ CD43$^{hi}$ (FIG. 11A) and CD8$^+$ IFNgamma$^+$ Granzyme B coexpression (FIG. 11B). (FIG. 11C) Granzyme B expression from representative mice at indicated days post-prime. Histogram shows GrB expression (white background) after staining with anti-human GrB, compared to an isotype control (gray background). The number corresponds to MFI of the positive sample (black solid line). Data in graphs are mean±s.e.m. for three mice per group.

Figure 15A:
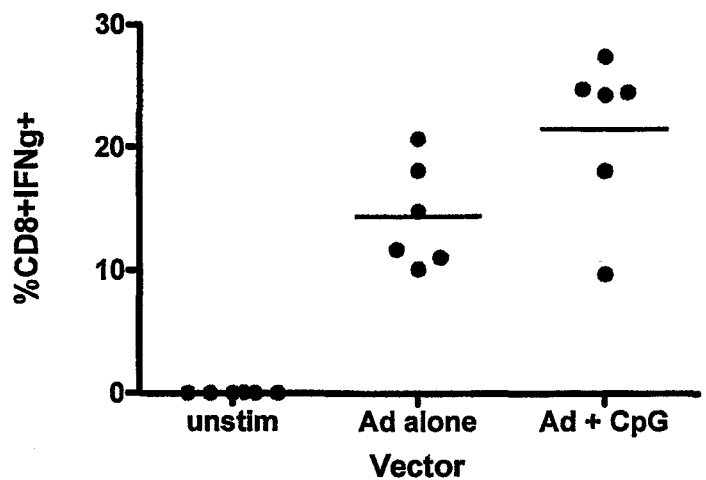
FIG. 15A-FIG. 15B shows assessment of the potential immune enhancing effect of a CpG sequence (CpG 1826) added to the AdHu5 PfM115 adenovirus vector.
Figure 15B:
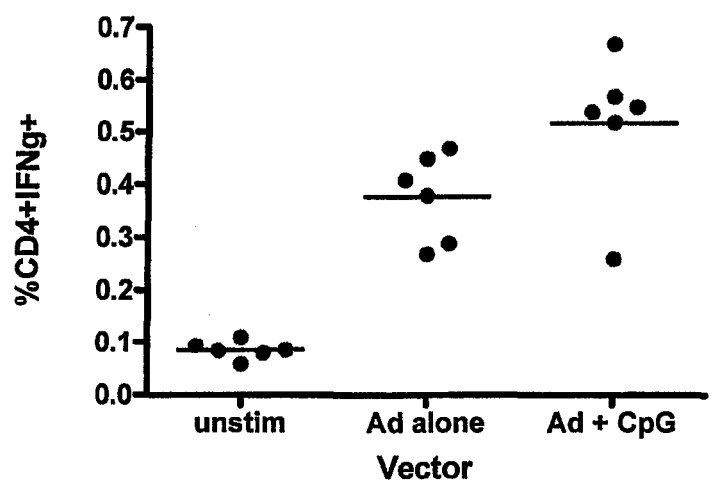

BALB/c mice were immunised intradermally on one occasion and T cell responses evaluated 14 days later. A large pool of overlapping peptides spanning the insert were used to evaluate CD8 (FIG. 15A) and CD4 (FIG. 15B) T cell IFN-gamma responses.

EXAMPLES

In the following Examples a number of antigens have been used in the adenovirus vector vaccines of the current invention:

The *Mycobacterium tuberculosis* antigen 85A (28, 29).
The 42 kDa C-terminus of the blood-stage malarial antigen merozoite surface protein-1 (MSP-1$_{42}$) from the murine parasite *Plasmodium yoelii* (30).
The malaria sporozoite antigen circumsporozoite protein (CSP) from the murine malaria parasite *P. berghei*
The pre-erythrocytic malarial antigen insert multi-epitope string—thrombospondin-related adhesion protein (ME-TRAP) from *P. falciparum* (31, 32).
A fusion protein of regions of the *P. falciparum* blood-stage antigen NSP-1 denoted PfM117
A fusion protein of regions of the *P. falciparum* blood-stage antigen MSP-1 denoted PfM128

Figure 1:
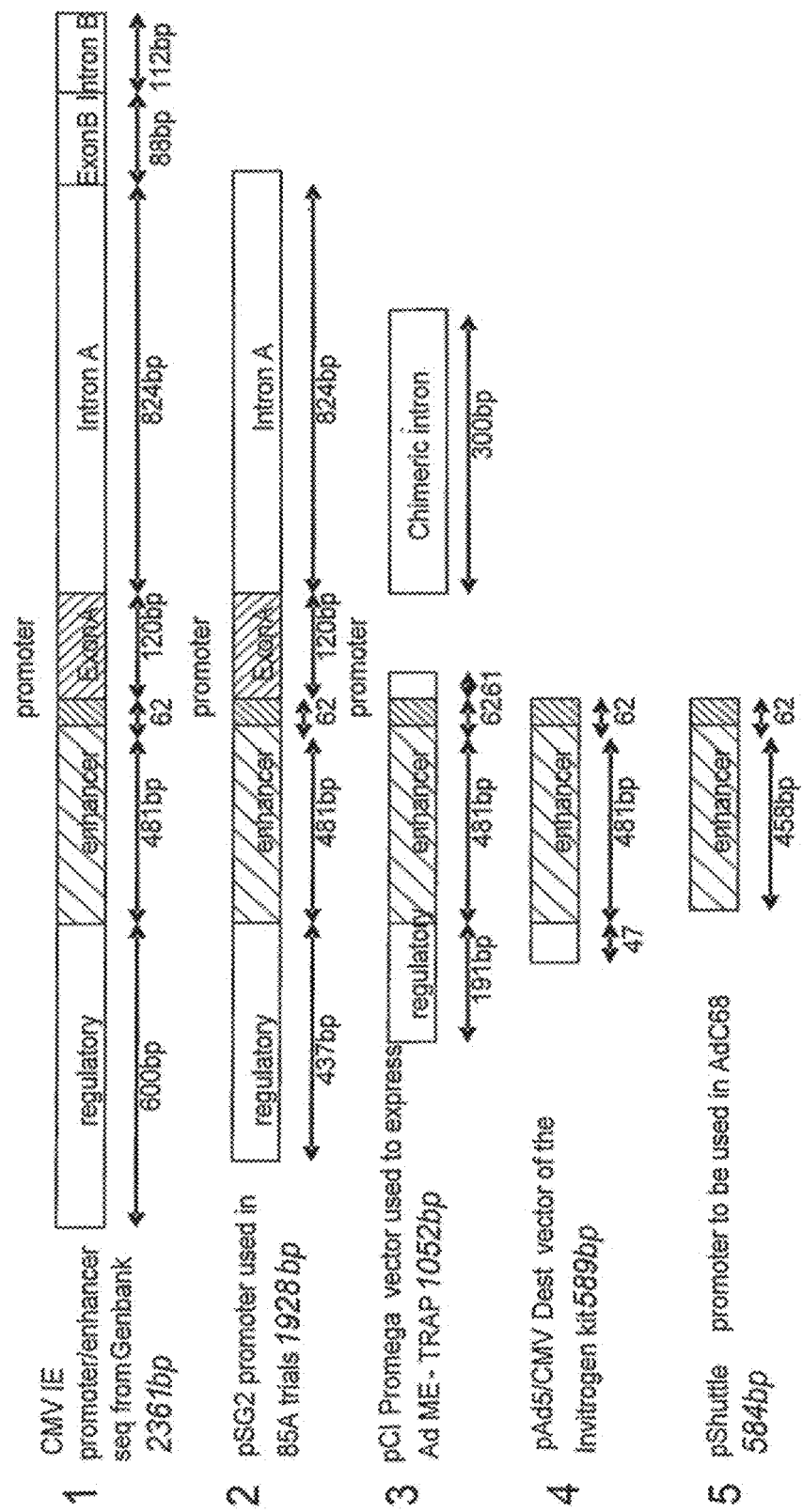
FIG. 1 shows CMV Promoters.
1) Complete CMV IE promoter sequence from GenBank. 2) The "long" 1.9 kbp version of the promoter referred in this document. 3) Promoter with chimeric intron from Promega® (Southampton, UK) used to express ME-TRAP. 4) The "small" 0.6 kbp version of the promoter referred to in this document.
Figure 2A:
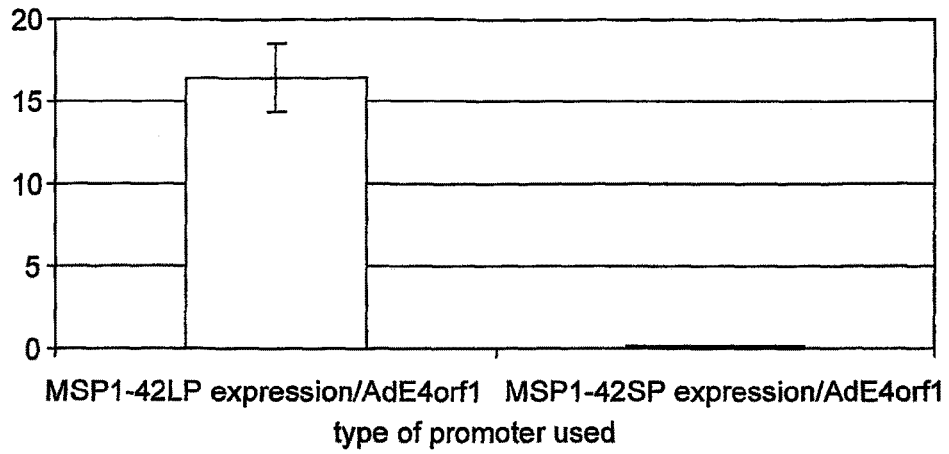
FIG. 2A-FIG. 2B shows quantification of antigen expression by quantitative real-time RT-PCR. 293A cells were infected with AdHu5 expressing (FIG. 2A) MSP-1$_{42}$ or (FIG. 2B) 85A, under the control of the long or small promoter. Cells were harvested into RLT buffer, and the RNA extracted and reverse transcribed into cDNA. The levels of MSP-1$_{42}$, 85A and AdHu5 E4orf1 cDNA target sequences were measured by real-time PCR. Relative gene expression was calculated as the ratio of target antigen mRNA copies to E4orf1 copies. Each column represents the mean ratio±S.E.
Figure 2B:
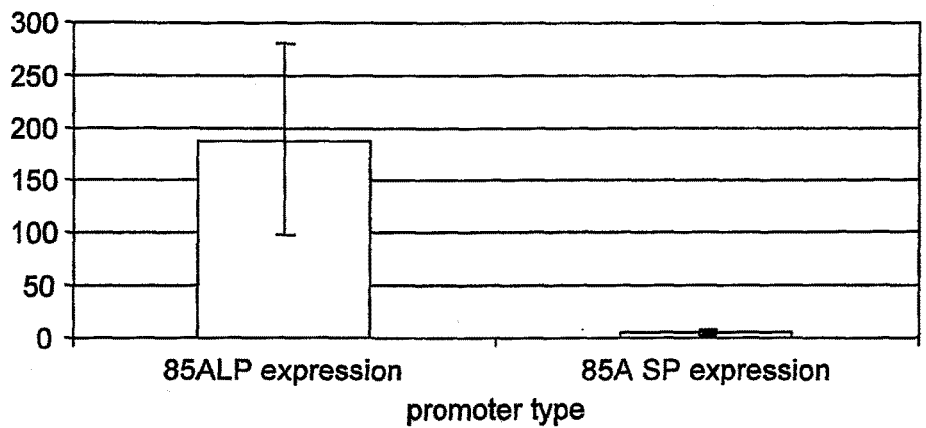
Figure 3:
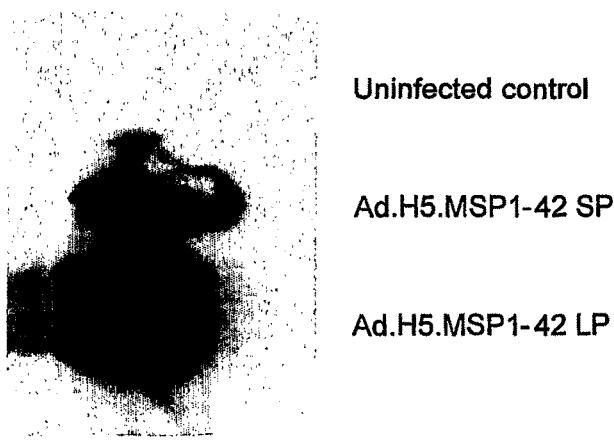
FIG. 3 shows quantification of MSP-1$_{42}$ antigen expression by Western Blot. 293A cells were infected with no virus (lane 1) Ad42SP (lane 2) or Ad42LP (lane 3) in cell culture medium excluding FCS. Cell culture supernatants were harvested once 100% CPE was evident, and concentrated by centrifugation through Centricon YM 30 tubes (Millipore, Watford, UK). Proteins from cell culture supernatants were separated by SDS-PAGE and electroblotted onto nitrocellulose membrane, before staining with HRP-conjugated mAb to the C-terminal PK/V5 tag. The blot was developed and exposed to photographic film. The predicted molecular mass for MSP-1$_{42}$-PK is 46 kDa.

Example 1: Production of Adenovirus Vector Vaccines Containing Murine Malaria Antigens and a Tuberculosis Antigen 1.1 Enhancement of Antigen Expression by CMV Promoter in Recombinant AdHu5 Vectors AdHu5 vectors encoding murine malaria *P. yoelii* MSP-1$_{42}$ or antigen85A from *M. tuberculosis* were compared, using vectors which drive transgene expression by either the "small" 0.6 kbp version of the CMV IE promoter (lacking intron A), or the "long" 1.9 kbp version of the promoter (with regulatory element, enhancer and intron A). The small and long versions of the promoter are referred to as SP and LP respectively. The level of antigen expression by AdHu5 vectors was assayed in vitro by quantitative real-time RT-PCR (FIG. 2). The level of antigen expression was normalised to the AdHu5 E4orf1 transcript. In both cases, significantly higher levels of antigen expression were measured following infection of 293A cells with AdHu5 vectors expressing antigen under the control of the long promoter. The overall level of antigen expression may be antigen dependent, given both vectors encoding 85A expressed significantly higher levels of antigen compared to either vector encoding MSP-1$_{42}$. These results were confirmed for the vectors encoding MSP-1$_{42}$ by Western Blot (FIG. 3). The MSP-1$_{42}$ antigen includes the PK epitope (amino acid sequence IPNPLLGLD; SEQ ID NO: 8) as a C-terminal fusion. Antigen is detected using the monoclonal antibody anti-PK (also known as anti-V5) from Serotec (Oxford, UK).

Figure 4A:
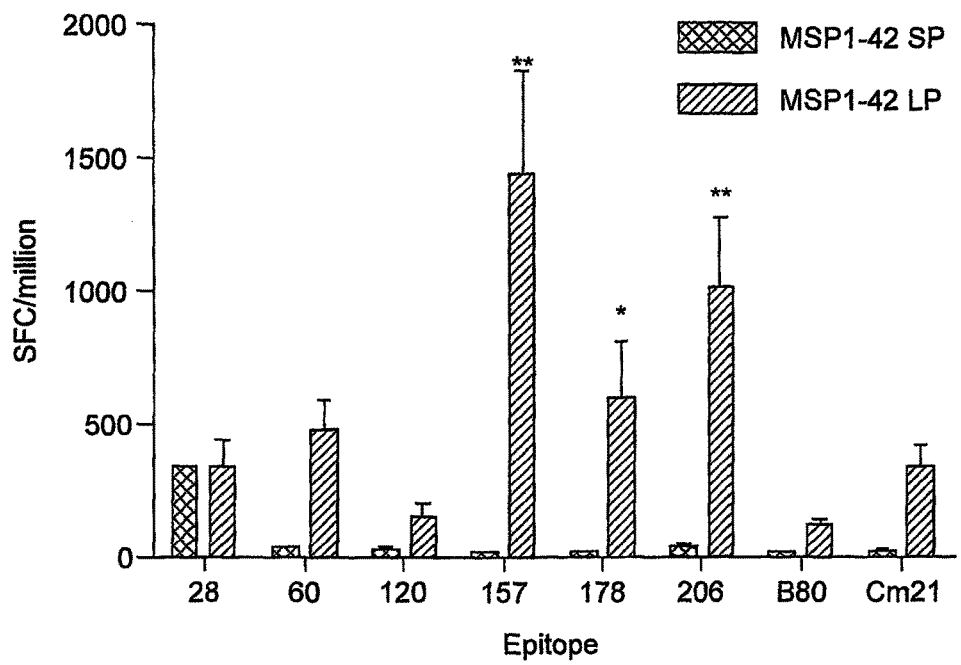
FIG. 4A-FIG. 4B shows peptide-specific IFN-γ-secreting T cell responses induced by (FIG. 4A) Ad-MSP-1$_{42}$ or (FIG. 4B) Ad-85A vaccination. BALB/c mice were immunized i.d. with $10^{10}$ vp of each adenovirus, and responses measured in the spleens of immunised mice 14 days post-immunisation by ex-vivo IFN-γ ELISPOT. Columns represent the mean number of IFN-γ SFC per million splenocytes±S.E. (n=3 mice/group). * p≤0.05, ** p≤0.01, comparing responses between groups that were immunised with AdHu5 vectors expressing the relevant antigen under the control of the long (LP) or short (SP) promoter.
Figure 4B:
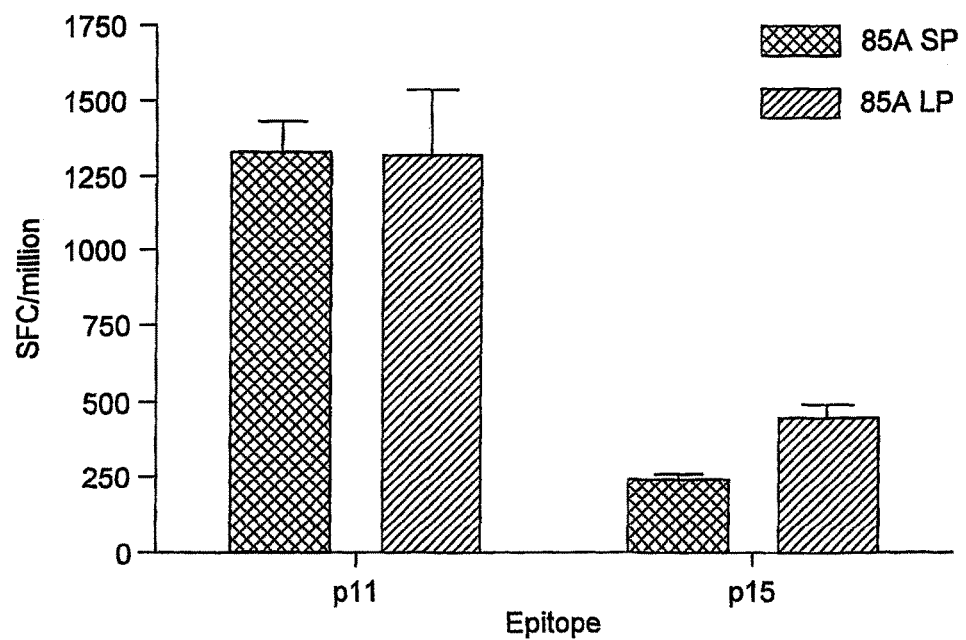

1.2 Enhancement of T Cell Immunogenicity by CMV Promoters in Recombinant AdHu5 Vectors Groups of BALB/c mice were immunised intradermally (i.d.) with $10^{10}$ vp of each adenovirus, and responses measured in the spleen to known CD8$^+$ and CD4$^+$ T cell epitopes 14 days later by ex-vivo interferon-gamma (IFN-γ) ELISPOT (FIG. 4). The epitopes in MSP-1$_{42}$ are all known H-2$^d$ class I-restricted epitopes (FIG. 4a). p11 is a known H-2$^d$ class I-restricted epitope in 85A, whilst p15 is class II-restricted (FIG. 4b). Responses were only detected against known epitopes in MSP-1$_{42}$ when mice were immunised with Ad42LP, whereas responses to 85A were induced by both vectors, with those against p15 tending to be stronger in the Ad85ALP group. These data correlate with the level of antigen expression measured by real-time RT-PCR (FIG. 2).

Figure 5:
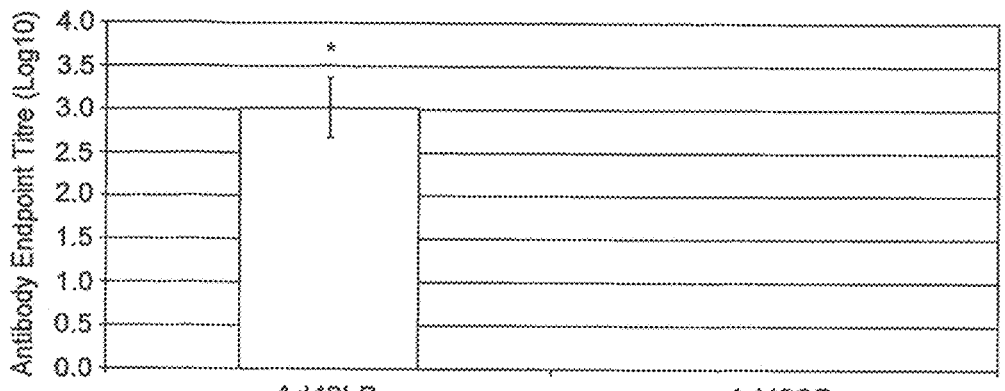
FIG. 5 shows MSP-1$_{19}$-specific whole IgG antibody responses induced by Ad42SP or Ad42LP. BALB/c mice were immunized i.d. with $10^{11}$ vp Ad42SP or with $5 \times 10^{10}$ vp Ad42LP. Whole IgG responses against MSP-1$_{19}$ were measured by anti-GST-MSP-1$_{19}$ ELISA in the serum of mice 13 days post-immunisation. GST controls all negative (data not shown). Columns represent the mean log 10 endpoint titre ±95% C.I. (n=3 mice/group). * p≤0.05, comparing responses between groups.
Figure 6:
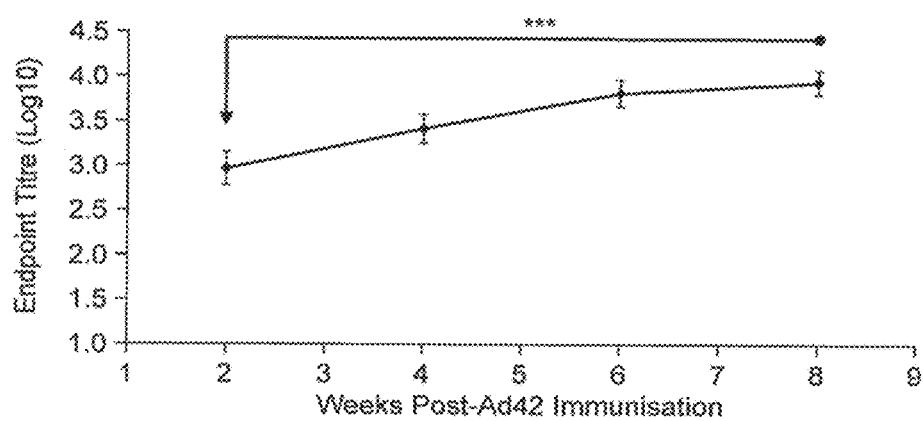
FIG. 6 shows kinetics of MSP-1$_{19}$-specific whole IgG antibody responses induced by Ad42LP. BALB/c mice were immunised once i.d. with $5 \times 10^{10}$ vp Ad42 at week 0. Whole IgG responses against MSP-1$_{19}$ were assayed by anti-GST-MSP-1$_{19}$ ELISA in the serum of mice taken at 14 day intervals. Points represent the results of two experiments as the mean log 10 endpoint titre ±95% C.I. (n=18 mice). *** p≤0.001, comparing differences between time points by paired analysis of data from individual mice.
Figure 7:
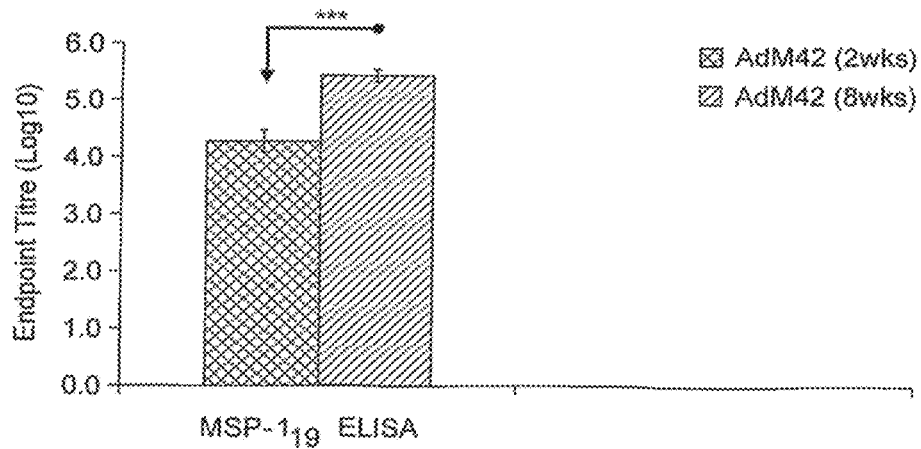
FIG. 7 shows MSP-1$_{19}$-specific IgG antibody responses induced by AdM42 prime-boost vaccination. BALB/c mice were immunised i.d. with $5 \times 10^{10}$ vp Ad42 LP and boosted i.d. with $5 \times 10^{7}$ pfu MVA expressing the same antigen either two or eight weeks later. Whole IgG responses against MSP-1$_{19}$ were measured by anti-GST-MSP-1$_{19}$ ELISA in the serum of mice 13 days after the second immunisation. Columns represent the results of two or three experiments as the mean log 10 endpoint titre ±95% C.I. (n=11-22 mice/group). *** p≤0.001, comparing responses between the two groups.

1.3 Enhancement of Antibody Immunogenicity by CMV Promoters in Recombinant AdHu5 Vectors Groups of BALB/c mice were immunised i.d. with $10^{10}$ vp of Ad42LP or Ad42SP. Whole IgG antibody responses against the C-terminus of MSP-1$_{42}$ (MSP-1$_{19}$) were assayed by ELISA two weeks later (FIG. 5). There was no detectable antibody responses against MSP-1$_{19}$ following Ad42SP immunisation, whereas Ad42LP primed a significantly higher response, with an endpoint titre of approximately 1000. This response, induced by Ad42LP, continues to increase over time, reaching a plateau by 6-8 weeks (FIG. 6). This antibody response can be boosted to a significantly higher level by MVA encoding the same antigen. Antibody responses are significantly higher following this heterologous AdM prime-boost regime, if Ad42LP primed mice are boosted 8 weeks rather than 2 weeks later (FIG. 7).

1.4 Protection of Mice Against Lethal Blood-Stage P. yoelii Challenge b AdM-MSP-1$_{42}$ Immunisation The protection provided by the prime boost regime was investigated by examination of the protection provided by AdM-MSP-1$_{42}$ immunisation against lethal blood-stage P. yoelii challenge in mice. Groups of BALE/c mice were immunised i.d. with 5×10$^{10}$ vp of Ad42LP and boosted with MVA expressing the same antigen two or eight weeks later. All immunisation regimes utilised the Ad42LP vector, and MVA expressing the same antigen. Mice were challenged i.v. with 10$^4$ P. yoelii pRBCs 14 days after the final immunisation. Homologous prime-boost regimes were included as a comparison. 76% of mice immunised with the AdM42 regime using an eight week prime-boost interval were completely protected against a lethal challenge with 10$^4$ parasitised red blood cells (pRBCs) as shown in Table 1.

TABLE 1

| Immunisation Regime | No. Mice Protected/ Challenged | % Protected | Median (Range) Peak % Parasitaemia of Protected Mice |
|---|---|---|---|
| AdM42 (2 wks) | 0/6 | 0% | N/A |
| AdM42 (8 wks) | 4/5 + 4/6 + 5/6 | 76% | 1.2% (0.004%-27.7%) |
| MM42 (8 wks) | 0/3 | 0% | N/A |
| AdAd42 (8 wks) | 0/3 | 0% | N/A |
| Naïve | 0/4 + 0/4 + 0/4 | 0% | N/A |

The table outlines the results from individual experiments and the overall level of protective efficacy. The median and range of peak parasitaemia of those mice that survived in each group are included. Exponential parasite growth results in ≥80% blood-stage parasitaemia within 5-7 days post-infection in naïve or unprotected mice, at which point mice are sacrificed. Protected mice can control and ultimately clear blood-stage malaria infection.

These results could be replicated in a second strain of mouse, and in this case 100% of C57BL/6 mice survived challenge, compared to none of the naïve unimmunised controls as shown in Table 2.

TABLE 2

| Immunisation Regime | No. Mice Protected/ Challenged | % Protected | Median (Range) Peak % Parasitaemia of Protected Mice |
|---|---|---|---|
| AdM42 (8 wks) | 6/6 | 100% | 14.7% (3.7%-56.4%) |
| Naïve | 0/6 | 0% | N/A |

Figure 8A:
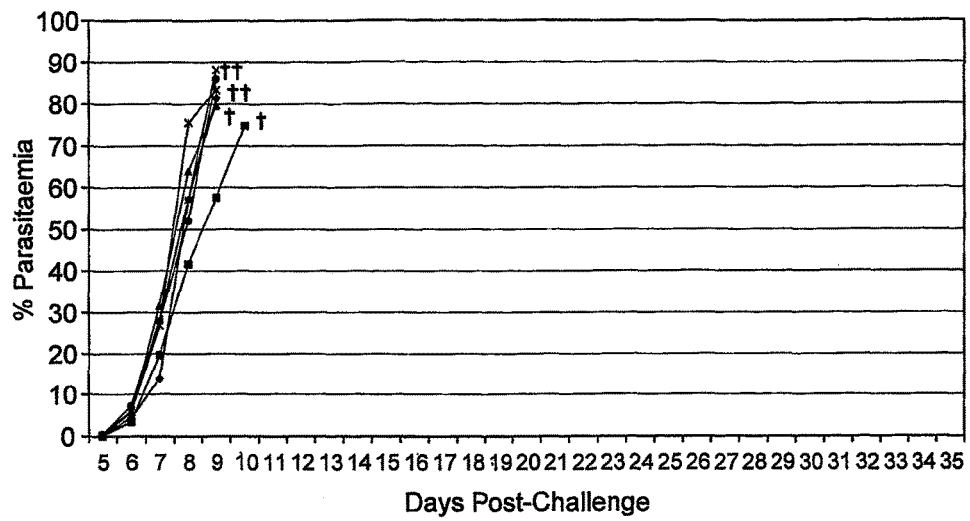
Figure 8B:
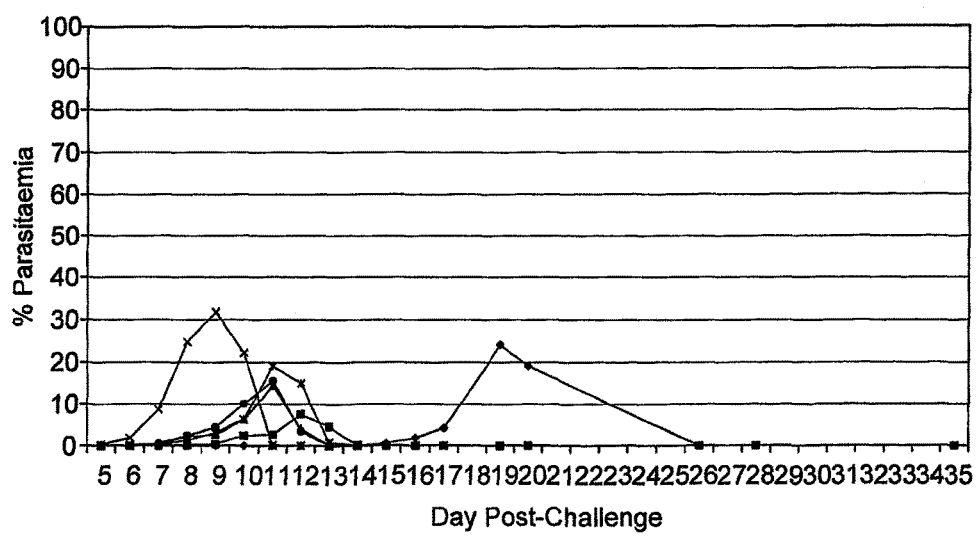

100% of BALB/c mice immunised with this regime were also protected against a challenge with 50 P. yoelii sporozoites—the natural mode of malaria infection (FIG. 8).

1.5 Sterile Protection of Mice to P. berghei Sporozoite Challenge by AdHu5-PbCSP Immunisation AdHu5 vector recombinant for the circumsporozoite protein (CSP) from P. berghei was generated, with the antigen under the control of the long promoter (33). BALB/c mice were immunised as indicated in Table 3. Some groups of mice received a single immunisation i.d. of AdHu5 expressing PbCSP and were challenged two or eight weeks later. The remaining groups were immunised with heterologous prime-boost regimes using AdHu5 and MVA expressing PbCSP. The time interval in weeks between the two immunisations is indicated in parentheses. All immunisation regimes utilised the AdHu5 vector expressing PbCSP under the control of the long promoter. Mice were challenged i.v. with 10$^3$ P. berghei sporozoites. Blood-stage parasitaemia was monitored daily by Giemsa-stained thin-blood smear from day 5 in challenged mice. Mice are protected given the continued absence of patent blood-stage parasitaemia up until day 21. 33% of mice were protected against challenge following a single immunisation with Ad-PbCSP and infection two weeks later as shown in Table 3.

TABLE 3

| Immunisation Regime | Time Interval between Immunisation and Challenge | No. Mice Protected/ Challenged | % Protection |
|---|---|---|---|
| Ad-PbCSP | 2 weeks | 4/12 | 33% |
| Ad-PbCSP | 8 weeks | 1/6 | 18% |
| Naive | 2 weeks/8 weeks | 0/12 | 0% |
| Ad-MVA PbCSP (2 week prime-boost interval) | 2 weeks | | 66% |
| Ad-MVA PbCSP (8 week prime boost interval) | 2 weeks | | 100% |
| Naïve | 2 weeks | | 0% |

Immunisation with Ad-PbCSP induces a potent CD8$^+$ T cell response against the H-2$^d$ class I-restricted epitope, Pb9 (34). If these mice are boosted with MVA encoding PbCSP eight weeks later, then 100% of mice are refractory to P. berghei sporozoite challenge Table 3 and Ref. (33).

Example 2: Production of Pre-Erythrocytic Human Malaria (P. falciparum) Antigen Vaccines with Human and Simian Adenovirus Vectors Vaccination with pre-erythrocytic vaccines have shown particular promise for tacking the huge global health problem of malaria (1,2) with some efficacy in clinical trials from immunity to this stage of the malaria life cycle directed towards the sporozoite and subsequent intrahepatic schizont (37). The cellular immune response has previously been shown to be important in pre-erythrocytic immunity with CD8$^+$ T cells and IFN-gamma production playing a central role in protection to liver stage malaria (38). The thrombospondin-related adhesion protein (TRAP) is an antigen expressed on the sporozoites which has previously been shown to induce a protective CD8$^+$ T cell responses (39). TRAP has been extensively tested in vaccine clinical trials as a fusion protein with a multiepitope string containing additional B-cell, CD8+ and CD4+ T cell epitopes, known as ME.TRAP (40,41). In humans, FP9-MVA.ME.TRAP prime-boost regimes have been shown to induce CD8+ as well as CD4+ T cell responses that conferred sterile protection in some volunteers (42,43). Adenoviral vectors of the human serotype 5 have previously been used in a *P. yoelii* mouse model of malaria and have shown outstanding immunogenicity and significant protection after just a single dose (44). However, one major limitation preventing the use of this serotype in humans is the ubiquitous presence of AdH5, with frequent childhood infections resulting in seroconversion. It has been reported that nearly all adults have antibodies against AdH5 (45), and 45% to 80% of individuals possess neutralizing antibodies (NAB) to the virus (46). To circumvent the problem of preexisting immunity to AdH5, there has been increased interest in the use of adenoviral serotypes of simian origin that do not circulate at appreciable levels in human populations, with a number of studies demonstrating the ability of these vectors to elicit CD8+ T-cell responses in both mice and nonhuman primate models of SARS (47) and HIV (48, 49).

In this current work, the inventors demonstrate for the first time in a mouse malaria model that with the use of a long intron A containing CMV promoter, as defined above, four simian adenoviral vectors, AdC6, AdC7, AdC9 (also known as C68 (50)), can induce outstanding CD8+ T cell responses often outperforming AdH5. Moreover, there was induction of high levels of sterile protection to a challenge with *P. berghei* after a single vaccination with the vectors. Finally, in conditions of preexisting immunity to AdH5 simian adenoviral vectors still maintained a high degree of protection which was abrogated with the use of human serotype 5.

2.1 Material and Methods

Mice and Immunizations

Female BALB/c mice 4 to 6 week of age were used and immunized intradermally, which has previously been shown to elicit better immunogenicity when compared to other routes e.g. sub-cutaneous, intramuscular (58). MVA.ME.TRAP (MVA) or FP9.ME.TRAP were administered at a dose of 1×10$^6$ or 1×10$^7$ pfu, and adenoviruses at a dose of 1×10$^9$ or 1×10$^{10}$ viral particles (v.p.).

Viral Vectors

All vectors express the transgene ME.TRAP that has been previously described (40,71). The insert ME.TRAP is a hybrid transgene of 2398 bp encoding a protein of 789 aa. The ME string contains the BALB/c H-2K$^d$ epitope Pb9 amongst a number of other B- and T-cell epitopes (72). The simian adenoviral vectors (SAdV) and the AdHu5 vector were constructed with a intron A bearing long CMV promoted as described (73). Construction of the MVA (71) and FP9 (43) has been described earlier.

Ex Vivo IFNγ ELISPOT

ACK-treated splenocytes or PBMCs were cultured for 18-20 hours on IPVH-membrane plates (Millipore) with the immunodominant H-2K$^d$-restricted epitope Pb9 (SYIP-SAEKI; SEQ ID NO: 12) at a final concentration of 1 μg/ml. ELISPOT was performed as previously described (74). To analyze the breadth of the immune response, splenocytes were stimulated with pools of 20-mer peptides overlapping by 10 aa spanning the entire length of TRAP (43,71) as well as a pool of peptides covering the ME string, all at a final concentration of 5 μg/ml.

Intracellular Cytokine Staining

ACK-treated splenocytes were incubated for 5 hours in presence of 1 μg/ml Pb9 and 4 μl/ml Golgi-Plug® (BD). Intracellular cytokine staining (ICS) was performed with BD cytofix/cytoperm Plus® kit according to the manufacturer's instructions. Splenocytes were stained with a suitable combination of fluorochrome-conjugated antibodies, specific for CD8 (clone 53-6.7, eBioscience), IFNγ (clone XMG1.2, eBioscience), CD27 (clone LG.7F9, eBioscience), CD43 (clone 1B11, BD/Pharmingen), CD127 (clone A7R34, eBioscience), IL-2 (clone JES6-5H4, eBioscience), mouse isotype controls IGg2a (eBR2a, eBioscience), CD16/CD32 Fcgamma III/II Receptor (2.4G2, BD/Pharmingen), anti-Granzyme B® (clone GB12, Caltag), IgG1 isotype control (Caltag). When CD62L (clone MEL-14, eBioscience) was used, stimulated cells were incubated with TAPI-2 peptide (Peptides International, USA) at a final concentration of 250 μM to prevent CD62L shedding from the cell surface. For peptide mapping and potency in C57BL/6 mice, splenocytes were stimulated with peptide pools containing 20-mers overlapping by 10, spanning all of the ME-TRAP sequence. The final concentration was 20 μg/ml. CD4 and CD8 responses were tracked by flow cytometry and individual peptides were synthesized after an analysis in the SYF-PEITHI database to predict the immunodominant epitopes. Upon titration, individual peptides were used at a final concentration of 5 μg/ml.

Flow cytometric analyses were performed using a FACSCanto® (BD Biosciences) and data were analyzed with either FACSDiva® (BD) or Flow Jo® (Tree Star) software.

Evaluation of Antigen-Specific CD8+ T-Cell Response by Flow Cytometry

The frequency of IFNγ+ CD8+ T cells was calculated by subtracting the values from the unstimulated control, which never exceeded 0.1% in any of the experiments. The total number of antigen-specific cells was calculated as previously described (53). For the phenotypic makers investigated, each marker was compared to an isotype control.

ELISA

IgG antibodies against the TRAP region were analyzed by ELISA as described previously (43). For this experiment, serum was obtained from groups of at least 3 BALB/c mice after 2 weeks of immunization with individual vectors. Results were reported as a dilution factor needed for a sample in order to reach the O.D. of a naïve serum.

Parasite Challenge

*Plasmodium berghei* (ANKA strain clone 234) sporozoites (spz) were isolated from salivary glands of female *Anopheles stephensi* mosquitoes. Parasites were resuspended in RPMI-1640 medium with each mouse receiving a total of 1,000 spz via the i.v. route. Blood samples were taken on daily basis from day 5 to 20; smears were stained with Giemsa and screened for the presence of schizonts within the red blood cells. Survival was defined as complete absence of parasites in blood.

2.2 Results

Breadth of the Immune Response

Figure 9A:
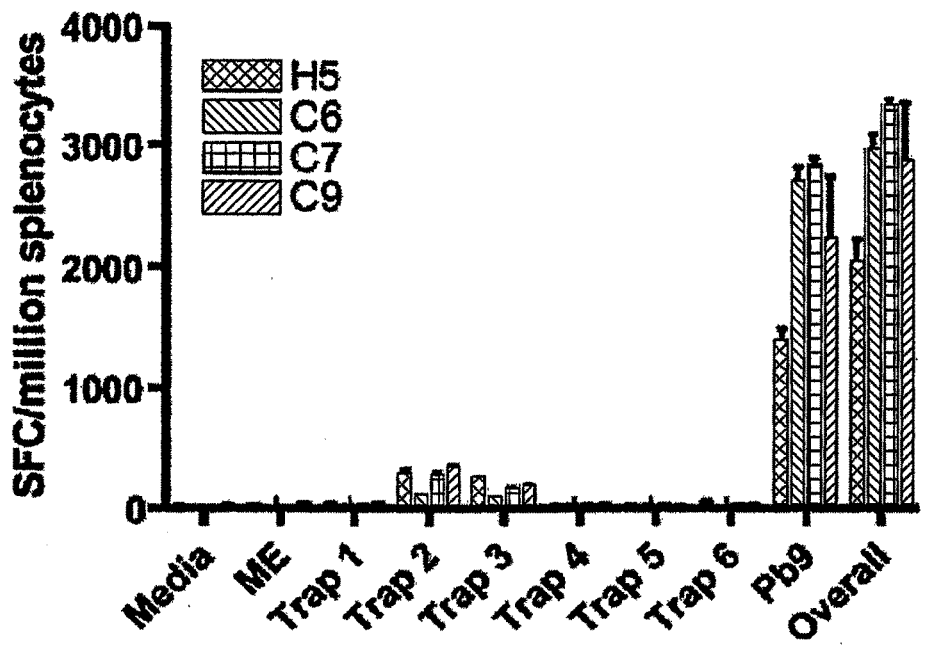
FIG. 9A-FIG. 9D shows immunogenicity to ME.TRAP (FIG. 9A) Breadth of the immune response to ME-TRAP. BALB/c mice were immunized with $1 \times 10^{9}$ vp of adenoviral vectors coding for ME.TRAP. Immune responses were measured 2 weeks later by ELISPOT after stimulation of cells were overlapping peptides covering the whole sequence of the ME-TRAP transgene. Data are mean±s.d. for three mice per group.

The breadth of the immune response to ME.TRAP was analyzed in BALB/c (FIG. 9a) and in C57BL/6 (FIG. 10a) mice by IFNγ ELISPOT. In BALB/c, the predominant response was directed towards the immunodominant H-2K$^d$-restricted epitope Pb9, whereas in C57BL/6 the response was present in three sub-pools: the ME string, TRAP 1 and TRAP 2. Additional analysis with intracellular cytokine staining and the use of SYFPEITHI database allowed the characterization of a CD4 epitope in TRAP 1 (IHLYVNVF- SNNAKEI; SEQ ID NO: 9), a CD8 epitope in TRAP 2 (NVAFNRFLV; SEQ ID NO: 10) and a CD8 epitope in the ME string (DASKNKEKAL; SEQ ID NO: 11).

Kinetics of the Pb9-Specific CD8$^+$ T Cell Response.

Figure 9B:
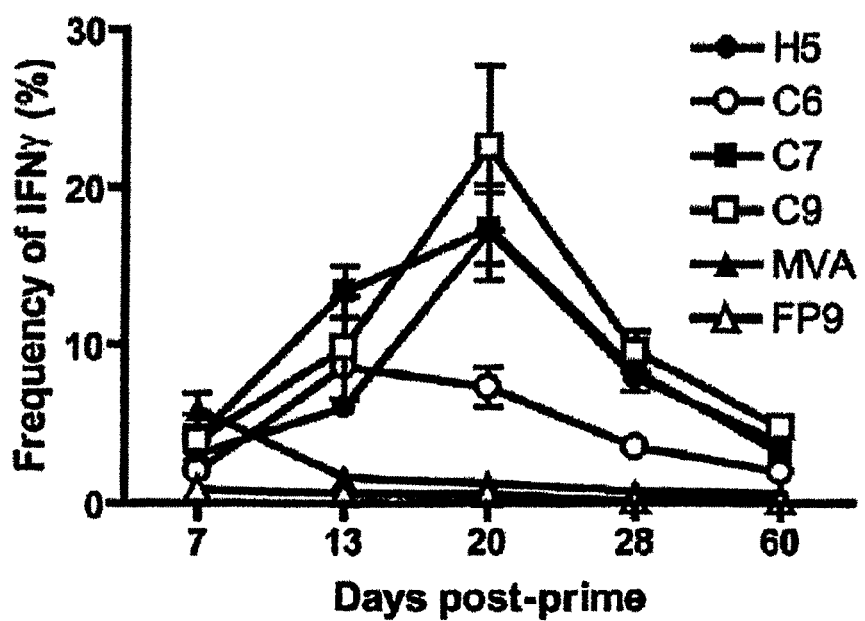
Figure 9C:
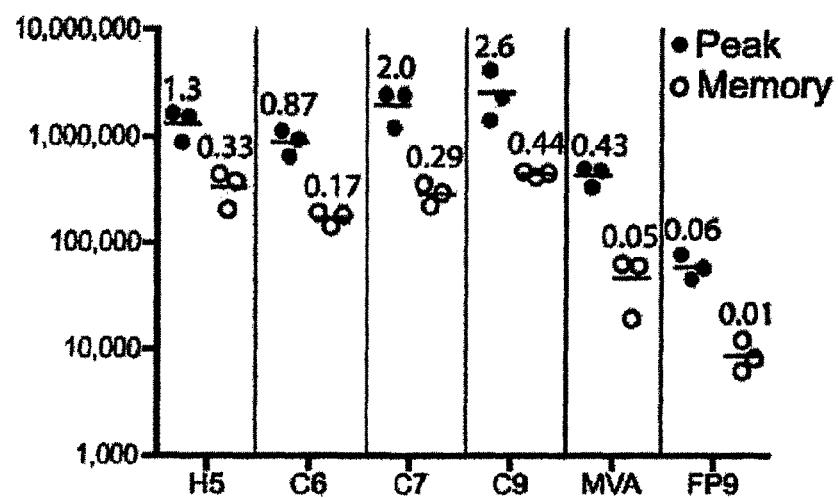
Figure 9D:
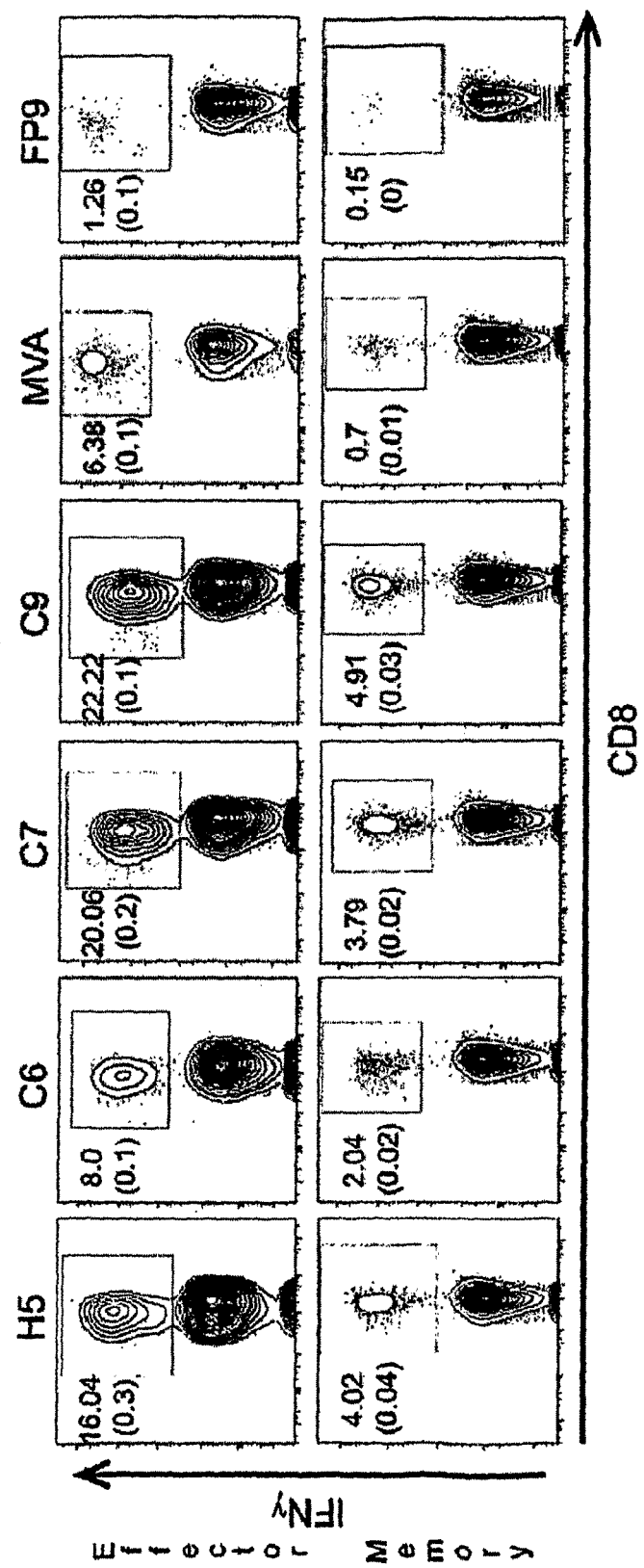

The CD8$^+$ T cell response to Pb9 from all six vectors was investigated in terms of expansion, contraction and generation of memory cells. The simian adenovirus (SAds) AdC7 (C7), AdC9 (C9) elicited the strongest immune responses, followed by AdH5 (H5) (FIG. 9b, 9c, 9d). Of the SAds, AdC6 (C6) was the least potent in terms of IFN-γ production but all Ads induced similar CD8$^+$ T-cell expansion kinetics with a peak response about 20 days post-immunization. On the other hand, the poxviruses MVA and FP9 (which use a non-CMV poxvirus promoter) induced an immune response that peaked one week post vaccination, with a decrease in the frequency of CD8$^+$ IFN-γ$^+$ cells observed as early as the 2 weeks post vaccination. The frequency of IFNγ$^+$ CD8$^+$ T cells at day 60 post-vaccination was highest in mice that were vaccinated with an adenovirus, this was most apparent in mice immunized with either C9 or H5. Thus, all adenoviral vectors share similar characteristics in terms of both strength and kinetics of the CD8$^+$ T cell response, with profound differences in the expansion and contraction kinetics observed between adenoviral and poxviral vectors.

Effector CD8$^+$ T-Cell Response.

Figure 11A:
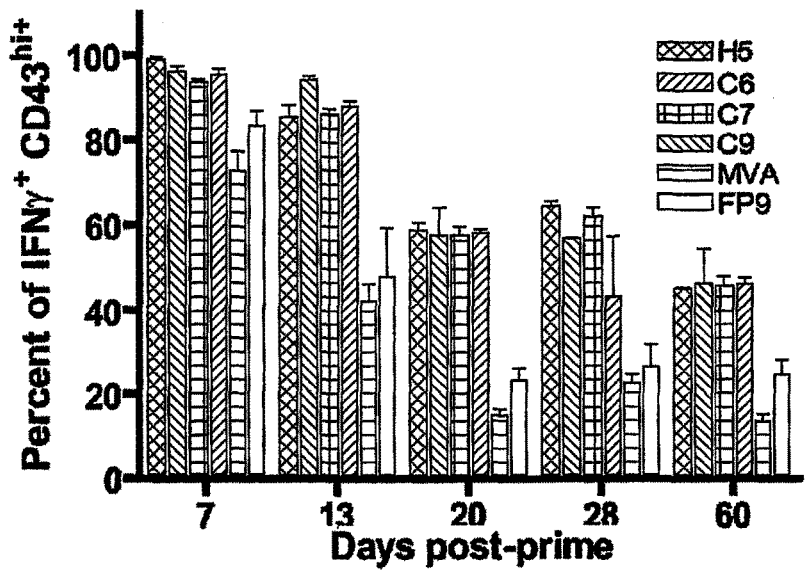
FIG. 11A-FIG. 11C shows acquisition of effector phenotype and cytolytic functions by CD8$^+$ T cells at different intervals post-vaccination.
Figure 11B:
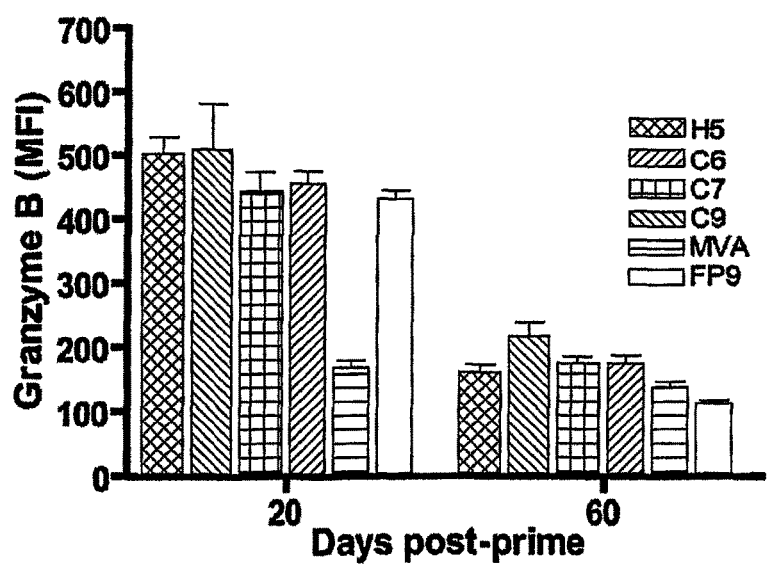
Figure 11C:
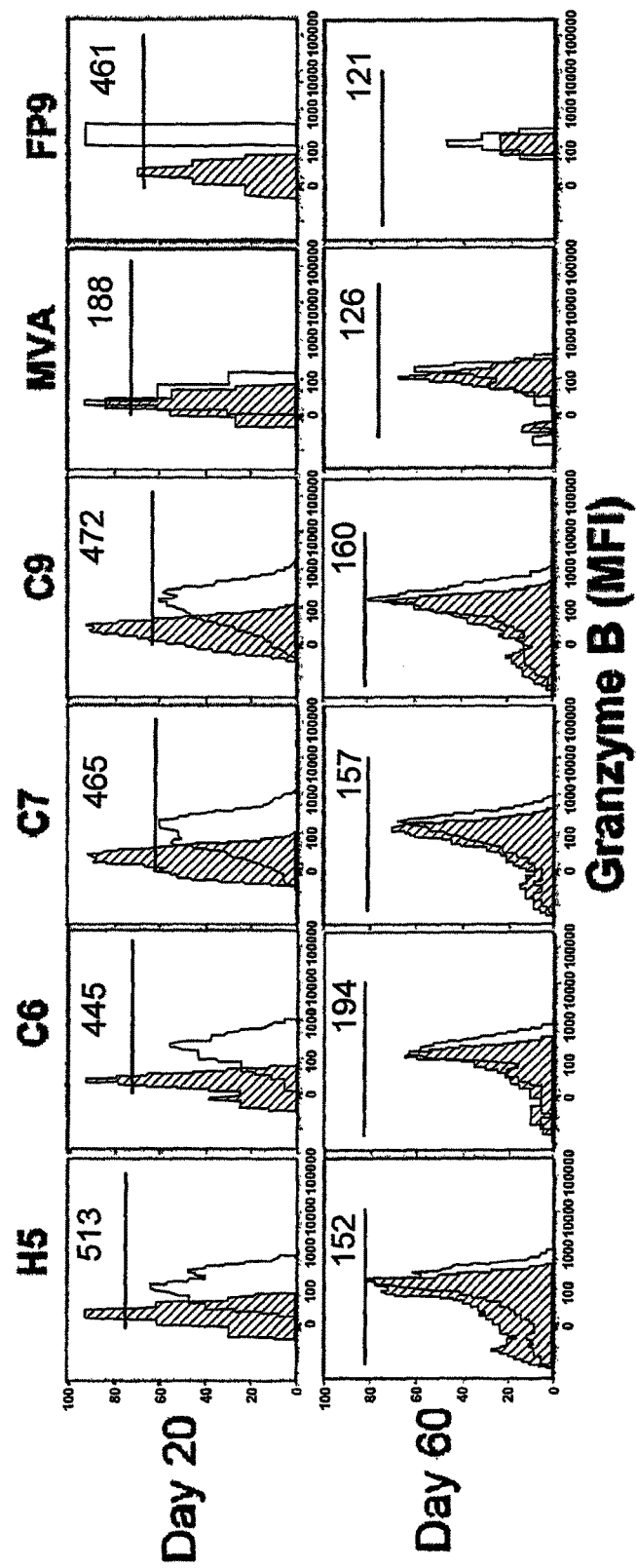
Figure 12A:
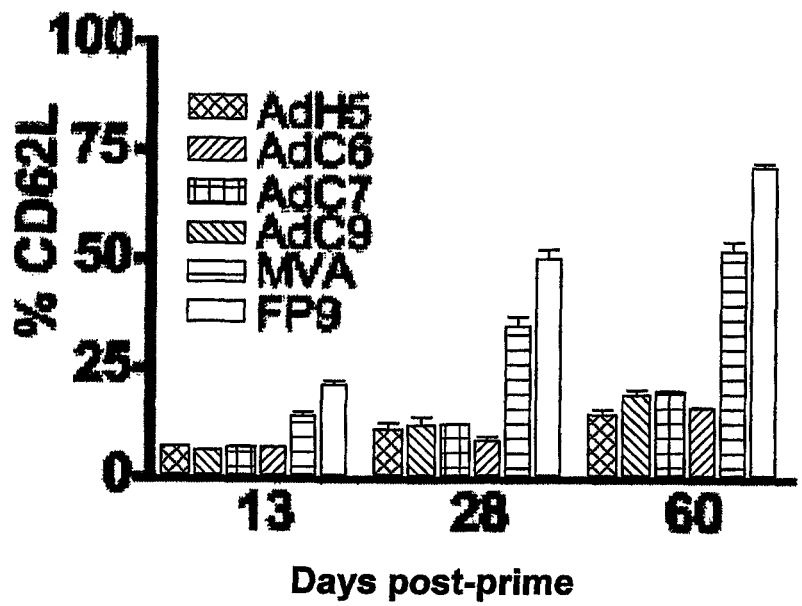
FIG. 12A-FIG. 12D shows analysis of the memory response by phenotypic markers. BALB/c mice were immunized as described in FIG. 1. Splenocytes were co-stained for CD8, IFNgamma$^+$ and (FIG. 12A) CD62L, (FIG. 12B) CD127, (FIG. 12C) IL-2 and (FIG. 12D) CD27. Bars show percentages of cells within the IFNgamma$^+$ compartment. Data are mean±s.e.m. for three mice per group.
Figure 12B:
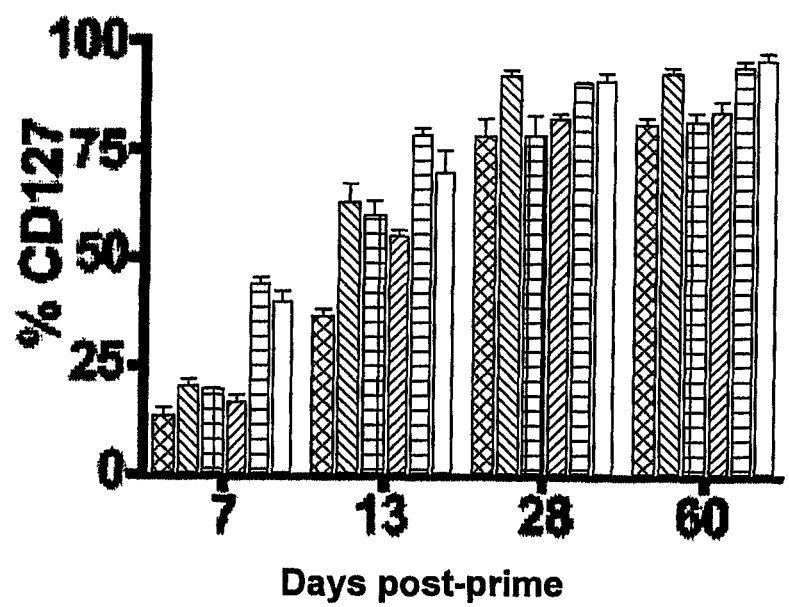
Figure 12C:
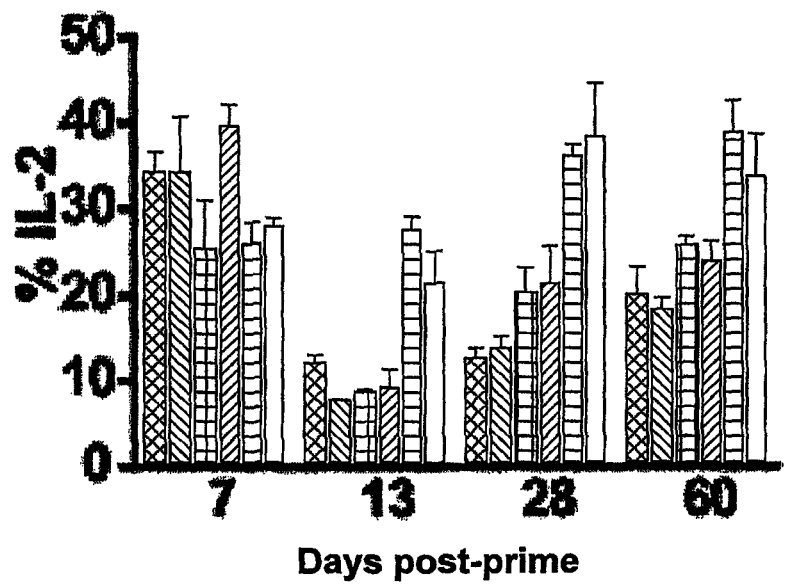
Figure 12D:
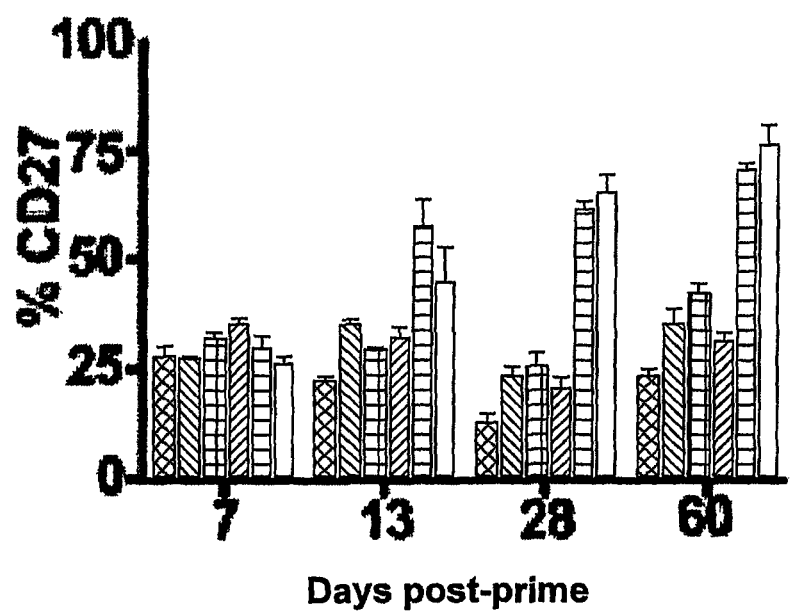

Due to the short interval between infection and progression to disease, effector CD8$^+$ T cells can play an important role in protection against malaria. Therefore, the acquisition of effector functions determined by the expression of a number of phenotypic markers, CD43 and Granzyme B, was investigated. CD43 expression has previously been shown to be upregulated during the effector phase of the CD8 response (51) while the cytolytic effector molecule Granzyme B (GrB), is highly expressed in CD8$^+$ T effector cells, with lower levels observed in $T_{EM}$ and $T_{CM}$ (52), and it is one of the main mechanisms that CTLs use to kill infected cells. In general, adenoviral vectors induced a significantly higher percentage of CD8$^+$IFN-gamma$^+$CD43$^{hi}$ over the entire course of the immune response when compared to the poxviral vectors. Interestingly, poxviral vectors induced a low percentage of CD43$^{hi}$ as early as one week post-vaccination, suggesting a more rapid transition towards the memory phase especially with MVA. At day 60 post-prime, mice immunized with the adenoviral vectors still retained a significantly higher percentage of CD43$^{hi}$ when compared to the poxviral counterpart (FIG. 11a). In addition, levels of GrB were significantly lower in the MVA group at day 20 (p<0.001), and at day 60 both poxviral vectors were significantly lower than C6 (p<0.05) (FIG. 11b, 11c). These results demonstrate that in response to all four adenoviruses there was a full development of an effector response with preservation of cytolytic molecules for long periods of time, indicative of the presence of $T_{EM}$ cells (52).

Functional and Phenotypic Memory Markers of Pb9-Specific CD8$^+$ T Cells

One of the main objectives of any vaccination regime is the generation of memory CD8$^+$ T cells that are capable of persisting in vivo and expanding rapidly upon encounter with pathogens thus affording protection. To date a number of different molecules have been suggested to correspond to different sub-types of memory cells (53, 54). In this current study the inventors chose to investigate a number of these molecules to determine whether individual vectors induced different memory cells populations. During the early phase of the response, CD8$^+$ IFN-γ$^+$ cells generated in response to either FP9 or MVA displayed a CD62L$^{hi}$, CD127$^{hi}$ and produced IL-2, confirming the rapid transition towards a $T_{CM}$ phenotype. Conversely, the adenoviral vectors did not induce a central memory CD8$^+$ T phenotype, even by day 60, with the majority of CD8$^+$IFN-γ$^+$ cells displaying predominantly an effector memory phenotype (CD62L$^{lo}$, CD127$^{hi}$, and low percentage of IL-2 producing cells) (FIG. 12a-d). Interestingly, CD27 remained low in mice vaccinated with adenoviral vectors, whereas the percentage of CD277 cells increased over time in response to the poxviral vectors. Since CD8$^+$ CD27$^-$ cells are maintained in response to persistent antigenic stimulation (55), this may suggest that prolonged antigen stimulation was occurring in response to the adenoviruses. In summary, these results demonstrate that vaccination with adenoviral vectors induces predominantly a $T_{EM}$ response, as evidenced by a CD62L$^{lo}$, CD127$^+$, IL-2$^{low}$ phenotype in addition to the relative high percentage of CD43$^{hi}$ cells as well as higher levels of cytolytic molecules 60 days post-prime.

Survival Following a Challenge with P. berghei.

To assess the level of protection afforded by these different vectors, mice were challenged with P. berghei as shown in Table 1. BALE/c mice were immunized with adenoviral ($1×10^{10}$ vp) and poxviral vectors ($1×10^7$ pfu) and then challenged 14 days (n=12) and 60 days later (n=6) by i.v. administration of 1000 sporozoites of Plasmodium berghei. Preexisting immunity to AdH5 was analyzed after injecting groups of 6 BALB/c mice with $5×10^5$ v.p. of AdH5 coding for an unrelated transgene (Ag85.A). 30 days later, the same mice were immunized with $1×10^{10}$ v.p. per mouse of AdH5, C6, C7 and C9 coding for ME.TRAP. Mice were challenged 14 days after the last immunization. Numbers represent the percentage of animals that survived the challenge. Statistical differences are indicated as: * p<0.05,  p<0.01, * p<0.001, and show comparison of individual regimes with the naïve control.

TABLE 1

| Vector | Day 14 (n = 12) % | Day 60 (n = 6) % | Pre-existing immunity to H5 (day 14) (n = 6) % |
|---|---|---|---|
| H5 | 83*** | 0 | 0 |
| C6 | 67** | 0 | 17 |
| C7 | 83*** | 50* | 33** |
| C9 | 92*** | 17 | 50* |
| MVA | 0 | 0 | n.t. |
| FP9 | 0 | 0 | n.t. |
| Naive | 0 | 0 | 0 |

In conditions with no previous immunity to AdH5 (day 14), C9 provided the best protection (92%), this was followed by C7, H5 (83%) and finally C6 (67%), all of them significantly higher than the naïve control group (0%, p<0.001). No protection was afforded by MVA or FP9 at the same time point. At day 60 post-prime, significant protection was achieved with C7 (50%) and C9 (17%) but no protection was observed when mice were immunised with either H5 or C6. The ability of these vectors to confer protection in presence of preexisting immunity to AdH5, which would mimic a human situation where at least 45% of the population is expected to have NABs to AdH5, was also assessed in this study. Mice were initially immunised with AdH5 containing an unrelated insert (Antigen 85A from Mycobacterium tuberculosis) which was followed 4 weeks later by the Ads vectors coding for ME.TRAP. In the presence of pre-existing AdH5 immunity, immunization with H5 gave no protection while C9 gave the best protection (50%), this was followed by C7 (33%) and C6 (17%). Both, C9 and C7 were significantly higher than H5 and the naïve controls ($p<0.05$ and $p<0.01$, respectively).

T-Cell Responses to Pf Trap

Figure 10A:
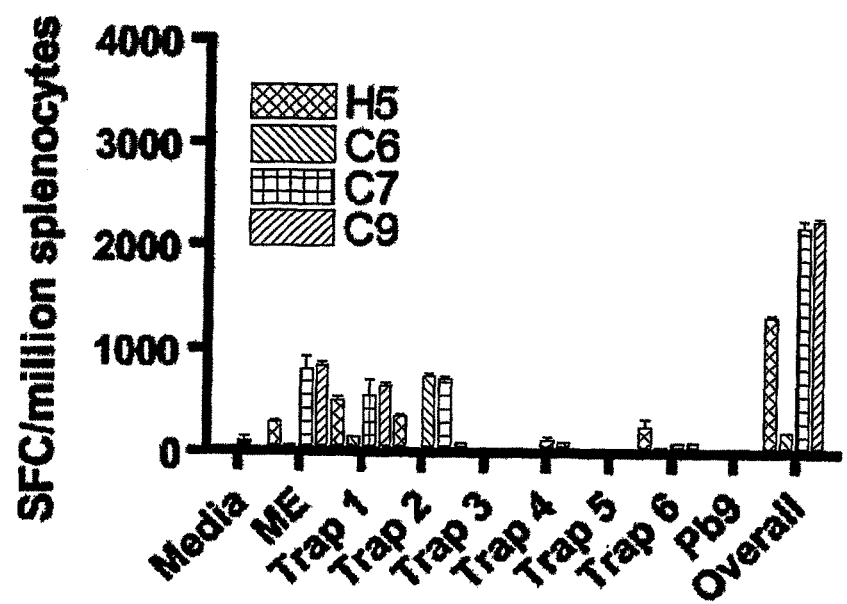
FIG. 10A-FIG. 10B shows immunogenicity to ME.TRAP in C57BL/6 mice.
Figure 10B:
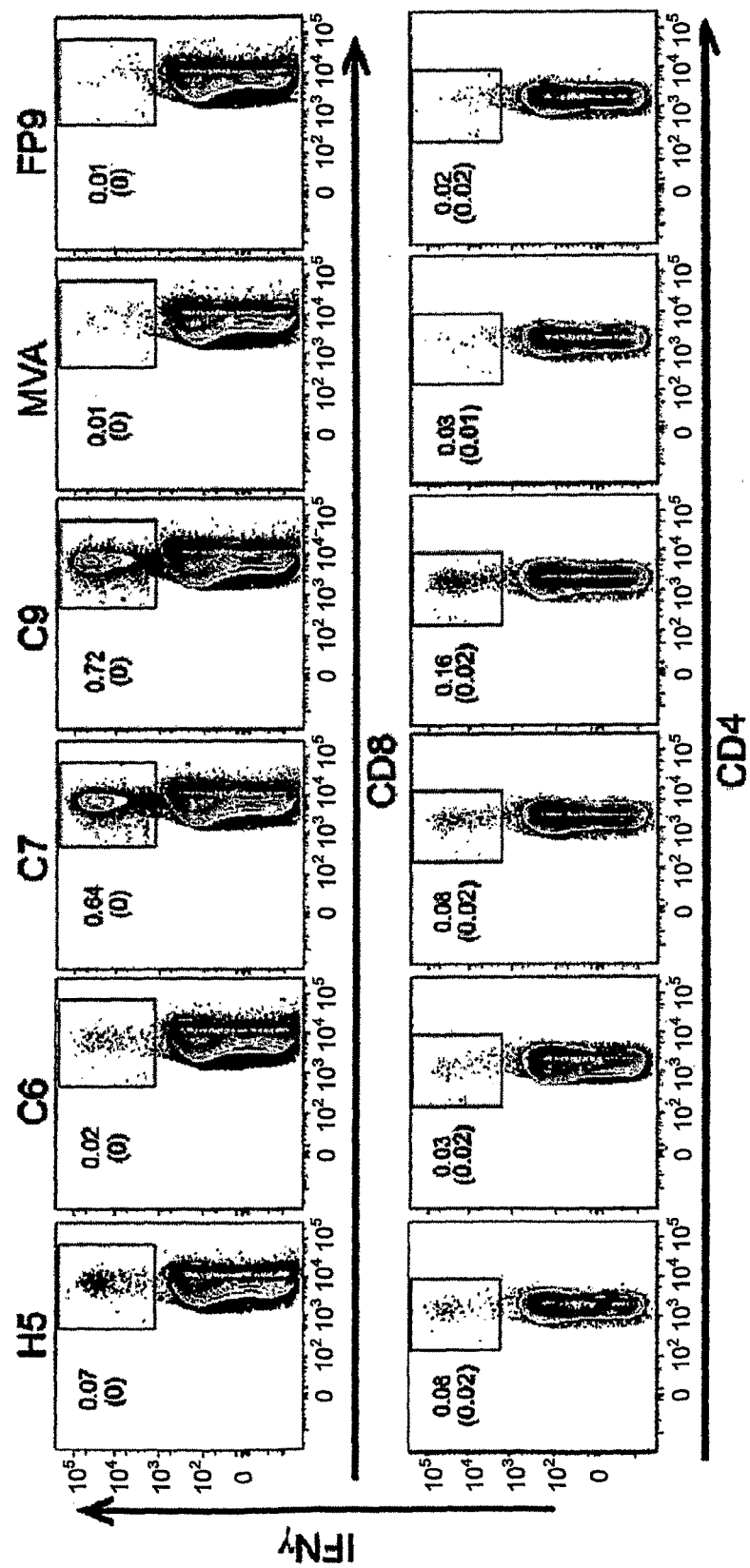

To determine that immune responses are elicited by the *P. falciparum* TRAP within the ME-TRAP transgene, immunogenicity was analyzed by intracellular cytokine staining in splenocytes of C57BL/6 mice upon vaccination with all vectors. The ELISpot technique showed an immune response elicited by three sub-pools (FIG. 10a). Flow cytometric analysis revealed the presence of one CD4 and one CD8 epitope in the TRAP sequence and a CD8 epitope in the ME string. Additional analysis using the SYFPEITHI database allowed the identification of the optimal peptide sequences for synthesis purposes (56). A similar trend in terms of potency of the CD4$^+$- and CD8$^+$-T cell responses was observed with respect to the Pb9 responses. C9 elicited the most potent TRAP T-cell responses, followed by C7, H5 and finally C6. Both poxviral vectors induced a more modest immune response measured on week 3 post-vaccination (FIG. 10b).

Antibodies to Trap

Figure 13:
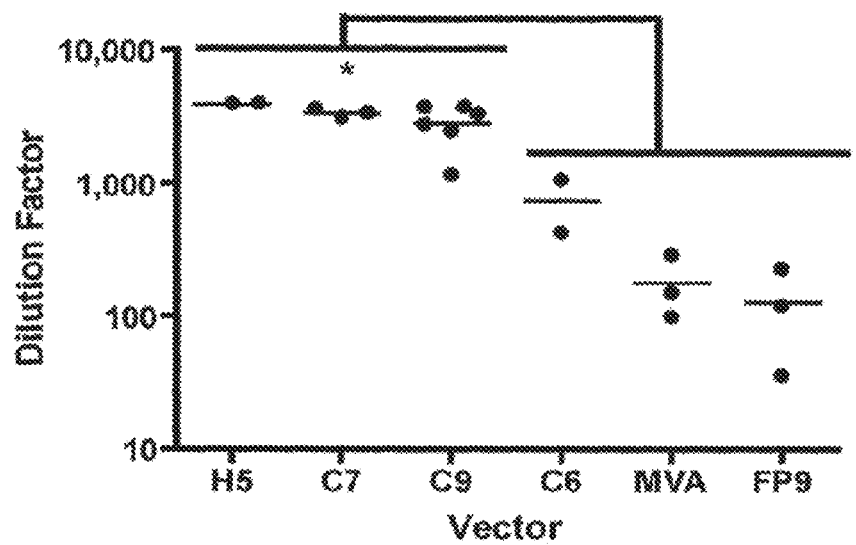
FIG. 13 shows analysis of the antibody responses to Pf TRAP. IgG antibodies against the TRAP region were analyzed by ELISA in serum from groups of at least 3 BALB/c mice after 2 weeks of immunization with individual vectors. Results were reported as a dilution factor needed for a sample in order to reach the O.D. of a naïve serum.

Induction of a TRAP-specific B-cell response by the vectors was assessed in sera from vaccinated mice. All of the adenoviral vectors were able to induce high levels of IgG antibodies against the TRAP region, whereas the poxviral vectors elicited low antibody levels. The strongest responses were achieved by AdH5 (O.D. $\bar{x}=3930\pm14$), followed by AdC7 ($\bar{x}=3358\pm256$), AdC9 ($\bar{x}=2862\pm979$), AdC6 ($\bar{x}=739\pm452$); whereas MVA ($\bar{x}=178\pm98$) and FP9 ($\bar{x}=126\pm95$) induced minimal levels of antibodies (FIG. 13). Values for AdH5, AdC7 and AdC9 were significantly higher than the rest of the group.

2.3 Discussion

There is increasing evidence that T-cell responses may be a critical requirement for protection against diseases such as malaria, AIDS, tuberculosis and cancer. CD8$^+$ T cells have previously been shown to play a central role in protection to the liver stage of malaria infection (57). A number of sub-unit vaccines, in the form of naked DNA and viral vectors, have been shown to induce strong CD8$^+$ T cell responses in mice (44), providing protection against malaria.

Adenoviral vectors of the human serotype 5 (AdH5) have been tested in mice as vaccine candidates for a variety of infectious diseases (44, 58, 59). These vectors have displayed outstanding CD8$^+$ T-cell immunogenicity in a prime-boost regime in combination with poxviral vectors and have conferred significant protection. However, in the only previous study of adenoviral vectors in the *P. berghei* model protection by homologous AdH5 immunization was minimal (58). Due to the ubiquitous presence of AdH5, a high percentage of humans develop antibodies that render the vaccine ineffective. To circumvent this problem, adenoviral vectors have been engineered from chimpanzee serotypes that do not circulate in humans. Previous studies have shown the ability of the chimpanzee adenovirus to elicit potent B- and CD8$^+$ T-cell-mediated immune responses in models of rabies (50), SARS (47) and HIV (49), as a prime or heterologous prime-boost regimes in mice and primates.

The use of three chimpanzee adenoviral vectors, AdC6, AdC7 and AdC9 as a pre-erythrocytic malaria vaccine has been possible using an intron A bearing long promoter. The inventors have compared these vectors to AdH5 also expressing a long promoter and two poxviral vectors that have been widely used in human clinical trials, MVA and FP9.

The adenoviral vectors elicited the most potent CD8$^+$ T cell responses, which peaked at week 3 yet maintained a high frequency of Pb9 specific cells even out to 60 days post-prime. In contrast, poxviral vectors peaked around the first week and then contracted rapidly. Upon analysis of a number of phenotypic markers, such as CD43 and GrB, Ads were shown to induce a potent effector population of cells which was significantly lower when mice were immunized with either of the poxviral vectors. In addition, MVA was shown to induce a lower level of GrB suggesting an overall reduced level of cytotolytic activity. Thus, adenoviral vectors were able to induce a sustained CD8$^+$ T-cell effector response that was retained at high levels for at least 60 days after priming. Additional phenotypic markers showed that poxviral vectors induced the generation of a predominantly CD62L$^+$, CD127$^+$ CD8$^+$ T cells, whereas the predominant phenotype of CD8$^+$ T cells in response to the Ad vectors was CD62L$^{dull/-}$, CD127$^+$ over a long period of time. Based on expression of these markers, three different subsets of Ag-specific CD8$^+$ T cells can be identified: effector T cells $T_E$ (CD62L$^-$CD127$^-$); effector memory T cells $T_{EM}$ (CD62L$^-$ CD127$^+$) and central memory T cells $T_{CM}$ (CD62L$^+$ CD127$^+$) (60).

Antibodies to the TRAP region were also assessed after vaccination of BALB/c mice with each vector. Potency in terms of the B-cell response correlated well with the magnitude of CD8$^+$ T cell responses. Protection against *P. berghei* in this system relies on CD8$^+$ T-cell responses directed towards an immunodominant epitope, Pb9. Antibodies to TRAP would not play a role in protection due to the fact that the TRAP sequence is derived from *P. falciparum*. However, the presence of antibodies could add an extra benefit to improve protection in human infections with *P. falciparum*.

The inventors show that the simian adenoviral vectors using a long promoter elicited potent CD8$^+$ T cell responses that are important in protection in a preerythrocytic mouse model of malaria. In contrast to rare human adenovirus serotypes, such as AdHu35 (70), the immunogenicity and efficacy of these simian vectors is as great or greater than AdH5. Comparison of the adenoviral vectors to two poxviral vectors, FP9 and MVA, demonstrated that the Ads were able to sustain a high number of CD8$^+$ T cells over a long period of time that subsequently resulted in the generation of a high number of $T_{EM}$ cells. Conversely, immunization with either of the poxviral vectors induced a high proportion of $T_{CM}$ cells very early after immunization. In addition, all simian adenoviral vectors induced outstanding levels of protection during the effector phase of the response in absence and presence of preexisting immunity to AdH5, with protection being maintained for a long period of time with a number of the vectors. These data demonstrate for the first time that a single dose of a subunit vaccine is able to elicit protection to *P. berghei* and highlights the potential of the simian adenoviral vectors for a future application as a malaria vaccine in humans.

Example 3: Blood Stage Vaccines Against *P. falciparum* Malaria

Based on the findings of Example 1 demonstrating the surprising ability of a Ad-MVA heterologous prime-boost immunisation regime to induce strong protective immunity to blood stage malaria in a *P. yoelii* murine malaria model, the inventors proceeded to generate adenovirus and MVA vectors encoding sequences from the MSP-1 gene of the human malaria parasite P. falciparum. This gene is dimorphic with two prevalence sequence types. It has a well studied block structure that allows the identification of conserved and variable blocks.

The PfM117 insert (see SEQ ID NO. 1) has been designed as a useful insert for immunisation. It comprises conserved sequence blocks 1, 3, 5 and 12 at the N terminus of a fusion protein followed by both copies of the important 33kd fragment and at the C terminus of the protein the relatively conserved 19Kd fragment. The 33Kd fragment is a well studied immunogenic component of the MSP1 antigen that is known to contain T cell epitopes. It is however dimorphic with substantial sequence divergence between the two major types, often denoted by the labels Wellcome and MAD20 referring to the parasite strains that early sequences were derived from (Miller L. H. et al. Mol Biochem Parasitol. 1993, 59(1):1-14). In PfM117 the Wellcome strain sequence is found N-terminal to the MAD20 strain sequence, and immediately C-terminal to these is the 19Kd sequence. This latter fragment is highly but not completely conserved amongst P. falciparum parasite strains and is known to be the target of protective antibodies. However some of these protective antibodies can be inhibited in their protective action by so called blocking antibodies (Uthaipaibul et al. J Mol Biol. 2001, 307 (5):1381-94.) Uthaipaibul et al. (2001) describe amino acid changes that can be made in the canonical sequence of the 19Kd fragment that allow inhibitory antibodies to act preferentially over blocking antibodies, thereby increasing the likelihood that antibodies induced to this fragment should be protective. Therefore within this 19 Kd fragment three amino acids have been altered to avoid blocking antibody binding (Uthaipaibul et al. (2001)).

The PfM128 insert (see SEQ ID NO. 3), is identical to the PfM117 sequence with an additional copy of a 19Kd fragment inserted between the two 33Kd fragments. This additional 19Kd fragment allows an alternative allelic sequence of that fragment to be expressed by this construct potentially broadening the range of protective antibodies or T cells that might be induced by PfM128 compared to PfM117.

Figure 14:
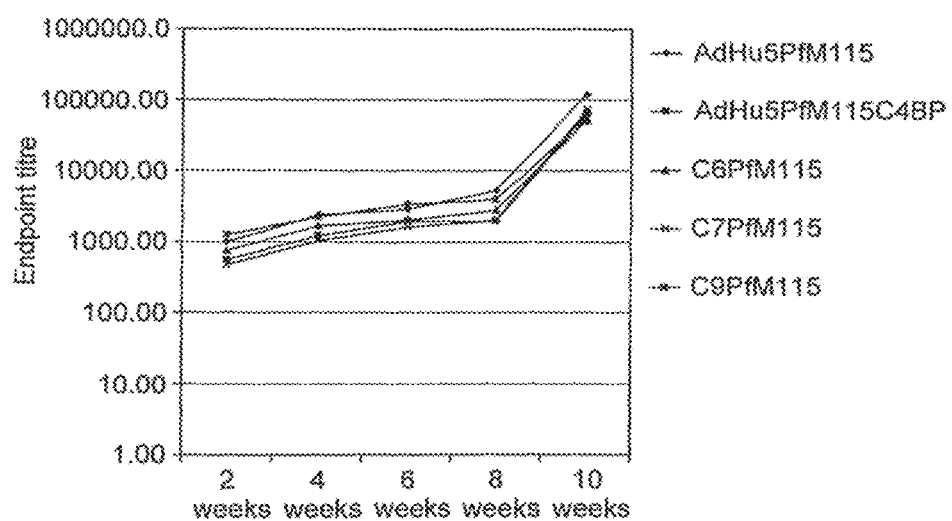
FIG. 14 shows immunogenicity of various adenoviruses encoding the PfM115 insert in BALB/c mice.
After a single immunization intradermally ($5 \times 10^{10}$ vp) with the various adenoviral vectors at week 0 good antibody levels were detected to the 19Kd fragment of PfMSP1 at 2 weeks in all mice and these titres increased up to week 8 when all mice were administered an MVA encoding the same insert, leading to an further increase in antibody titres. The simian adenoviral vectors appears similar in immunogenicity to the AdHu5 vector. The AdHu5PfM115C4 bp encodes an additional C-terminal core sequence from the complement protein C4 bp.

We also constructed an additional insert "PfM115" that is very similar to the PfM117 sequence in that it comprises conserved sequence blocks 1, 3, 5 and 12 at the N terminus of the PfMSP1 fusion protein followed by both copies of the important 33kd fragment and at the C terminus of the protein the relatively conserved 19Kd fragment. However there are some minor sequences differences at the end of the 33Kd fragments compared to the PfM117 corrected sequence. The PfM115 sequence was used to generate recombinant vectors of the C6, C7, C9 and AdHu5 serotypes (strain notation as in example 2) using again the intron A containing long promoter. Good vector genetic stability was observed. Potency as measured by antibody induction (FIG. 14) was excellent. In addition both CD4 and CD8 T cell responses were induced to peptide pools comprising the entire insert sequence of PfM115. Boosting with an MVA vector encoding the same insert led to enhanced antibody and T cell responses.

A widely used in vitro assay to predict the likely efficacy of blood stage vaccines against P. falciparum is the Growth Inhibitory Activity (GIA) assay (Bergmann-Leitner et al Am J Trop Med Hyg. 2006, 75:437-42; Malkin et al. Infect Immun. 2005, 73:3677-85.) This in vitro assay quantifies the % growth inhibition of blood-stage P. falciparum malaria parasites when cultured in the presence of test and control serum. A parasite enzymatic reaction is used to quantify parasite growth following the 40 hour time period of the assay. It is hoped that animals immunised with Candidate blood-stage malaria vaccines will develop protective antibody responses. Serum from these animals can thus be screened using this assay for their ability to inhibit parasite growth. Considerable efforts have been made to standardise this assay, particularly by the NIH laboratory of C. Long. Mice were immunised with the AdHu5-PfM115 insert and boosted with the corresponding MVA construct. Sera taken at a terminal bleed showed 46-52% GIA, as measured by the C. Long lab, a level that represents substantial inhibition of the growth of blood stage parasites (Bergmann-Leitner et al Am J Trop Med Hyg. 2006, 75:437-42). This result suggests that a corresponding immunisation regime used in humans will show protective efficacy.

To try to increase further the immunogenicity and likely protective efficacy of adenoviral vectored vaccines the AdHu5-PfM115 vectored vaccines was coadminstered as a mixture with the CpG sequence 1826 (Brunner et al. J Immunol. 2000, 165:6278-86). CpGs have been well studied as adjuvants for protein-based but not for vectored vaccines (Daubenberger C A, Current Opinion in Molecular Therapy 2007; 9:45-52). One previous study of a CpG sequence co-administered with an adenovirus vaccine encoding a tumour antigen PSA led to lower T cell immunogenicity than when administered without the CpG (Lubaroff et al. Vaccine 2006, 24:6155-62). However, coadministration of the 1826 CpG oligonucleotide with the AdHu5-PfM115 vaccine led to increased CD4 and CD8 T cell responses as measured by flow cytometry (FIG. 15). This suggests that coadministration of CpG oligonucleotides with certain viral vectors, including heterologous long promoter adenoviral vectors, may lead to enhanced T cell immunogenicity for a variety of antigenic inserts.

REFERENCES

1. Fauquet, C., International Committee on Taxonomy of Viruses, and International Union of Microbiological Societies. Virology Division. 2005. *Virus taxonomy: classification and nomenclature of viruses: eighth report of the International Committee on Taxonomy of Viruses.* Elsevier Academic Press, San Diego; London.
2. Rowe, W. P., R. J. Huebner, L. K. Gilmore, R. H. Parrott, and T. G. Ward. 1953. Isolation of a cytopathogenic agent from human adenoids undergoing spontaneous degeneration in tissue culture. *Proc Soc Exp Biol Med* 84:570.
3. Tatsis, N., and H. C. Ertl. 2004. Adenoviruses as vaccine vectors. *Mol Ther* 10:616.
4. Bergelson, J. M., J. A. Cunningham, G. Droguett, E. A. Kurt-Jones, A. Krithivas, J. S. Hong, M. S. Horwitz, R. L. Crowell, and R. W. Finberg. 1997. Isolation of a common receptor for Coxsackie B viruses and adenoviruses 2 and 5. *Science* 275:1320.
5. Wickham, T. J., P. Mathias, D. A. Cheresh, and G. R. Nemerow. 1993. Integrins alpha v beta 3 and alpha v beta 5 promote adenovirus internalization but not virus attachment. *Cell* 73:309.
6. Gaggar, A., D. M. Shayakhmetov, and A. Lieber. 2003. CD46 is a cellular receptor for group B adenoviruses. *Nat Med* 9:1408.
7. Short, J. J., A. V. Pereboev, Y. Kawakami, C. Vasu, M. J. Holterman, and D. T. Curiel. 2004. Adenovirus serotype 3 utilizes CD80 (B7.1) and CD86 (B7.2) as cellular attachment receptors. *Virology* 322:349.

8. Pham, T. T., J. L. Burchette, Jr., and L. P. Hale. 2003. Fatal disseminated adenovirus infections in immunocompromised patients. *Am J Clin Pathol* 120:575.
9. Kim, Y. J., J. Y. Hong, H. J. Lee, S. H. Shin, Y. K. Kim, T. Inada, M. Hashido, and P. A. Piedra. 2003. Genome type analysis of adenovirus types 3 and 7 isolated during successive outbreaks of lower respiratory tract infections in children. *J Clin Microbiol* 41:4594.
10. Xiang, Z. Q., Y. Yang, J. M. Wilson, and H. C. Ertl. 1996. A replication-defective human adenovirus recombinant serves as a highly efficacious vaccine carrier. *Virology* 219:220.
11. Ghosh-Choudhury, G., Y. Haj-Ahmad, P. Brinkley, J. Rudy, and F. L. Graham. 1986. Human adenovirus cloning vectors based on infectious bacterial plasmids. *Gene* 50:161.
12. Graham, F. L., and L. Prevec. 1995. Methods for construction of adenovirus vectors. *Mol Biotechnol* 3:207.
13. Fallaux, F. J., A. Bout, I. van der Velde, D. J. van den Wollenberg, K. M. Hehir, J. Keegan, C. Auger, S. J. Cramer, H. van Ormondt, A. J. van der Eb, D. Valerio, and R. C. Hoeben. 1998. New helper cells and matched early region 1-deleted adenovirus vectors prevent generation of replication-competent adenoviruses. *Hum Gene Ther* 9:1909.
14. Ophorst, O. J., K. Radosevic, M. J. Havenga, M. G. Pau, L. Holterman, B. Berkhout, J. Goudsmit, and M. Tsuji. 2006. Immunogenicity and protection of a recombinant human adenovirus serotype 35-based malaria vaccine against *Plasmodium yoelii* in mice. *Infect Immun* 74:313.
15. Rodrigues, E. G., F. Zavala, D. Eichinger, J. M. Wilson, and M. Tsuji. 1997. Single immunizing dose of recombinant adenovirus efficiently induces CD8+ T cell-mediated protective immunity against malaria. *J Immunol* 158:1268.
16. Shiver, J. W., T. M. Fu, L. Chen, D. R. Casimiro, M. E. Davies, R. K. Evans, Z. Q. Zhang, A. J. Simon, W. L. Trigona, S. A. Dubey, L. Huang, V. A. Harris, R. S. Long, X. Liang, L. Handt, W. A. Schleif, L. Zhu, D. C. Freed, N. V. Persaud, L. Guan, K. S. Punt, A. Tang, M. Chen, K. A. Wilson, K. B. Collins, G. J. Heidecker, V. R. Fernandez, H. C. Perry, J. G. Joyce, K. M. Grimm, J. C. Cook, P. M. Keller, D. S. Kresock, H. Mach, R. D. Troutman, L. A. Isopi, D. M. Williams, Z. Xu, K. E. Bohannon, D. B. Volkin, D. C. Montefiori, A. Miura, G. R. Krivulka, M. A. Lifton, M. J. Kuroda, J. E. Schmitz, N. L. Letvin, M. J. Caulfield, A. J. Bett, R. Youil, D. C. Kaslow, and E. A. Emini. 2002. Replication-incompetent adenoviral vaccine vector elicits effective anti-immunodeficiency-virus immunity. *Nature* 415:331.
17. Sullivan, N. J., T. W. Geisbert, J. B. Geisbert, L. Xu, Z. Y. Yang, M. Roederer, R. A. Koup, P. B. Jahrling, and G. J. Nabel. 2003. Accelerated vaccination for Ebola virus haemorrhagic fever in non-human primates. *Nature* 424:681.
18. Nwanegbo, E., E. Vardas, W. Gao, H. Whittle, H. Sun, D. Rowe, P. D. Robbins, and A. Gambotto. 2004. Prevalence of neutralizing antibodies to adenoviral serotypes 5 and 35 in the adult populations of The Gambia, South Africa, and the United States. *Clin Diagn Lab Immunol* 11:351.
19. Farina, S. F., G. P. Gao, Z. Q. Xiang, J. J. Rux, R. M. Burnett, M. R. Alvira, J. Marsh, H. C. Ertl, and J. M. Wilson. 2001. Replication-defective vector based on a chimpanzee adenovirus. *J Virol* 75:11603.
20. Tatsis, N., L. Tesema, E. R. Robinson, W. Giles-Davis, K. McCoy, G. P. Gao, J. M. Wilson, and H. C. Ertl. 2006. Chimpanzee-origin adenovirus vectors as vaccine carriers. *Gene Ther* 13:421.
21. Saito, I., Y. Oya, K. Yamamoto, T. Yuasa, and H. Shimojo. 1985. Construction of nondefective adenovirus type 5 bearing a 2.8-kilobase hepatitis B virus DNA near the right end of its genome. *J Virol* 54:711.
22. Thomsen, D. R., R. M. Stenberg, W. F. Goins, and M. F. Stinski. 1984. Promoter-regulatory region of the major immediate early gene of human cytomegalovirus. *Proc Natl Acad Sci USA* 81:659.
23. Galvin, T. A., J. Muller, and A. S. Khan. 2000. Effect of different promoters on immune responses elicited by HIV-1 gag/env multigenic DNA vaccine in Macaca mulatta and Macaca nemestrina. *Vaccine* 18:2566.
24. Chapman, B. S., R. M. Thayer, K. A. Vincent, and N. L. Haigwood. 1991. Effect of intron A from human cytomegalovirus (Towne) immediate-early gene on heterologous expression in mammalian cells. *Nucleic Acids Res* 19:3979.
25. Xu, Z. L., H. Mizuguchi, A. Ishii-Watabe, E. Uchida, T. Mayumi, and T. Hayakawa. 2001. Optimization of transcriptional regulatory elements for constructing plasmid vectors. *Gene* 272:149.
26. Xu, Z. L., H. Mizuguchi, A. Ishii-Watabe, E. Uchida, T. Mayumi, and T. Hayakawa. 2002. Strength evaluation of transcriptional regulatory elements for transgene expression by adenovirus vector. *J Control Release* 81:155.
27. Huang, M. T., and C. M. Gorman. 1990. Intervening sequences increase efficiency of RNA 3' processing and accumulation of cytoplasmic RNA. *Nucleic Acids Res* 18:937.
28. Goonetilleke, N. P., H. McShane, C. M. Hannan, R. J. Anderson, R. H. Brookes, and A. V. Hill. 2003. Enhanced immunogenicity and protective efficacy against *Mycobacterium tuberculosis* of bacille Calmette-Guerin vaccine using mucosal administration and boosting with a recombinant modified vaccinia virus Ankara. *J Immunol* 171:1602.
29. McShane, H., A. A. Pathan, C. R. Sander, S. M. Keating, S. C. Gilbert, K. Huygen, H. A. Fletcher, and A. V. Hill. 2004. Recombinant modified vaccinia virus Ankara expressing antigen 85A boosts BCG-primed and naturally acquired antimycobacterial immunity in humans. *Nat Med* 10:1240.
30. Lewis, A. P. 1989. Cloning and analysis of the gene encoding the 230-kilodalton merozoite surface antigen of *Plasmodium yoelii*. *Mol Biochem Parasitol* 36:271.
31. Gilbert, S. C., M. Plebanski, S. J. Harris, C. E. Allsopp, R. Thomas, G. T. Layton, and A. V. Hill. 1997. A protein particle vaccine containing multiple malaria epitopes. *Nat Biotechnol* 15:1280.
32. McConkey, S. J., W. H. Reece, V. S. Moorthy, D. Webster, S. Dunachie, G. Butcher, J. M. Vuola, T. J. Blanchard, P. Gothard, K. Watkins, C. M. Hannan, S. Everaere, K. Brown, K. E. Kester, J. Cummings, J. Williams, D. G. Heppner, A. Pathan, K. Flanagan, N. Arulanantham, M. T. Roberts, M. Roy, G. L. Smith, J. Schneider, T. Peto, R. E. Sinden, S. C. Gilbert, and A. V. Hill. 2003. Enhanced T-cell immunogenicity of plasmid DNA vaccines boosted by recombinant modified vaccinia virus Ankara in humans. *Nat Med* 9:729.
33. Gilbert, S. C., J. Schneider, C. M. Hannan, J. T. Hu, M. Plebanski, R. Sinden, and A. V. Hill. 2002. Enhanced CD8 T cell immunogenicity and protective efficacy in a mouse 34. Romero, P., J. L. Maryanski, G. Corradin, R. S. Nussenzweig, V. Nussenzweig, and F. Zavala. 1989. Cloned cytotoxic T cells recognize an epitope in the circumsporozoite protein and protect against malaria. *Nature* 341:323.
35. Snow, R. W., C. A. Guerra, A. M. Noor, H. Y. Myint, and S. I. Hay. 2005. The global distribution of clinical episodes of *Plasmodium* falciparum malaria. *Nature* 434: 214-217.
36. Rowe, A. K., S. Y. Rowe, R. W. Snow, E. L. Korenromp, J. R. Armstrong Schellenberg, C. Stein, B. L. Nahlen, J. Bryce, R. E. Black, and R. W. Steketee. 2006. The burden of malaria mortality among African children in the year 2000. *Int J Epidemiol*
37. Hill, A. V. 2006. Pre-erythrocytic malaria vaccines: towards greater efficacy. *Nat Rev Immunol* 6:21-32.
38. Tsuji, M., and F. Zavala. 2003. T cells as mediators of protective immunity against liver stages of *Plasmodium*. *Trends Parasitol* 19:88-93.
39. Khusmith, S., Y. Charoenvit, S. Kumar, M. Sedegah, R. L. Beaudoin, and S. L. Hoffman. 1991. Protection against malaria by vaccination with sporozoite surface protein 2 plus CS protein. *Science* 252:715-718.
40. Gilbert, S. C., M. Plebanski, S. J. Harris, C. E. Allsopp, R. Thomas, G. T. Layton, and A. V. Hill. 1997. A protein particle vaccine containing multiple malaria epitopes. *Nat Biotechnol* 15:1280-1284.
41. Moorthy, V. S., S. McConkey, M. Roberts, P. Gothard, N. Arulanantham, P. Degano, J. Schneider, C. Hannan, M. Roy, S. C. Gilbert, T. E. Peto, and A. V. Hill. 2003. Safety of DNA and modified vaccinia virus Ankara vaccines against liver-stage *P. falciparum* malaria in non-immune volunteers. *Vaccine* 21:1995-2002.
42. Vuola, J. M., S. Keating, D. P. Webster, T. Berthoud, S. Dunachie, S. C. Gilbert, and A. V. Hill. 2005. Differential immunogenicity of various heterologous prime-boost vaccine regimens using DNA and viral vectors in healthy volunteers. *J Immunol* 174:449-455.
43. Webster, D. P., S. Dunachie, J. M. Vuola, T. Berthoud, S. Keating, S. M. Laidlaw, S. J. McConkey, I. Poulton, L. Andrews, R. F. Andersen, P. Bejon, G. Butcher, R. Sinden, M. A. Skinner, S. C. Gilbert, and A. V. Hill. 2005. Enhanced T cell-mediated protection against malaria in human challenges by using the recombinant poxviruses FP9 and modified vaccinia virus Ankara. *Proc Natl Acad Sci USA* 102:4836-4841.
44. Rodrigues, E. G., F. Zavala, D. Eichinger, J. M. Wilson, and M. Tsuji. 1997. Single immunizing dose of recombinant adenovirus efficiently induces CD8+ T cell-mediated protective immunity against malaria. *J Immunol* 158:1268-1274.
45. Chirmule, N., K. Propert, S. Magosin, Y. Qian, R. Qian, and J. Wilson. 1999. Immune responses to adenovirus and adeno-associated virus in humans. *Gene Ther* 6:1574-1583.
46. Tatsis, N., and H. C. Ertl. 2004. Adenoviruses as vaccine vectors. *Mol Ther* 10:616-629.
47. Zhi, Y., J. Figueredo, G. P. Kobinger, H. Hagan, R. Calcedo, J. R. Miller, G. Gao, and J. M. Wilson. 2006. Efficacy of Severe Acute Respiratory Syndrome Vaccine Based on a Nonhuman Primate Adenovirus in the Presence of Immunity Against Human Adenovirus. *Hum Gene Ther*
48. Fitzgerald, J. C., G. P. Gao, A. Reyes-Sandoval, G. N. Pavlakis, Z. Q. Xiang, A. P. Wlazlo, W. Giles-Davis, J. M. Wilson, and H. C. Ertl. 2003. A simian replication-defective adenoviral recombinant vaccine to HIV-1 gag. *J Immunol* 170:1416-1422.
49. Reyes-Sandoval, A., J. C. Fitzgerald, R. Grant, S. Roy, Z. Q. Xiang, Y. Li, G. P. Gao, J. M. Wilson, and H. C. Ertl. 2004. Human immunodeficiency virus type 1-specific immune responses in primates upon sequential immunization with adenoviral vaccine carriers of human and simian serotypes. *J Virol* 78:7392-7399.
50. Xiang, Z., G. Gao, A. Reyes-Sandoval, C. J. Cohen, Y. Li, J. M. Bergelson, J. M. Wilson, and H. C. Ertl. 2002. Novel, chimpanzee serotype 68-based adenoviral vaccine carrier for induction of antibodies to a transgene product. *J Virol* 76:2667-2675.
51. Harrington, L. E., M. Galvan, L. G. Baum, J. D. Altman, and R. Ahmed. 2000. Differentiating between memory and effector CD8 T cells by altered expression of cell surface O-glycans. *J Exp Med* 191:1241-1246.
52. Wolint, P., M. R. Betts, R. A. Koup, and A. Oxenius. 2004. Immediate cytotoxicity but not degranulation distinguishes effector and memory subsets of CD8+ T cells. *J Exp Med* 199:925-936.
53. Badovinac, V. P., K. A. Messingham, A. Jabbari, J. S. Haring, and J. T. Harty. 2005. Accelerated CD8+ T-cell memory and prime-boost response after dendritic-cell vaccination. *Nat Med* 11:748-756.
54. Jabbari, A., and J. T. Harty. 2006. Secondary memory CD8+ T cells are more protective but slower to acquire a central-memory phenotype. *J Exp Med* 203:919-932.
55. Baars, P. A., S. Sierro, R. Arens, K. Tesselaar, B. Hooibrink, P. Klenerman, and R. A. van Lier. 2005. Properties of murine (CD8+)CD27− T cells. *Eur J Immunol* 35:3131-3141.
56. Rammensee, H., J. Bachmann, N. P. Emmerich, O. A. Bachor, and S. Stevanovic. 1999. SYFPEITHI: database for MHC ligands and peptide motifs. *Immunogenetics* 50:213-219.
57. Romero, P., J. L. Maryanski, G. Corradin, R. S. Nussenzweig, V. Nussenzweig, and F. Zavala. 1989. Cloned cytotoxic T cells recognize an epitope in the circumsporozoite protein and protect against malaria. *Nature* 341:323-326.
58. Gilbert, S. C., J. Schneider, C. M. Hannan, J. T. Hu, M. Plebanski, R. Sinden, and A. V. Hill. 2002. Enhanced CD8 T cell immunogenicity and protective efficacy in a mouse malaria model using a recombinant adenoviral vaccine in heterologous prime-boost immunisation regimes. *Vaccine* 20:1039-1045.
59. Shiver, J. W., T. M. Fu, L. Chen, D. R. Casimiro, M. E. Davies, R. K. Evans, Z. Q. Zhang, A. J. Simon, W. L. Trigona, S. A. Dubey, L. Huang, V. A. Harris, R. S. Long, X. Liang, L. Handt, W. A. Schleif, L. Zhu, D. C. Freed, N. V. Persaud, L. Guan, K. S. Punt, A. Tang, M. Chen, K. A. Wilson, K. B. Collins, G. J. Heidecker, V. R. Fernandez, H. C. Perry, J. G. Joyce, K. M. Grimm, J. C. Cook, P. M. Keller, D. S. Kresock, H. Mach, R. D. Troutman, L. A. Isopi, D. M. Williams, Z. Xu, K. E. Bohannon, D. B. Volkin, D. C. Montefiori, A. Miura, G. R. Krivulka, M. A. Lifton, M. J. Kuroda, J. E. Schmitz, N. L. Letvin, M. J. Caulfield, A. J. Bett, R. Youil, D. C. Kaslow, and E. A. Emini. 2002. Replication-incompetent adenoviral vaccine vector elicits effective anti-immunodeficiency-virus immunity. *Nature* 415:331-335.
60. Bachmann, M. F., P. Wolint, K. Schwarz, P. Jager, and A. Oxenius. 2005. Functional properties and lineage relationship of CD8+ T cell subsets identified by expression of IL-7 receptor alpha and CD62L. *J Immunol* 175:4686-4696.
61. Appay, V., P. R. Dunbar, M. Callan, P. Klenerman, G. M. Gillespie, L. Papagno, G. S. Ogg, A. King, F. Lechner, C. A. Spina, S. Little, D. V. Havlir, D. D. Richman, N. Gruener, G. Pape, A. Waters, P. Easterbrook, M. Salio, V. Cerundolo, A. J. McMichael, and S. L. Rowland-Jones. 2002. Memory CD8+ T cells vary in differentiation phenotype in different persistent virus infections. *Nat Med* 8:379-385.
62. Croft, M. 2003. Costimulation of T cells by OX40, 4-1BB, and CD27: *Cytokine Growth Factor Rev* 14:265-273.
63. Gamadia, L. E., E. M. van Leeuwen, E. B. Remmerswaal, S. L. Yong, S. Surachno, P. M. Wertheim-van Dillen, I. J. Ten Berge, and R. A. Van Lier. 2004. The size and phenotype of virus-specific T cell populations is determined by repetitive antigenic stimulation and environmental cytokines. *J Immunol* 172:6107-6114.
64. Mahr, J. A., and L. R. Gooding. 1999. Immune evasion by adenoviruses. *Immunol Rev* 168:121-130.
65. Robinson, H. L., and R. R. Amara. 2005. T cell vaccines for microbial infections. *Nat Med* 11:S25-32.
66. Wherry, E. J., V. Teichgraber, T. C. Becker, D. Masopust, S. M. Kaech, R. Antia, U. H. von Andrian, and R. Ahmed. 2003. Lineage relationship and protective immunity of memory CD8 T cell subsets. *Nat Immunol* 4:225-234.
67. Keating, S. M., P. Bejon, T. Berthoud, J. M. Vuola, S. Todryk, D. P. Webster, S. J. Dunachie, V. S. Moorthy, S. J. McConkey, S. C. Gilbert, and A. V. Hill. 2005. Durable human memory T cells quantifiable by cultured enzyme-linked immunospot assays are induced by heterologous prime boost immunization and correlate with protection against malaria. *J Immunol* 175:5675-5680.
68. Bruna-Romero, O., G. Gonzalez-Aseguinolaza, J. C. Hafalla, M. Tsuji, and R. S. Nussenzweig. 2001. Complete, long-lasting protection against malaria of mice primed and boosted with two distinct viral vectors expressing the same plasmodial antigen. *Proc Natl Acad Sci USA* 98:11491-11496.
69. Casimiro, D. R., L. Chen, T. M. Fu, R. K. Evans, M. J. Caulfield, M. E. Davies, A. Tang, M. Chen, L. Huang, V. Harris, D. C. Freed, K. A. Wilson, S. Dubey, D. M. Zhu, D. Nawrocki, H. Mach, R. Troutman, L. Isopi, D. Williams, W. Hurni, Z. Xu, J. G. Smith, S. Wang, X. Liu, L. Guan, R. Long, W. Trigona, G. J. Heidecker, H. C. Perry, N. Persaud, T. J. Toner, Q. Su, X. Liang, R. Youil, M. Chastain, A. J. Bett, D. B. Volkin, E. A. Emini, and J. W. Shiver. 2003. Comparative immunogenicity in rhesus monkeys of DNA plasmid, recombinant vaccinia virus, and replication-defective adenovirus vectors expressing a human immunodeficiency virus type 1 gag gene. *J Virol* 77:6305-6313.
70. Lemckert, A. A., S. M. Sumida, L. Holterman, R. Vogels, D. M. Truitt, D. M. Lynch, A. Nanda, B. A. Ewald, D. A. Gorgone, M. A. Lifton, J. Goudsmit, M. J. Havenga, and D. H. Barouch. 2005. Immunogenicity of heterologous prime-boost regimens involving recombinant adenovirus serotype 11 (Ad11) and Ad35 vaccine vectors in the presence of anti-ad5 immunity. *J Virol* 79:9694-9701.
71. McConkey, S. J., W. H. Reece, V. S. Moorthy, D. Webster, S. Dunachie, G. Butcher, J. M. Vuola, T. J. Blanchard, P. Gothard, K. Watkins, C. M. Hannan, S. Everaere, K. Brown, K. E. Kester, J. Cummings, J. Williams, D. G. Heppner, A. Pathan, K. Flanagan, N. Arulanantham, Roberts, M. Roy, G. L. Smith, J. Schneider, T. Peto, R. E. Sinden, S. C. Gilbert, and A. V. Hill. 2003. Enhanced T-cell immunogenicity of plasmid DNA vaccines boosted by recombinant modified vaccinia virus Ankara in humans. *Nat Med* 9:729-735.
72. Schneider, J., S. C. Gilbert, T. J. Blanchard, T. Hanke, K. J. Robson, C. M. Hannan, M. Becker, R. Sinden, G. L. Smith, and A. V. Hill. 1998. Enhanced immunogenicity for CD8+ T cell induction and complete protective efficacy of malaria DNA vaccination by boosting with modified vaccinia virus Ankara. *Nat Med* 4:397-402.
73. Roy, S., G. Gao, Y. Lu, X. Zhou, M. Lock, R. Calcedo, and J. M. Wilson. 2004. Characterization of a family of chimpanzee adenoviruses and development of molecular clones for gene transfer vectors. *Hum Gene Ther* 15:519-530.
74. Moore, A. C., A. Gallimore, S. J. Draper, K. R. Watkins, S. C. Gilbert, and A. V. Hill. 2005. Anti-CD25 antibody enhancement of vaccine-induced immunogenicity: increased durable cellular immunity with reduced immunodominance. *J Immunol* 175:7264-7273.

Sequence Listing.

Nucleotide Sequence antigen PfM117 (SE ID NO. 1)
ATGAAGATCATCTTCTTCCTGTGCTCTTTCCTGTTCTTCATCATCAACAC
CCAGTGCGTGACCCACGAGAGCTACCAGGAGCTGGTGAAGAAGCTGGAGG
CCCTGGAGGACGCCGTGCTGACCGGCTACAGCCTGTTCCAGAAAGAGAAG
ATGGTGCTGAACGAGCTGTTCGACCTGACCAACCACATGCTGACCCTGTG
CGACAACATCCACGGCTTCAAGTACCTGATCGACGGCTACGAGGAGATCA
ACGAGCTGCTGTACAAGCTGAACTTCTACTTCGACCTGCTGCGCGCCAAG
CTGAACGACGTGTGCGCCAACGACTACTGCCAGATCCCCTTCAACCTGAA
GATCCGCGCCAACGAGCTGGACGTGCTGAAGAAACTGGTGTTCGGCTACC
GGAAGCCCCTGGACAACATCAAGGACAACGTGGGCAAGATGGAGGACTAC
ATCAAGAAGAACAAGACCACCATCGCCAACATTAACGAGCTGATCGAGGG
CAGCAAGAAAACCATCGACCAGAACAAGAACGCCGACAACGAGGAGGGCA
AGAAGAAGCTGTACCAGGCCCAGTACGACCTGAGCATCTACAACAAGCAG
CTGGAGGAGGCCCACAACCTGATCAGCGTGCTGGAGAAGCGGATCGACAC
CCTGAAGAAGAACGAGAACATCAAGATCAAGGAGATCGCCAAGACCATCA
AGTTCAACATCGACTCCCTGTTCACCGACCCCCTGGAGCTGGAGTACTAC
CTGCGCGAGAAGAATAAGAAGATGCAGATCAAGAAGCTGACCCTGCTGAA
GGAGCAGCTGGAAAGCAAGCTGAACAGCCTGAACAACCCCCACAACGTGC
TGCAGAACTTCAGCGTGTTCTTCAACAAGAAGAAGGAGGCCGAGATCGCC
GAAACCGAGAACACCCTGGAGAATACCAAGATCCTGCTGAAGCACTACAA
GGGCCTGGTGAAGTACTACAACGGCGAGAGCAGCCCCCTGAAAACCCTGA
GCGAAGTGAGCATCCAGACCGAGGACAACTACGCCAACCTGGAGGGCCAA
GTGGTCACCGGCGAGGCCGTGACCCCCAGCGTGATCGACAACATCCTGAG
CAAGATCGAGAACGAGTACGAGGTGCTGTACCTGAAGCCCCTGGCCGGCG
TGTACAGAAGCCTGAAGAAGCAGCTGGAAAACAACGTGATGACCTTCAAC
GTGAACGTGAAGGACATCCTGAACAGCCGGTTCAACAAGCGGGAGAACTT
CAAGAACGTGCTGGAAAGCGACCTGATCCCCTACAAGGACCTGACCAGCA
GCAACTACGTGGTGAAGGACCCCCTACAAGTTCCTGAACAAAGAGAAGCGG
GATAAGTTCCTGAGCAGCTACAACTACATCAAGGACAGCATCGACACCGA
CATCAACTTCGCCAACGACGTGCTGGGCTACTACAAGATCCTGAGCGAGA
AGTACAAGAGCGACCTGGACAGCATCAAGAAGTACATCAACGACAAGCAG
GGCGAGAACGAGAAGTACCTGCCCTTCCTGAATAACATCGAGACCCTGTA
CAAGACCGTGAACGACAAGATCGACCTGTTCGTGATCCACCTGGAAGCCA
AGGTGCTGAACTACACCTACGAGAAGAGCAACGTGGAGGTGAAGATCAAA
GAGCTGAACTACCTGAAAACCATCCAGGACAAGCTGGCCGACTTCAAGAA
GAACAACAACTTCGTCGACATCGCCGACCTGAGCACCGACTACAACCACA
ACAACCTGCTGACCAAGTTCCTGTCCACCGGCATGGTGTTCGAGAACCTG
GCCAAGACAGTGCTGTCCAACCTGCTGGACGGCAACCTGCAGGGCggagg
gggaCCCGGGGGAGGGGACCAAGTCGTGACCGGCGAAGCCATCAGCGTGA
CCATGGATAACATCCTGAGCGGCTTCGAAAACGAATACGACGTGATCTAT
CTGAAACCCCTGGCCGGCGTGTATCGGTCTCTGAAGAAGCAGATCGAGAA
GAACATCTTCACCTTCAATCTGAACCTGAACGATATCCTGAATAGCCGCC
TGAAGAAGCGCAAGTACTTCCTGGACGTGCTGGAGAGCGACCTGATGCAG
TTCAAGCACATCGGCGACAACGAGTACATCATCGAGGACAGCTTCAAGCT
GCTGAACAGCGAGCAGAAGAACACACTGCTGAAGTCTTACAAGTATATCA
AGGAGAGCGTGGAGAACGATATCAAGTTCGCCCAGGAGGGCATCAGCTAC
TACGAGAAAGTGCTGGCCAAGTACAAGGACGATCTGGAGTCCATCAAGAA
AGTGATCAAGGAGGAGAAGGAGAAGTTCCCCAGCAGCCCCCCCACCACCC
CCCCCAGCCCCGCCAAGACCGACCGACGAGCAGAAGAAGGAGAGCAAGTTCCTG
CCTTTTCTGACCAATATCGAGACACTGTATAACAACCTGGTGAATAAGAT
CGACGACTACCTGATCAATCTGAAGGCCAAGATCAACGATTGCAACGTGG
AGAAGGACGAGGCCCACGTGAAGATCACCAAGCTGAGCGATCTGAAAGCC
ATCGACGATAAGATCGATCTGTTCAAGAACCCCTACGACTTCGAGGCCAT

Sequence Listing.

TAAGAAGCTGATCAACGACGACACCAAGAAGGACATGCTGGGCAAGCTGC
TGTCTACCGGCCTGGTGCAGAATTTCCCCAACACCATCATCAGCAAGCTG
ATCGAAGGGAAGTTCCAGGATATGCTGAACATCGCCCAGCACCAGTGCGT
GAAGAAGCAGATCCCCGAGAACAGCGGCTGCTTCCGGCACCTGGACGAGC
GCGAGGAGTGGAAGTGCCTGCTGAATTACAAGCAGGAGGGCGACAAGTGC
GTGGAGAATCCCAACCCCACCTGCAACGAGAACAACGGCGGCTGCGACGC
CGACGCCACCTGCACCGAGGAGGACAGCGGCAGCAGCCGGAAGAAGATCA
CCTGCGAGTGCACCAAGCCCGACAGCTACCCCCTGTTCGACGGCATCTTC
TGCAGCAGCTCCAACTTAATATTATATTCCTTTATCTGA

Amino Acid Sequence antigen PfM117 (SEQ ID NO. 2)
MKIIFFLCSFLFFIINTQCVTHESYQELVKKLEALEDAVLTGYSLFQKEK
MVLNELFDLTNHMLTICDNIHGFKYLIDGYEEINELLYKLNFYFDLLRAK
LNDVCANDYCQIPFNLKIRANELDVLKKLVFGYRKPLDNIKDNVGKMEDY
IKKNKTTIANINELIEGSKKTIDQNKNADNEEGKKKLYQAQYDLSIYNKQ
LEEAHNLISVLEKRIDTLKKNENIKIKEIAKTIKFNIDSLFTDPLELEYY
LREKNKKMQIKKLTLLKEQLESKLNSLNNPHNVLQNFSVFFNKKKEAEIA
ETENTLENTKILLKHYKGLVKYYNGESSPLKTLSEVSIQTEDNYANLEGQ
VVTGEAVTPSVIDNILSKIENEYEVLYLKPLAGVYRSLKKQLENNVMTFN
VNVKDILNSRFNKRENFKNVLESDLIPYKDLTSSNYVVKDPYKFLNKEKR
DKFLSSYNYIKDSIDTDINFANDVLGYYKILSEKYKSDLDSIKKYINDKQ
GENEKYLPFLNNIETLYKTVNDKIDLFVIHLEAKVLNYTYEKSNVEVKIK
ELNYLKTIQDKLADFKKNNNFVGIADLSTDYNHNNLLTKFLSTGMVFENL
AKTVLSNLLDGNLQGGGPGGGDQVVTGEAISVTMDNILSGFENEYDVIY
LKPLAGVYRSLKKQIEKNIFTFNLNLNDILNSRLKKRKYFLDVLESDLMQ
FKHISSNEYIIEDSFKLLNSEQKNTLLKSYKYIKESVENDIKFAQEGISY
YEKVLAKYKDDLESIKKVIKEEKEKFPSSPPTTPPSPAKTDEQKKESKFL
PPLTNIETLYNNLVNKIDDYLINLKAKINDCNVEKDEAHVKITKLSDLKA
IDDKIDLFKNPYDFEAIKKLINDDTKKDMLGKLLSTGLVQNFPNTIISKL
IEGKFQDMLNIAQHQCVKKQIPENSGCFRHLDEREEWKCLLNYKQEGDKC
VENPNPTCNENNGGCDADATCTEEDSGSSRKKITCECTKPDSYPLFDGIF
CSSSNLILYSFI.

Nucleotide Sequence antigen PfM128 (SEQ ID NO. 3)
ATGAAGATCATCTTCTTCCTGTGCTCTTTCCTGTTCTTCATCATCAACAC
CCAGTGCGTGACCCACGAGAGCTACCAGGAGCTGGTGAAGAAGCTGGAAG
CCCTGGAGGACGCCGTGCTGACCGGCTACAGCCTGTTCCAGAAAGAGAAG
ATGGTGCTGAACGAGCTGTTCGACCTGACCAACCACATGCTGACCCTGTG
CGACAACATCCACGGCTTCAAGTACCTGATCGACGGCTACGAGGAGATCA
ACGAGCTGCTGTACAAGCTGAACTTCTACTTCGACCTGCTGCGCGCCAAG
CTGAACGACGTGTGCGCCAACGACTACTGCCAGATCCCCTTCAACCTGAA
GATCCGCGCCAACGAGCTGGACGTGCTGAAGAAACTGGTGTTCGGCTACC
GGAAGCCCCTGGACAACATCAAGGACAACGTGGGCAAGATGGAGGACTAC
ATCAAGAAGAACAAGACCACCATCGCCAACATTAACGAGCTGATCGAGGG
CAGCAAGAAAACCATCGACCAGAACAAGAACGCCGACAACGAGGAGGGCA
AGAAGAAGCTGTACCAGGCCCAGTACGACCTGAGCATCTACAACAAGCAG
CTGGAGGAGGCCCACAACCTGATCAGCGTGCTGGAGAAGCGGATCGACAC
CCTGAAGAAGAACGAGAACATCAAGATCAAGGAGATCGCCAAGACCATCA
AGTTCAACATCGACTCCCTGTTCACCGACCCCCTGGAGCTGGAGTACTAC
CTGCGCGAGAAGAATAAGAAGATGCAGATCAAGAAGCTGACCCTGCTGAA
GGAGCAGCTGGAAAGCAAGCTGAACAGCCTGAACAACCCCCACAACGTGC
TGCAGAACTTCAGCGTGTTCTTCAACAAGAAGAAGGAGGCCGAGATCGCC
GAAACCGAGAACACCCTGGAGAATACCAAGATCCTGCTGAAGCACTACAA
GGGCCTGGTGAAGTACTACAACGGCGAGAGCAGCCCCCTGAAAACCCTGA
GCGAAGTGAGCATCCAGACCGAGGACAACTACGCCAACCTGGAGGGCCAA
GTGGTCACCGGCGAGGCCGTGACCCCCAGCGTGATCGACAACATCCTGAG
CAAGATCGAGAACGAGTACGAGGTGCTGTACCTGAAGCCCCTGGCCGGCG
TGTACAGAAGCCTGAAGAAGCAGCTGGAGAACAACGTGATGACCTTCAAC
GTGAACGTGAAGGACATCCTGAACAGCCGGTTCAACAAGCGGGAGAACTT
CAAGAACGTGCTGGAAAGCGACCTGATCCCCTACAAGGACCTGACCAGCA
GCAACTACGTGGTGAAGGACCCCTACAAGTTCCTGAACAAGGAGAAGCGG
GATAAGTTCCTGAGCAGCTACAACTACATCAAGGACAGCATCGACACCGA
CATCAACTTCGCCAACGACGTGCTGGGCTACTACAAGATCCTGAGCGAGA
AGTACAAGAGCGACCTGGACAGCATCAAGAAGTACATCAACGACAAGCAG
GGCGAGAACGAGAAGTACCTGCCCTTCCTGAATAACATCGAGACCCTGTA
CAAGACCGTGAACGACAAGATCGACCTGTTCGTGATCCACCTGGAAGCCA
AGGTGCTGAACTACACCTACGAGAAGAGCAACGTGGAGGTGAAGATCAAA
GAGCTGAACTACCTGAAAACCATCCAGGACAAGCTGGCCGACTTCAAGAA
GAACAACAACTTCGTCGGCATCGCCGACCTGAGCACCGACTACAACCACA
ACAACCTGCTGACCAAGTTCCTGTCCACCGGCATGGTGTTCGAGAACCTG
GCCAAGACAGTGCTGTCCAACCTGCTGGACGGCAACCTGCAGGGCATGCT
CAATATCGCACAGCATCAGTGTGTCAAAAAACAGATTCCTCAGAACTCCG
GCTGCTTTAGACACCTGGATGAACGGGAAGAATGGAAGTGTCTGCTCAAC
TATAAACAGGAAGGTGATAAGTGTGTCGAGAACCCTAACCCTACCTGTAA
TGAGAATAATGGGGGCTGTGATGCCGATGCCAATGTACCGAAGAAGATT
ACCTGCGAGTGCACCAAGCCCGACAGCTACCCCCTGTTCGACGGCATCTT CGGGGGAGGGGACCAAGTCGTGACCGGCGAAGCCATCAGCGTGACCATGG
ATAACATCCTGAGCGGCTTCGAAAACGAATACGACGTGATCTATCTGAAA
CCCCTGGCCGGCGTGTATCGGTCTCTGAAGAAGCAGATCGAGAAGAACAT
CTTCACCTTCAATCTGAACCTGAACGATATCCTGAATAGCCGCCTGAAGA
AGCGCAAGTACTTCCTGGACGTGCTGGAGAGCGACCTGATGCAGTTCAAG
CACATCAGCAGCAACGAGTACATCATCGAGGACAGCTTCAAGCTGCTGAA
CAGCGAGCAGAAGAACACACTGCTGAAGTCTTACAAGTATATCAAGGAGA
GCGTGGAGAACGATATCAAGTTCGCCCAGGAGGGCATCAGCTACTACGAG
AAAGTGCTGGCCAAGTACAAGGACGATCTGGAGTCCATCAAGAAAGTGAT
CAAGGAGGAGAAGGAGAAGTTCCCCAGCAGCCCCCCCACCACCCCCCCCA
GCCCCGCCAAGACCGACGAGCAGAAGAAGGAGAGCAAGTTCCTGCCTTTT
CTGACCAATATCGAGACACTGTATAACAACCTGGTGAATAAGATCGACGA
CTACCTGATCAATCTGAAGGCCAAGATCAACGATTGCAACGTGGAGAAGG
ACGAGGCCCACGTGAAGATCACCAAGCTGAGCGATCTGAAAGCCATCGAC
GATAAGATCGATCTGTTCAAGAACCCCTACGACTTCGAGGCCATTAAGAA
GCTGATCAACGACGACACCAAGAAGGACATGCTGGGCAAGCTGCTGTCTA
CCGGCCTGGTGCAGAATTTCCCCAACACCATCATCAGCAAGCTGATCGAA
GGGAAGTTCCAGGATATGCTGAACATCGCCCAGCACCAGTGCGTGAAGAA
GCAGATCCCCGAGAACAGCGGCTGCTTCCGGCACCTGGACGAGCGCGAGG
AGTGGAAGTGCCTGCTGAATTACAAGCAGGAGGGCGACAAGTGCGTGGAG
AATCCCAACCCCACCTGCAACGAGAACAACGGCGGCTGCGACGCCGACGC
CACCTGCACCGAGGAGGACAGCGGCAGCAGCCGGAAGAAGATCACCTGCG
AGTGCACCAAGCCCGACAGCTACCCCCTGTTCGACGGCATCTTCTGCAGC
AGCTCCAACTTAATATTATATTCCTTTATCTGA.

Amino Acid Sequence antigen PfM128 (SEQ ID NO. 4)
MKIIFFLCSFLFFIINTQCVTHESYQELVKKLEALEDAVLTGYSLFQKEK
MVLNELFDLTNHMLTICDNIHGFKYLIDGYEEINELLYKLNFYFDLLRAK
LNDVCANDYCQIPFNLKIRANELDVLKKLVFGYRKPLDNIKDNVGKMEDY
IKKNKTTIANINELIEGSKKTIDQNKNADNEEGKKKLYQAQYDLSIYNKQ
LEEAHNLISVLEKRIDTLKKNENIKIKEIAKTIKFNIDSLFTDPLELEYY
LREKNKKMQIKKLTLLKEQLESKLNSLNNPHNVLQNFSVFFNKKKEAEIA
ETENTLENTKILLKHYKGLVKYYNGESSPLKTLSEVSIQTEDNYANLEGQ
VVTGEAVTPSVIDNILSKIENEYEVLYLKPLAGVYRSLKKQLENNVMTFN
VNVKDILNSRFNKRENFKNVLESDLIPYKDLTSSNYVVKDPYKFLNKEKR
DKFLSSYNYIKDSIDTDINFANDVLGYYKILSEKYKSDLDSIKKYINDKQ
GENEKYLPFLNNIETLYKTVNDKIDLFVIHLEAKVLNYTYEKSNVEVKIK
ELNYLKTIQDKLADFKKNNNFVGIADLSTDYNHNNLLTKFLSTGMVFENL
AKTVLSNLLDGNLQGMLNIAQHQCVKKQIPQNSGCFRHLDEREEWKCLLN
YKQEGDKCVENPNPTCNENNGGCDADAKCTEEDSGSNGKKITCECTKPDS
YPLFDGIFCSSSNGGGPGGGDQVVTGEAISVTMDNILSGFENEYDVIYLK
PLAGVYRSLKKQIEKNIFTFNLNLNDILNSRLKKRKYFLDVLESDLMQFK
HISSNEYIIEDSFKLLNSEQKNTLLKSYKYIKESVENDIKFAQEGISYYE
KVLAKYKDDLESIKKVIKEEKEKFPSSPPTTPPSPAKTDEQKKESKFLPF
LTNIETLYNNLVNKIDDYLINLKAKINDCNVEKDEAHVKITKLSDLKAID
DKIDLFKNPYDFEAIKKLINDDTKKDMLGKLLSTGLVQNFPNTIISKLIE
GKFQDMLNIAQHQCVKKQIPENSGCFRHLDEREEWKCLLNYKQEGDKCVE
NPNPTCNENNGGCDADATCTEEDSGSSRKKITCECTKPDSYPLFDGIFCS
SSNLILYSFI.

Nucleotide Sequence antigen PfM115 (SEQ ID NO. 5)
ATGAAGATCATCTTCTTCCTGTGCTCTTTCCTGTTCTTCATCATCAACAC
CCAGTGCGTGACCCACGAGAGCTACCAGGAGCTGGTGAAGAAGCTGGAAG
CCCTGGAGGACGCCGTGCTGACCGGCTACAGCCTGTTCCAGAAAGAGAAG
ATGGTGCTGAACGAGCTGTTCGACCTGACCAACCACATGCTGACCCTGTG
CGACAACATCCACGGCTTCAAGTACCTGATCGACGGCTACGAGGAGATCA
ACGAGCTGCTGTACAAGCTGAACTTCTACTTCGACCTGCTGCGCGCCAAG
CTGAACGACGTGTGCGCCAACGACTACTGCCAGATCCCCTTCAACCTGAA
GATCCGCGCCAACGAGCTGGACGTGCTGAAGAAACTGGTGTTCGGCTACC
GGAAGCCCCTGGACAACATCAAGGACAACGTGGGCAAGATGGAGGACTAC
ATCAAGAAGAACAAGACCACCATCGCCAACATTAACGAGCTGATCGAGGG
CAGCAAGAAAACCATCGACCAGAACAAGAACGCCGACAACGAGGAGGGCA
AGAAGAAGCTGTACCAGGCCCAGTACGACCTGAGCATCTACAACAAGCAG
CTGGAGGAGGCCCACAACCTGATCAGCGTGCTGGAGAAGCGGATCGACAC
CCTGAAGAAGAACGAGAACATCAAGATCAAGGAGATCGCCAAGACCATCA
AGTTCAACATCGACTCCCTGTTCACCGACCCCCTGGAGCTGGAGTACTAC
CTGCGCGAGAAGAATAAGAAGATGCAGATCAAGAAGCTGACCCTGCTGAA
GGAGCAGCTGGAAAGCAAGCTGAACAGCCTGAACAACCCCCACAACGTGC
TGCAGAACTTCAGCGTGTTCTTCAACAAGAAGAAGGAGGCCGAGATCGCC
GAAACCGAGAACACCCTGGAGAATACCAAGATCCTGCTGAAGCACTACAA
GGGCCTGGTGAAGTACTACAACGGCGAGAGCAGCCCCCTGAAAACCCTGA
GCGAAGTGAGCATCCAGACCGAGGACAACTACGCCAACCTGGAGGGCCAA
GTGGTCACCGGCGAGGCCGTGACCCCCAGCGTGATCGACAATATCCTGAG
CAAGATCGAGAACGAGTACGAAGTGCTGTACCTGAAGCCCCTGGCCGGCG
TGTACCGGAGCCTGAAGAAACAGCTGGAGAACAACGTGATGACCTTCAAC
GTGAACGTGAAGGACATCCTGAACAGCCGGTTCAACAAGCGCGAGAACTT
CAAGAACGTGCTGGAGTCCGACCTGATCCCCTACAAGGACCTGACCAGCA

Sequence Listing.

GCAACTACGTGGTGAAGGACCCCTACAAGTTCCTGAACAAGGAGAAGCGC
GACAAGTTTCTGTCCAGCTACAACTACATTAAGGACAGCATCGACACCGA
CATCAACTTCGCCAACGACGTGCTGGGCTACTACAAGATCCTGAGCGAGA
AGTACAAGAGCGACCTGGATAGCATCAAGAAGTACATCAACGACAAGCAG
GGCGAGAACGAGAAGTACCTGCCCTTCCTGAATAACATCGAGACCCTGTA
CAAGACCGTGAACGACAAGATCGACCTGTTCGTGATCCACCTGGAGGCCA
AAGTGCTGAACTACACCTACGAGAAGAGCAACGTGGAAGTGAAGATTAAG
GAGCTGAACTACCTGAAAACCATCCAGGACAAGCTGGCCGACTTCAAGAA
GAATAACAACTTCGTGGGCATCGCCGATCTGAGCACCGACTACAACCACA
ACAACCTGCTGACCAAGTTCCTGTCCACCGGCATGGTGTTCGAGAACCTG
CTGAAGAGCGTGCTGAGCAACCTGCTGGACTGGAAGCTGGCCCGCTACGT
GAAGCACTTCACCACCCCCATGCGGAAAAAGACCATGATCCAGCAGAGCG
GAGGGGGACCCGGGGAGGGGACCAAGTCGTGACCGGCGAAGCCATCAGC
GTGACCATGGATAACATCCTGAGCGGCTTCGAAAACGAATACGACGTGAT
CTATCTGAAACCCCTGGCCGGCGTGTATCGGTCTCTGAAGAAGCAGATCG
AGAAGAACATCTTCACCTTCAATCTGAACCTGAACGATATCCTGAATAGC
CGCCTGAAGAAGCGCAAGTACTTCCTGGACGTGCTGGAGAGCGACCTGAT
GCAGTTCAAGCACATCAGCAGCAACGAGTACATCATCGAGGACAGCTTCA
AGCTGCTGAACAGCGAGCAGAAGAACACACTGCTGAAGTCTTACAAGTAT
ATCAAGGAGAGCGTGGAGAACGATATCAAGTTCGCCCAGGAGGGCATCAG
CTACTACGAGAAAGTGCTGGCCAAGTACAAGGACGATCTGGAGTCCATCA
AGAAAGTGATCAAGGAGGAGAAGGAGAAGTTCCCCAGCAGCCCCCCCACC
ACCCCCCCAGCCCCGCCAAGACCGACGAGCAGAAGAAGGAGAGCAAGTT
CCTGCCTTTTCTGACCAATATCGAGACTCTGTATAACAACCTGGTGAATA
AGATCGACGACTACCTGATCAATCTGAAGGCCAAGATCAACGATTGCAAC
GTGGAGAAGGACGAGGCCCACGTGAAGATCACCAAGCTGAGCGATCTGAA
AGCCATCGACGATAAGATCGATCTGTTCAAGAACCCCTACGACTTCGAGG
CCATTAAGAAGCTGATCAACGACGACACCAAGAAGGACATGCTGGGCAAG
CTGCTGTCTACCGGCCTGGTGCAGAATTTCCCCAACACCATCATCAGCAA
GCTGATCGAAGGGAAGTTCCAGGATATGCTGAACATCGCCCAGCACCAGT
GCGTGAAGAAGCAGATCCCCGAGAACAGCGGCTGCTTCCGGCACCTGGAC
GAGCGCGAGGAGTGGAAGTGCCTGCTGAATTACAAGCAGGAGGGCGACAA
GTGCGTGGAGAATCCCAACCCCACCTGCAACGAGAACAACGGCGGCTGCG
ACGCCGACGCCACCTGCACCGAGGAGGACAGCGGCAGCAGCCGGAAGAAG
ATCACCTGCGAGTGCACCAAGCCCGACAGCTACCCCCTGTTCGACGGCAT
CTTCTGCAGCAGCTCCAACTTAATATTATATTCCTTTATCTGA

Amino Acid Sequence antigen PfM115 (SEQ ID NO. 6)
MKIIFFLCSFLFFIINTQCVTHESYQELVKKLEALEDAVLTGYSLFQKEK
MVLNELFDLTNHMLTLCDNIHGFKYLIDGYEEINELLYKLNFYFDLLRAK
LNDVCANDYCQIPFNLKIRANELDVLKKLVFGYRKPLDNIKDNVGKMEDY
IKKNKTTIANINELIEGSKKTIDQNKNADNEEGKKKLYQAQYDLSIYNKQ
LEEAHNLISVLEKRIDTLKKNENIKIKEIAKTIKFNIDSLFTDPLELEYY
LREKNKKMQIKKLTLLKEQLESKLNSLNNPHNVLQNFSVFFNKKKEAEIA
ETENTLENTKILLKHYKGLVKYYNGESSPLKTLSEVSIQTEDNYANLEGQ
VVTGEAVTTSVIDNILSKIENEYEVLYLKPLAGVYRSLKKLENNVMTFN
VNVKDILNSRFNKRENFKNVLESDLIPYKDLTSSNYVVKDPYKFLNKEKR
DKFLSSYNYIKDSIDTDINFANDVLGYYKILSEKYKSDLDSIKKYINDKQ
GENEKYLPFLNNIETLYKTVNDKIDLFVIHLEAKVLNYTYEKSNVEVKIK
ELNYLKTIQDKLADFKKNNNFVGIADLSTDYNHNNLLTKFLSTGMVFENL
LKSVLSNLLDWKLARYVKHFTTPMRKKTMIQQSGGGPGGGDQVVTGEAIS VTMDNILSGFENEYDVIYLKPLAGVYRSLKKQIEKNIFTFNLNLNDILNS
RLKKRKYFLDVLESDLMQFKHISSNEYIIEDSFKLLNSEQKNTLLKSYKY
IKESVENDIKFAQEGISYYEKVLAKYKDDLESIKKVIKEEKEKFPSSPPT
TPPSPAKTDEQKKESKFLPFLTNIETLYNNLVNKIDDYLINLKAKINDCN
VEKDEAHVKITKLSDLKAIDDKIDLFKNPYDFEAIKKLINDDTKKDMLGK
LLSTGLVQNFPNTIISKLIEGKFQDMLNIAQHQCVKKQIPENSGCFRHLD
EREEWKCLLNYKQEGDKCVENPNPTCNENNGGCDADATCTEEDSGSSRKK
ITCECTKPDSYPLFDGIFCSSSNLILYSFI.

DNA Sequence of CMV IE1 promoter including
intron A (1947 bp) (SEQ ID NO. 7)
TGTGAGTTTCTGTGTAACTGATATCGCCATTTTTCCAAAAGTGATTTTTG
GGCATACGCGATATCTGGCGATAGCGCTTATATCGTTTACGGGGGATGGC
GATAGACGACTTTGGTGACTTGGGCGATTCTGTGTGTCGCAAATATCGCA
GTTTCGATATAGGTGACAGACGATATGAGGCTATATCGCCGATAGAGGCC
ACATCAAGCTGGCACATGGCCAATGCATATCGATCTATACATTGAATCAA
TATTGGCCATTAGCCATATTATTCATTGGTTATATAGCATAAATCAATAT
TGGCTATTGGCCATTGCATACGTTGTATCCATATCATAATATGTACATTT
ATATTGGCTCATGTCCAACATTACCGCCATGTTGACATTGATTATTGACT
AGTTATTAATAGTAATCAATTACGGGGTCATTAGTTCATAGCCCATATAT
GGAGTTCCGCGTTACATAACTTACGGTAAATGGCCCGCCTGGCTGACCGC
CCAACGACCCCCGCCCATTGACGTCAATAATGACGTATGTTCCCATAGTA
ACGCCAATAGGGACTTTCCATTGACGTCAATGGGTGGAGTATTTACGGTA
AACTGGCCCACTTGGCAGTACATCAAGTGTATCATATGCCAAGTACGCCC
CTATTGACGTCAATGACGGTAAATGGCCCGCCTGGCATTATGCCCAGTAC
ATGACCTTATGGGACTTTCCTACTTGGCAGTACATCTACGTATTAGTCAT
CGCTATTACCATGGTGATGCGGTTTTGGCAGTACATCAATGGGCGTGGAT
AGCGGTTTGACTCACGGGGATTTCCAAGTCTCCACCCCATTGACGTCAAT
GGGAGTTTGTTTTGGCACCAAAATCAACGGGACTTTCCAAAATGTCGTAA
CAACTCCGCCCCATTGACGCAAATGGGCGGTAGGCGTGTACGGTGGGAGG
TCTATATAAGCAGAGCTCGTTTAGTGAACCGTCAGATCGCCTGGAGACGC
CATCCACGCTGTTTTGACCTCCATAGAAGACACCGGGACCGATCCAGCCT
CCGCGCCGGGAACGGTGCATTGGAACGCGGATTCCCCGTGCCAAGAGTG
ACGTAAGTACCGCCTATAGAGTCTATAGGCCCACCCCCTTGGCTTCTTAT
GCATGCTATACTGTTTTTGGCTTGGGGTCTATACACCCCGCTTCCTCAT
GTTATAGGTGATGGTATAGCTTAGCCTATAGGTGTGGGTTATTGACCATT
ATTGACCACTCCCCTATTGGTGACGATACTTTCCATTACTAATCCATAAC
ATGGCTCTTTGCCACAACTCTCTTTATTGGCTATATGCCAATACACTGTC
CTTCAGAGACTGACACGGACTCTGTATTTTTACAGGATGGGGTCTCATTT
ATTATTTACAAATTCATATATCAACACCACCGTCCCCAGTGCCCGCAGT
TTTTATTAAACATAACGTGGGATCTCCACGCGAATCTCGGGTACGTGTTC
CGGACATGGGCTCTTCTCCGGTAGCGGCGGAGCTTCTACATCCGAGCCCT
GCTCCCATGCCTCCAGCGACTCATGGTCGCTCGGCAGCTCCTTGCTCCTA
ACAGTGGAGGCCAGACTTAGGCACAGCACGATGCCCACCACCACCAGTGT
GCCGCACAAGGCCGTGGCGGTAGGGTATGTGTCTGAAAATGAGCTCGGGG
AGCGGGCTTGCACCGCTGACGCATTTGGAAGACTTAAGGCAGCGGCAGAA
GAAGATGCAGGCAGCTGAGTTGTTGTGTTCTGATAAGAGTCAGAGGTAAC
TCCCGTTGCGGTGCTGTTAACGGTGGAGGGCAGTGTAGTCTGAGCAGTAC
TCGTTGCTGCCGCGCGCCACCAGACATAATAGCTGACAGACTAACAGA
CTGTTCCTTTCCATGGGTCTTTTCTGCAGTCACCGTCCTTGACACGA

---

The invention claimed is:

1. An adenoviral vector comprising a promoter and a nucleic acid sequence encoding an antigen from a pathogen or a tumour antigen under the control of said promoter, wherein said promoter consists of SEQ ID NO: 7, and wherein said antigen is not a murine malaria parasite antigen.

2. The adenoviral vector according to claim 1, wherein the adenoviral vector is a simian adenoviral vector.

3. The adenoviral vector according to claim 1, wherein the adenoviral vector is AdC6 (C6), AdC7 (C7), or AdC9 (C9) vector.

4. An immunogenic composition comprising the adenoviral vector of claim 1 admixed with one or more pharmaceutically acceptable vehicles, carriers, diluents, or adjuvants.

5. A product, combination or kit comprising;
   a) a priming composition comprising the adenoviral vector according to claim 1; and
   b) a boosting composition comprising a recombinant pox virus vector, said pox virus vector further comprising at least one nucleic acid sequence encoding a pathogen or tumour antigen which is the same as the antigen of the priming composition.

6. The product, the combination or the kit according to claim 5, wherein the promoter excludes Exon B of the CMV IE1 gene.

7. A composition comprising the immunogenic composition according to claim 4 and a CpG adjuvant.

* * * * *

SEQUENCE LISTING

<160> NUMBER OF SEQ ID NOS: 12

<210> SEQ ID NO 1
<211> LENGTH: 3039
<212> TYPE: DNA
<213> ORGANISM: Artificial Sequence
<220> FEATURE:
<223> OTHER INFORMATION: Synthetic Sequence

<400> SEQUENCE: 1

```
atgaagatca tcttcttcct gtgctctttc ctgttcttca tcatcaacac ccagtgcgtg      60
acccacgaga gctaccagga gctggtgaag aagctggagg ccctggagga cgccgtgctg     120
accggctaca gcctgttcca gaaagagaag atggtgctga acgagctgtt cgacctgacc     180
aaccacatgc tgaccctgtg cgacaacatc cacggcttca agtacctgat cgacggctac     240
gaggagatca acgagctgct gtacaagctg aacttctact tcgacctgct gcgcgccaag     300
```

```
ctgaacgacg tgtgcgccaa cgactactgc cagatcccct tcaacctgaa gatccgcgcc      360
aacgagctgg acgtgctgaa gaaactggtg ttcggctacc ggaagcccct ggacaacatc      420
aaggacaacg tgggcaagat ggaggactac atcaagaaga caagaccac catcgccaac       480 attaacgagc tgatcgaggg cagcaagaaa accatcgacc agaacaagaa cgccgacaac      540
gaggagggca agaagaagct gtaccaggcc cagtacgacc tgagcatcta caacaagcag      600
ctggaggagg cccacaacct gatcagcgtg ctggagaagc ggatcgacac cctgaagaag      660
aacgagaaca tcaagatcaa ggagatcgcc aagaccatca agttcaacat cgactccctg      720
ttcaccgacc cctggagct ggagtactac ctgcgcgaga agaataagaa gatgcagatc       780
aagaagctga ccctgctgaa ggagcagctg aaagcaagc tgaacagcct gaacaacccc       840
cacaacgtgc tgcagaactt cagcgtgttc ttcaacaaga agaaggaggc cgagatcgcc      900
gaaaccgaga cacccctgga gaataccaag atcctgctga agcactacaa gggcctggtg      960
aagtactaca cggcgagag cagcccctg aaaacctga gcgaagtgag catccagacc        1020
gaggacaact acgccaacct ggagggccaa gtggtcaccg gcgaggccgt gacccccagc      1080
gtgatcgaca catcctgag caagatcgag aacgagtacg aggtgctgta cctgaagccc      1140
ctggccggcg tgtacagaag cctgaagaag cagctggaaa caacgtgat gaccttcaac      1200 gtgaacgtga aggacatcct gaacagccgg ttcaacaagc gggagaactt caagaacgtg      1260
ctggaaagcg acctgatccc ctacaaggac ctgaccagca gcaactacgt ggtgaaggac      1320
ccctacaagt tcctgaacaa agagaagcgg gataagttcc tgagcagcta caactacatc      1380
aaggacagca tcgacaccga catcaacttc gccaacgacg tgctgggcta ctacaagatc      1440
ctgagcgaga agtacaagag cgacctggac agcatcaaga agtacatcaa cgacaagcag      1500
ggcgagaacg agaagtacct gcccttcctg aataacatcg accctgta caagaccgtg      1560 aacgacaaga tcgacctgtt cgtgatccac ctggaagcca aggtgctgaa ctacaccctac      1620 gagaagagca acgtggaggt gaagatcaaa gagctgaact acctgaaaac catccaggac      1680
aagctggccg acttcaagaa gaacaacaac ttcgtcggca tcgccgacct gagcaccgac      1740
tacaaccaca acaacctgct gaccaagttc ctgtccaccg gcatggtgtt cgagaacctg      1800
gccaagacag tgctgtccaa cctgctggac ggcaacctgc agggcggagg gggacccggg      1860
ggaggggacc aagtcgtgac cggcgaagcc atcagcgtga ccatggataa catcctgagc      1920
ggcttcgaaa acgaatacga cgtgatctat ctgaaacccc tggccggcgt gtatcggtct      1980
ctgaagaagc agatcgagaa gaacatcttc accttcaatc tgaacctgaa cgatatcctg      2040
aatagccgcc tgaagaagcg caagtacttc ctggacgtgc tggagagcga cctgatgcag      2100
ttcaagcaca tcagcagcaa cgagtacatc atcgaggaca gcttcaagct gctgaacagc      2160
gagcagaaga acacactgct gaagtcttac aagtatatca aggagagcgt ggagaacgat      2220
atcaagttcg cccaggaggg catcagctac tacgagaaag tgctggccaa gtacaaggac      2280
gatctggagt ccatcaagaa agtgatcaag gaggagaagg agaagttccc cagcagcccc      2340
cccaccaccc cccccagccc cgccaagacc gacgagcaga agaaggagag caagttcctg      2400 cctttttctga ccaatatcga gacactgtat aacaacctgg tgaataagat cgacgactac      2460
ctgatcaatc tgaaggccaa gatcaacgat tgcaacgtgg agaaggacga ggcccacgtg      2520
aagatcacca agctgagcga tctgaaagcc atcgacgata agatcgatct gttcaagaac      2580
ccctacgact tcgaggccat taagaagctg atcaacgacg acaccaagaa ggacatgctg      2640
```

-continued

```
ggcaagctgc tgtctaccgg cctggtgcag aatttcccca acaccatcat cagcaagctg    2700
atcgaaggga agttccagga tatgctgaac atcgcccagc accagtgcgt gaagaagcag    2760
atccccgaga cagcggctg cttccggcac ctggacgagc gcgaggagtg gaagtgcctg     2820
ctgaattaca gcaggaggg cgacaagtgc gtggagaatc ccaacccac ctgcaacgag      2880 aacaacggcg gctgcgacgc cgacgccacc tgcaccgagg aggacagcgg cagcagccgg    2940
aagaagatca cctgcgagtg caccaagccc gacagctacc ccctgttcga cggcatcttc    3000
tgcagcagct ccaacttaat attatattcc tttatctga                           3039
```

<210> SEQ ID NO 2
<211> LENGTH: 1012
<212> TYPE: PRT
<213> ORGANISM: Artificial Sequence
<220> FEATURE:
<223> OTHER INFORMATION: Synthetic Sequence

<400> SEQUENCE: 2

```
Met Lys Ile Ile Phe Phe Leu Cys Ser Phe Leu Phe Ile Ile Asn
  1               5                  10                  15

Thr Gln Cys Val Thr His Glu Ser Tyr Gln Glu Leu Val Lys Lys Leu
             20                  25                  30

Glu Ala Leu Glu Asp Ala Val Leu Thr Gly Tyr Ser Leu Phe Gln Lys
         35                  40                  45

Glu Lys Met Val Leu Asn Glu Leu Phe Asp Leu Thr Asn His Met Leu
     50                  55                  60

Thr Leu Cys Asp Asn Ile His Gly Phe Lys Tyr Leu Ile Asp Gly Tyr
 65                  70                  75                  80

Glu Glu Ile Asn Glu Leu Leu Tyr Lys Leu Asn Phe Tyr Phe Asp Leu
                 85                  90                  95

Leu Arg Ala Lys Leu Asn Asp Val Cys Ala Asn Asp Tyr Cys Gln Ile
            100                 105                 110

Pro Phe Asn Leu Lys Ile Arg Ala Asn Glu Leu Asp Val Leu Lys Lys
        115                 120                 125

Leu Val Phe Gly Tyr Arg Lys Pro Leu Asp Asn Ile Lys Asp Asn Val
    130                 135                 140

Gly Lys Met Glu Asp Tyr Ile Lys Lys Asn Lys Thr Thr Ile Ala Asn
145                 150                 155                 160

Ile Asn Glu Leu Ile Glu Gly Ser Lys Lys Thr Ile Asp Gln Asn Lys
                165                 170                 175

Asn Ala Asp Asn Glu Glu Gly Lys Lys Lys Leu Tyr Gln Ala Gln Tyr
            180                 185                 190

Asp Leu Ser Ile Tyr Asn Lys Gln Leu Glu Glu Ala His Asn Leu Ile
        195                 200                 205

Ser Val Leu Glu Lys Arg Ile Asp Thr Leu Lys Lys Asn Glu Asn Ile
    210                 215                 220

Lys Ile Lys Glu Ile Ala Lys Thr Ile Lys Phe Asn Ile Asp Ser Leu
225                 230                 235                 240

Phe Thr Asp Pro Leu Glu Leu Glu Tyr Tyr Leu Arg Glu Lys Asn Lys
                245                 250                 255

Lys Met Gln Ile Lys Lys Leu Thr Leu Leu Lys Glu Leu Glu Leu Ser
            260                 265                 270

Lys Leu Asn Ser Leu Asn Asn Pro His Asn Val Leu Gln Asn Phe Ser
        275                 280                 285

Val Phe Phe Asn Lys Lys Lys Glu Ala Glu Ile Ala Glu Thr Glu Asn
```

```
              290                 295                 300
Thr Leu Glu Asn Thr Lys Ile Leu Leu Lys His Tyr Lys Gly Leu Val
305                 310                 315                 320

Lys Tyr Tyr Asn Gly Glu Ser Ser Pro Leu Lys Thr Leu Ser Glu Val
                325                 330                 335

Ser Ile Gln Thr Glu Asp Asn Tyr Ala Asn Leu Glu Gly Gln Val Val
                340                 345                 350

Thr Gly Glu Ala Val Thr Pro Ser Val Ile Asp Asn Ile Leu Ser Lys
                355                 360                 365

Ile Glu Asn Glu Tyr Glu Val Leu Tyr Leu Lys Pro Leu Ala Gly Val
                370                 375                 380

Tyr Arg Ser Leu Lys Lys Gln Leu Glu Asn Asn Val Met Thr Phe Asn
385                 390                 395                 400

Val Asn Val Lys Asp Ile Leu Asn Ser Arg Phe Asn Lys Arg Glu Asn
                405                 410                 415

Phe Lys Asn Val Leu Glu Ser Asp Leu Ile Pro Tyr Lys Asp Leu Thr
                420                 425                 430

Ser Ser Asn Tyr Val Val Lys Asp Pro Tyr Lys Phe Leu Asn Lys Glu
                435                 440                 445

Lys Arg Asp Lys Phe Leu Ser Ser Tyr Asn Tyr Ile Lys Asp Ser Ile
450                 455                 460

Asp Thr Asp Ile Asn Phe Ala Asn Asp Val Leu Gly Tyr Tyr Lys Ile
465                 470                 475                 480

Leu Ser Glu Lys Tyr Lys Ser Asp Leu Asp Ser Ile Lys Lys Tyr Ile
                485                 490                 495

Asn Asp Lys Gln Gly Glu Asn Glu Lys Tyr Leu Pro Phe Leu Asn Asn
                500                 505                 510

Ile Glu Thr Leu Tyr Lys Thr Val Asn Asp Lys Ile Asp Leu Phe Val
                515                 520                 525

Ile His Leu Glu Ala Lys Val Leu Asn Tyr Thr Tyr Glu Lys Ser Asn
530                 535                 540

Val Glu Val Lys Ile Lys Glu Leu Asn Tyr Leu Lys Thr Ile Gln Asp
545                 550                 555                 560

Lys Leu Ala Asp Phe Lys Lys Asn Asn Asn Phe Val Gly Ile Ala Asp
                565                 570                 575

Leu Ser Thr Asp Tyr Asn His Asn Asn Leu Leu Thr Lys Phe Leu Ser
                580                 585                 590

Thr Gly Met Val Phe Glu Asn Leu Ala Lys Thr Val Leu Ser Asn Leu
                595                 600                 605

Leu Asp Gly Asn Leu Gln Gly Gly Gly Pro Gly Gly Asp Gln
                610                 615                 620

Val Val Thr Gly Glu Ala Ile Ser Val Thr Met Asp Asn Ile Leu Ser
625                 630                 635                 640

Gly Phe Glu Asn Glu Tyr Asp Val Ile Tyr Leu Lys Pro Leu Ala Gly
                645                 650                 655

Val Tyr Arg Ser Leu Lys Lys Gln Ile Glu Lys Asn Ile Phe Thr Phe
                660                 665                 670

Asn Leu Asn Leu Asn Asp Ile Leu Asn Ser Arg Leu Lys Lys Arg Lys
                675                 680                 685

Tyr Phe Leu Asp Val Leu Glu Ser Asp Leu Met Gln Phe Lys His Ile
                690                 695                 700

Ser Ser Asn Glu Tyr Ile Ile Glu Asp Ser Phe Lys Leu Leu Asn Ser
705                 710                 715                 720
```

Glu Gln Lys Asn Thr Leu Leu Lys Ser Tyr Lys Tyr Ile Lys Glu Ser
                725                 730                 735

Val Glu Asn Asp Ile Lys Phe Ala Gln Glu Gly Ile Ser Tyr Tyr Glu
            740                 745                 750

Lys Val Leu Ala Lys Tyr Lys Asp Asp Leu Glu Ser Ile Lys Lys Val
                755                 760                 765

Ile Lys Glu Glu Lys Glu Lys Phe Pro Ser Ser Pro Pro Thr Thr Pro
770                 775                 780

Pro Ser Pro Ala Lys Thr Asp Glu Gln Lys Lys Glu Ser Lys Phe Leu
785                 790                 795                 800

Pro Phe Leu Thr Asn Ile Glu Thr Leu Tyr Asn Asn Leu Val Asn Lys
                805                 810                 815

Ile Asp Asp Tyr Leu Ile Asn Leu Lys Ala Lys Ile Asn Asp Cys Asn
                820                 825                 830

Val Glu Lys Asp Glu Ala His Val Lys Ile Thr Lys Leu Ser Asp Leu
                835                 840                 845

Lys Ala Ile Asp Asp Lys Ile Asp Leu Phe Lys Asn Pro Tyr Asp Phe
850                 855                 860

Glu Ala Ile Lys Lys Leu Ile Asn Asp Asp Thr Lys Lys Asp Met Leu
865                 870                 875                 880

Gly Lys Leu Leu Ser Thr Gly Leu Val Gln Asn Phe Pro Asn Thr Ile
                885                 890                 895

Ile Ser Lys Leu Ile Glu Gly Lys Phe Gln Asp Met Leu Asn Ile Ala
                900                 905                 910

Gln His Gln Cys Val Lys Lys Gln Ile Pro Glu Asn Ser Gly Cys Phe
                915                 920                 925

Arg His Leu Asp Glu Arg Glu Glu Trp Lys Cys Leu Leu Asn Tyr Lys
                930                 935                 940

Gln Glu Gly Asp Lys Cys Val Glu Asn Pro Asn Pro Thr Cys Asn Glu
945                 950                 955                 960

Asn Asn Gly Gly Cys Asp Ala Asp Ala Thr Cys Thr Glu Glu Asp Ser
                965                 970                 975

Gly Ser Ser Arg Lys Lys Ile Thr Cys Glu Cys Thr Lys Pro Asp Ser
                980                 985                 990

Tyr Pro Leu Phe Asp Gly Ile Phe Cys Ser Ser Ser Asn Leu Ile Leu
                995                 1000                1005

Tyr Ser Phe Ile
    1010

<210> SEQ ID NO 3
<211> LENGTH: 3333
<212> TYPE: DNA
<213> ORGANISM: Artificial Sequence
<220> FEATURE:
<223> OTHER INFORMATION: Synthetic Sequence

<400> SEQUENCE: 3
atgaagatca tcttcttcct gtgctctttc ctgttcttca tcatcaacac ccagtgcgtg     60
acccacgaga gctaccagga gctggtgaag aagctggagg ccctggagga cgccgtgctg    120
accggctaca gcctgttcca gaaagagaag atggtgctga cgagctgtt cgacctgacc    180 aaccacatgc tgaccctgtg cgacaacatc cacggcttca gtacctgat cgacggctac    240 gaggagatca cgagctgct gtacaagctg aacttctact cgacctgct gcgcgccaag    300 ctgaacgacg tgtgcgccaa cgactactgc cagatcccct tcaacctgaa gatccgcgcc    360

```
aacgagctgg acgtgctgaa gaaactggtg ttcggctacc ggaagcccct ggacaacatc    420
aaggacaacg tgggcaagat ggaggactac atcaagaaga caagaccac catcgccaac     480 attaacgagc tgatcgaggg cagcaagaaa accatcgacc agaacaagaa cgccgacaac    540
gaggagggca gaagaagct gtaccaggcc cagtacgacc tgagcatcta caacaagcag     600
ctggaggagg cccacaacct gatcagcgtg ctggagaagc ggatcgacac cctgaagaag    660
aacgagaaca tcaagatcaa ggagatcgcc aagaccatca agttcaacat cgactccctg    720
ttcaccgacc ccctggagct ggagtactac ctgcgcgaga agaataagaa gatgcagatc    780
aagaagctga ccctgctgaa ggagcagctg aaaagcaagc tgaacagcct gaacaacccc    840
cacaacgtgc tgcagaactt cagcgtgttc ttcaacaaga agaaggaggc cgagatcgcc    900
gaaaccgaga cacccctgga aataccaag atcctgctga agcactacaa gggcctggtg     960
aagtactaca acggcgagag cagccccctg aaaaccctga gcgaagtgag catccagacc    1020
gaggacaact acgccaacct ggagggccaa gtggtcaccg cgaggccgt gaccccccagc    1080 gtgatcgaca acatcctgag caagatcgag aacgagtacg aggtgctgta cctgaagccc    1140
ctggccggcg tgtacagaag cctgaagaag cagctggaaa caacgtgat gaccttcaac    1200 gtgaacgtga aggacatcct gaacagccgg ttcaacaagc gggagaactt caagaacgtg    1260
ctggaaagcg acctgatccc ctacaaggac ctgaccagca gcaactacgt ggtgaaggac    1320
ccctacaagt tcctgaacaa agagaagcgg gataagttcc tgagcagcta caactacatc    1380
aaggacagca tcgacaccga catcaacttc gccaacgacg tgctgggcta ctacaagatc    1440
ctgagcgaga agtacaagag cgacctggac agcatcaaga agtacatcaa cgacaagcag    1500
ggcgagaacg agaagtacct gcccttcctg aataacatcg agaccctgta caagaccgtg    1560
aacgacaaga tcgacctgtt cgtgatccac ctggaagcca aggtgctgaa ctacacctac    1620
gagaagagca acgtggaggt gaagatcaaa gagctgaact acctgaaaac catccaggac    1680
aagctggccg acttcaagaa gaacaacaac ttcgtcggca tcgccgacct gagcaccgac    1740
tacaaccaca caaccctgct gaccaagttc ctgtccaccg catggtgtt cgagaacctg    1800 gccaagacag tgctgtccaa cctgctggac ggcaacctgc agggcatgct caatatcgca    1860
cagcatcagt gtgtcaaaaa acagattcct cagaactccg gctgctttag acacctggat    1920
gaacgggaag aatggaagtg tctgctcaac tataaacagg aaggtgataa gtgtgtcgag    1980 aacccctaacc ctacctgtaa tgagaataat ggggctgtg atgccgatgc caaatgtacc    2040
gaagaagatt ccggctccaa tggcaagaaa atcacatgtg aatgtaccaa acccgactcc    2100
taccctctct tcgatgggat cttttgcagc tccagtaatg gcggcggacc cggggaggg    2160 gaccaagtcg tgaccggcga agccatcagc gtgaccatgg ataacatcct gagcggcttc    2220
gaaaacgaat acgacgtgat ctatctgaaa ccctggccg gcgtgtatcg gtctctgaag    2280
aagcagatcg agaagaacat cttccacttc aatctgaacc tgaacgatat cctgaatagc    2340
cgcctgaaga gcgcaagta cttcctggac gtgctggaga gcgacctgat gcagttcaag    2400
cacatcagca gcaacgagta catcatcgag gacagcttca gctgctgaa cagcgagcag    2460 aagaacacac tgctgaagtc ttacaagtat atcaaggaga gcgtggagaa cgatatcaag    2520
ttcgcccagg agggcatcag ctactacgag aaagtgctgg ccaagtacaa ggacgatctg    2580
gagtccatca gaaagtgat caaggaggag aaggagaagt cccccagcag ccccccacc    2640 accccccccca gccccgccaa gaccgacgag cagaagaagg agagcaagtt cctgccttt    2700
```

```
ctgaccaata tcgagacact gtataacaac ctggtgaata agatcgacga ctacctgatc    2760
aatctgaagg ccaagatcaa cgattgcaac gtggagaagg acgaggccca cgtgaagatc    2820
accaagctga gcgatctgaa agccatcgac gataagatcg atctgttcaa gaaccctac     2880 gacttcgagg ccattaagaa gctgatcaac gacgacacca gaaggacat gctgggcaag     2940 ctgctgtcta ccggcctggt gcagaatttc cccaacacca tcatcagcaa gctgatcgaa    3000
gggaagttcc aggatatgct gaacatcgcc cagcaccagt gcgtgaagaa gcagatcccc    3060
gagaacagcg gctgcttccg gcacctggac gagcgcgagg agtggaagtg cctgctgaat    3120
tacaagcagg agggcgacaa gtgcgtggag aatcccaacc ccacctgcaa cgagaacaac    3180
ggcggctgcg acgccgacgc cacctgcacc gaggaggaca cggcagcag ccggaagaag     3240 atcacctgcg agtgcaccaa gcccgacagc taccccctgt cgacggcat cttctgcagc     3300 agctccaact aatatattata ttcctttatc tga                                3333
```

<210> SEQ ID NO 4
<211> LENGTH: 1110
<212> TYPE: PRT
<213> ORGANISM: Artificial Sequence
<220> FEATURE:
<223> OTHER INFORMATION: Synthetic Sequence

<400> SEQUENCE: 4

```
Met Lys Ile Ile Phe Phe Leu Cys Ser Phe Leu Phe Phe Ile Ile Asn
 1               5                  10                  15

Thr Gln Cys Val Thr His Glu Ser Tyr Gln Glu Leu Val Lys Lys Leu
            20                  25                  30

Glu Ala Leu Glu Asp Ala Val Leu Thr Gly Tyr Ser Leu Phe Gln Lys
        35                  40                  45

Glu Lys Met Val Leu Asn Glu Leu Phe Asp Leu Thr Asn His Met Leu
    50                  55                  60

Thr Leu Cys Asp Asn Ile His Gly Phe Lys Tyr Leu Ile Asp Gly Tyr
65                  70                  75                  80

Glu Glu Ile Asn Glu Leu Leu Tyr Lys Leu Asn Phe Tyr Phe Asp Leu
                85                  90                  95

Leu Arg Ala Lys Leu Asn Asp Val Cys Ala Asn Asp Tyr Cys Gln Ile
            100                 105                 110

Pro Phe Asn Leu Lys Ile Arg Ala Asn Glu Leu Asp Val Leu Lys Lys
        115                 120                 125

Leu Val Phe Gly Tyr Arg Lys Pro Leu Asp Asn Ile Lys Asp Asn Val
    130                 135                 140

Gly Lys Met Glu Asp Tyr Ile Lys Lys Asn Lys Thr Thr Ile Ala Asn
145                 150                 155                 160

Ile Asn Glu Leu Ile Glu Gly Ser Lys Lys Thr Ile Asp Gln Asn Lys
                165                 170                 175

Asn Ala Asp Asn Glu Glu Gly Lys Lys Lys Leu Tyr Gln Ala Gln Tyr
            180                 185                 190

Asp Leu Ser Ile Tyr Asn Lys Gln Leu Glu Glu Ala His Asn Leu Ile
        195                 200                 205

Ser Val Leu Glu Lys Arg Ile Asp Thr Leu Lys Lys Asn Glu Asn Ile
    210                 215                 220

Lys Ile Lys Glu Ile Ala Lys Thr Ile Lys Phe Asn Ile Asp Ser Leu
225                 230                 235                 240

Phe Thr Asp Pro Leu Glu Leu Glu Tyr Tyr Leu Arg Glu Lys Asn Lys
                245                 250                 255
```

```
Lys Met Gln Ile Lys Lys Leu Thr Leu Leu Lys Glu Gln Leu Glu Ser
            260             265             270
Lys Leu Asn Ser Leu Asn Asn Pro His Asn Val Leu Gln Asn Phe Ser
            275             280             285
Val Phe Phe Asn Lys Lys Lys Glu Ala Glu Ile Ala Glu Thr Glu Asn
290             295             300
Thr Leu Glu Asn Thr Lys Ile Leu Leu Lys His Tyr Lys Gly Leu Val
305             310             315             320
Lys Tyr Tyr Asn Gly Glu Ser Ser Pro Leu Lys Thr Leu Ser Glu Val
                325             330             335
Ser Ile Gln Thr Glu Asp Asn Tyr Ala Asn Leu Glu Gly Gln Val Val
            340             345             350
Thr Gly Glu Ala Val Thr Pro Ser Val Ile Asp Asn Ile Leu Ser Lys
            355             360             365
Ile Glu Asn Glu Tyr Glu Val Leu Tyr Leu Lys Pro Leu Ala Gly Val
            370             375             380
Tyr Arg Ser Leu Lys Lys Gln Leu Glu Asn Asn Val Met Thr Phe Asn
385             390             395             400
Val Asn Val Lys Asp Ile Leu Asn Ser Arg Phe Asn Lys Arg Glu Asn
                405             410             415
Phe Lys Asn Val Leu Glu Ser Asp Leu Ile Pro Tyr Lys Asp Leu Thr
            420             425             430
Ser Ser Asn Tyr Val Val Lys Asp Pro Tyr Lys Phe Leu Asn Lys Glu
            435             440             445
Lys Arg Asp Lys Phe Leu Ser Ser Tyr Asn Tyr Ile Lys Asp Ser Ile
450             455             460
Asp Thr Asp Ile Asn Phe Ala Asn Asp Val Leu Gly Tyr Tyr Lys Ile
465             470             475             480
Leu Ser Glu Lys Tyr Lys Ser Asp Leu Asp Ser Ile Lys Lys Tyr Ile
            485             490             495
Asn Asp Lys Gln Gly Glu Asn Glu Lys Tyr Leu Pro Phe Leu Asn Asn
            500             505             510
Ile Glu Thr Leu Tyr Lys Thr Val Asn Asp Lys Ile Asp Leu Phe Val
            515             520             525
Ile His Leu Glu Ala Lys Val Leu Asn Tyr Thr Tyr Glu Lys Ser Asn
            530             535             540
Val Glu Val Lys Ile Lys Glu Leu Asn Tyr Leu Lys Thr Ile Gln Asp
545             550             555             560
Lys Leu Ala Asp Phe Lys Lys Asn Asn Phe Val Gly Ile Ala Asp
                565             570             575
Leu Ser Thr Asp Tyr Asn His Asn Asn Leu Leu Thr Lys Phe Leu Ser
            580             585             590
Thr Gly Met Val Phe Glu Asn Leu Ala Lys Thr Val Leu Ser Asn Leu
            595             600             605
Leu Asp Gly Asn Leu Gln Gly Met Leu Asn Ile Ala Gln His Gln Cys
            610             615             620
Val Lys Lys Gln Ile Pro Gln Asn Ser Gly Cys Phe Arg His Leu Asp
625             630             635             640
Glu Arg Glu Glu Trp Lys Cys Leu Leu Asn Tyr Lys Gln Glu Gly Asp
                645             650             655
Lys Cys Val Glu Asn Pro Asn Pro Thr Cys Asn Glu Asn Asn Gly Gly
            660             665             670
```

```
Cys Asp Ala Asp Ala Lys Cys Thr Glu Glu Asp Ser Gly Ser Asn Gly
            675                 680                 685

Lys Lys Ile Thr Cys Glu Cys Thr Lys Pro Asp Ser Tyr Pro Leu Phe
        690                 695                 700

Asp Gly Ile Phe Cys Ser Ser Ser Asn Gly Gly Pro Gly Gly Gly
705                 710                 715                 720

Asp Gln Val Val Thr Gly Glu Ala Ile Ser Val Thr Met Asp Asn Ile
                725                 730                 735

Leu Ser Gly Phe Glu Asn Glu Tyr Asp Val Ile Tyr Leu Lys Pro Leu
            740                 745                 750

Ala Gly Val Tyr Arg Ser Leu Lys Lys Gln Ile Glu Lys Asn Ile Phe
        755                 760                 765

Thr Phe Asn Leu Asn Leu Asn Asp Ile Leu Asn Ser Arg Leu Lys Lys
    770                 775                 780

Arg Lys Tyr Phe Leu Asp Val Leu Glu Ser Asp Leu Met Gln Phe Lys
785                 790                 795                 800

His Ile Ser Ser Asn Glu Tyr Ile Ile Glu Asp Ser Phe Lys Leu Leu
                805                 810                 815

Asn Ser Glu Gln Lys Asn Thr Leu Leu Lys Ser Tyr Lys Tyr Ile Lys
            820                 825                 830

Glu Ser Val Glu Asn Asp Ile Lys Phe Ala Gln Glu Gly Ile Ser Tyr
        835                 840                 845

Tyr Glu Lys Val Leu Ala Lys Tyr Lys Asp Asp Leu Glu Ser Ile Lys
    850                 855                 860

Lys Val Ile Lys Glu Glu Lys Glu Lys Phe Pro Ser Ser Pro Pro Thr
865                 870                 875                 880

Thr Pro Pro Ser Pro Ala Lys Thr Asp Glu Gln Lys Lys Glu Ser Lys
                885                 890                 895

Phe Leu Pro Phe Leu Thr Asn Ile Glu Thr Leu Tyr Asn Asn Leu Val
            900                 905                 910

Asn Lys Ile Asp Asp Tyr Leu Ile Asn Leu Lys Ala Lys Ile Asn Asp
        915                 920                 925

Cys Asn Val Glu Lys Asp Glu Ala His Val Lys Ile Thr Lys Leu Ser
    930                 935                 940

Asp Leu Lys Ala Ile Asp Asp Lys Ile Asp Leu Phe Lys Asn Pro Tyr
945                 950                 955                 960

Asp Phe Glu Ala Ile Lys Lys Leu Ile Asn Asp Thr Lys Lys Asp
                965                 970                 975

Met Leu Gly Lys Leu Leu Ser Thr Gly Leu Val Gln Asn Phe Pro Asn
            980                 985                 990

Thr Ile Ile Ser Lys Leu Ile Glu Gly Lys Phe Gln Asp Met Leu Asn
        995                 1000                1005

Ile Ala Gln His Gln Cys Val Lys Lys Gln Ile Pro Glu Asn Ser Gly
    1010                1015                1020

Cys Phe Arg His Leu Asp Glu Arg Glu Glu Trp Lys Cys Leu Leu Asn
1025                1030                1035                1040

Tyr Lys Gln Glu Gly Asp Lys Cys Val Glu Asn Pro Asn Pro Thr Cys
                1045                1050                1055

Asn Glu Asn Asn Gly Gly Cys Asp Ala Asp Ala Thr Cys Thr Glu Glu
            1060                1065                1070

Asp Ser Gly Ser Ser Arg Lys Lys Ile Thr Cys Glu Cys Thr Lys Pro
        1075                1080                1085

Asp Ser Tyr Pro Leu Phe Asp Gly Ile Phe Cys Ser Ser Ser Asn Leu
```

Ile Leu Tyr Ser Phe Ile
1105            1110

<210> SEQ ID NO 5
<211> LENGTH: 3093
<212> TYPE: DNA
<213> ORGANISM: Artificial Sequence
<220> FEATURE:
<223> OTHER INFORMATION: Synthetic Sequence

<400> SEQUENCE: 5

```
atgaagatca tcttcttcct gtgctctttc ctgttcttca tcatcaacac ccagtgcgtg      60
acccacgaga gctaccagga gctggtgaag aagctggagg ccctgaggga cgccgtgctg     120
accggctaca gcctgttcca gaaagagaag atggtgctga cgagctgtt cgacctgacc      180
aaccacatgc tgaccctgtg cgacaacatc cacggcttca gtacctgat cgacggctac      240
gaggagatca cgagctgct gtacaagctg aacttctact cgacctgct gcgcgccaag      300
ctgaacgacg tgtgcgccaa cgactactgc cagatcccct tcaacctgaa gatccgcgcc     360
aacgagctgg acgtgctgaa gaaactggtg ttcggctacc ggaagcccct ggacaacatc     420
aaggacaacg tgggcaagat ggaggactac atcaagaaga caagaccac catcgccaac     480
attaacgagc tgatcgaggg cagcaagaaa ccatcgacc agaacaagaa cgccgacaac     540
gaggagggca agaagaagct gtaccaggcc cagtacgacc tgagcatcta caacaagcag     600
ctggaggagg cccacaacct gatcagcgtg ctggagaagc ggatcgacac cctgaagaag     660
aacgagaaca tcaagatcaa ggagatcgcc aagaccatca gttcaacat cgactccctg      720
ttcaccgacc ccctggagct ggagtactac ctgcgcgaga agaataagaa gatgcagatc     780
aagaagctga cccctgctgaa ggagcagctg gaaagcaagc tgaacagcct gaacaacccc     840
cacaacgtgc tgcagaactt cagcgtgttc ttcaacaaga gaaggaggc cgagatcgcc     900
gaaaccgaga caccctggga aataccaag atcctgctga gcactacaa gggcctggtg      960
aagtactaca cggcgagag cagccccctg aaaaccctga gcaagtgag catccagacc      1020
gaggacaact acgccaacct ggagggccaa gtggtcaccg cgaggccgt gaccacaagc    1080
gtgatcgaca atatcctgag caagatcgag aacgagtacg aagtgctgta cctgaagcct    1140
ctggccggcg tgtaccggag cctgaagaaa cagctggaga caacgtgat gaccttcaac    1200
gtgaacgtga aggacatcct gaacagccgg ttcaacaagc gcgagaactt caagaacgtg    1260
ctggagtccg acctgatccc ctacaaggac ctgaccagca gcaactacgt ggtgaaggac    1320
ccctacaagt tcctgaacaa ggagaagcgc gacaagtttc tgtccagcta caactacatt    1380
aaggacagca tcgacaccga catcaacttc gccaacgacg tgctgggcta ctacaagatc    1440
ctgagcgaga agtacaagag cgacctggat agcatcaaga agtacatcaa cgacaagcag    1500
ggcgagaacg agaagtacct gcccttcctg aataacatcg agaccctgta caagaccgtg    1560
aacgacaaga tcgacctgtt cgtgatccac ctggaggcca agtgctgaa ctacacctac    1620
gagaagagca cgtggaagt gaagattaag gagctgaact acctgaaaac catccaggac    1680
aagctggccg acttcaagaa gaataacaac ttcgtgggca tcgccgatct gagcaccgac    1740
tacaaccaca caacctgct gaccaagttc ctgtccaccg gcatggtgtt cgagaacctg    1800
ctgaagagcg tgctgagcaa cctgctggac tggaagctgg cccgctacgt gaagcacttc    1860
accacccca tgcggaaaaa gaccatgatc cagcagagcg aggggggacc cggggagggg    1920
```

-continued

```
gaccaagtcg tgaccggcga agccatcagc gtgaccatgg ataacatcct gagcggcttc    1980
gaaaacgaat acgacgtgat ctatctgaaa cccctggccg gcgtgtatcg gtctctgaag    2040
aagcagatcg agaagaacat cttcaccttc aatctgaacc tgaacgatat cctgaatagc    2100
cgcctgaaga gcgcaagta  cttcctggac gtgctggaga gcgacctgat gcagttcaag    2160
cacatcagca gcaacgagta catcatcgag gacagcttca agctgctgaa cagcgagcag    2220
aagaacacac tgctgaagtc ttacaagtat atcaaggaga gcgtggagaa cgatatcaag    2280
ttcgcccagg agggcatcag ctactacgag aaagtgctgg ccaagtacaa ggacgatctg    2340
gagtccatca agaaagtgat caaggaggag aaggagaagt ccccagcag  cccccccacc    2400 accccccca  gccccgccaa gaccgacgag cagaagaagg agagcaagtt cctgcctttt    2460
ctgaccaata tcgagacact gtataacaac ctggtgaata agatcgacga ctacctgatc    2520
aatctgaagg ccaagatcaa cgattgcaac gtggagaagg acgaggccca cgtgaagatc    2580
accaagctga gcgatctgaa agccatcgac gataagatcg atctgttcaa gaaccccctac   2640 gacttcgagg ccattaagaa gctgatcaac gacgacacca gaaggacat  gctgggcaag    2700 ctgctgtcta ccggcctggt gcagaatttc cccaacacca tcatcagcaa gctgatcgaa    2760
gggaagttcc aggatatgct gaacatcgcc cagcaccagt gcgtgaagaa gcagatcccc    2820
gagaacagcg gctgcttccg gcacctggac gagcgcgagg agtggaagtg cctgctgaat    2880
tacaagcagg agggcgacaa gtgcgtggag aatcccaacc ccacctgcaa cgagaacaac    2940
ggcggctgcg acgccgacgc cacctgcacc gaggaggaca gcggcagcag ccggaagaag    3000
atcacctgcg agtgcaccaa gcccgacagc taccccctgt tcgacggcat cttctgcagc    3060
agctccaact taatattata ttcctttatc tga                                 3093
```

<210> SEQ ID NO 6
<211> LENGTH: 1030
<212> TYPE: PRT
<213> ORGANISM: Artificial Sequence
<220> FEATURE:
<223> OTHER INFORMATION: Synthetic Sequence

<400> SEQUENCE: 6

```
Met Lys Ile Ile Phe Phe Leu Cys Ser Phe Leu Phe Phe Ile Ile Asn
1               5                   10                  15

Thr Gln Cys Val Thr His Glu Ser Tyr Gln Glu Leu Val Lys Lys Leu
            20                  25                  30

Glu Ala Leu Glu Asp Ala Val Leu Thr Gly Tyr Ser Leu Phe Gln Lys
        35                  40                  45

Glu Lys Met Val Leu Asn Glu Leu Phe Asp Leu Thr Asn His Met Leu
    50                  55                  60

Thr Leu Cys Asp Asn Ile His Gly Phe Lys Tyr Leu Ile Asp Gly Tyr
65                  70                  75                  80

Glu Glu Ile Asn Glu Leu Leu Tyr Lys Leu Asn Phe Tyr Phe Asp Leu
                85                  90                  95

Leu Arg Ala Lys Leu Asn Asp Val Cys Ala Asn Asp Tyr Cys Gln Ile
            100                 105                 110

Pro Phe Asn Leu Lys Ile Arg Ala Asn Glu Leu Asp Val Leu Lys Lys
        115                 120                 125

Leu Val Phe Gly Tyr Arg Lys Pro Leu Asp Asn Ile Lys Asp Asn Val
    130                 135                 140

Gly Lys Met Glu Asp Tyr Ile Lys Lys Asn Lys Thr Thr Ile Ala Asn
145                 150                 155                 160
```

Ile Asn Glu Leu Ile Glu Gly Ser Lys Lys Thr Ile Asp Gln Asn Lys
                165                 170                 175

Asn Ala Asp Asn Glu Glu Gly Lys Lys Lys Leu Tyr Gln Ala Gln Tyr
            180                 185                 190

Asp Leu Ser Ile Tyr Asn Lys Gln Leu Glu Glu Ala His Asn Leu Ile
        195                 200                 205

Ser Val Leu Glu Lys Arg Ile Asp Thr Leu Lys Lys Asn Glu Asn Ile
    210                 215                 220

Lys Ile Lys Glu Ile Ala Lys Thr Ile Lys Phe Asn Ile Asp Ser Leu
225                 230                 235                 240

Phe Thr Asp Pro Leu Glu Leu Glu Tyr Tyr Leu Arg Glu Lys Asn Lys
                245                 250                 255

Lys Met Gln Ile Lys Lys Leu Thr Leu Leu Lys Glu Gln Leu Glu Ser
            260                 265                 270

Lys Leu Asn Ser Leu Asn Asn Pro His Asn Val Leu Gln Asn Phe Ser
        275                 280                 285

Val Phe Phe Asn Lys Lys Lys Glu Ala Glu Ile Ala Glu Thr Glu Asn
    290                 295                 300

Thr Leu Glu Asn Thr Lys Ile Leu Leu Lys His Tyr Lys Gly Leu Val
305                 310                 315                 320

Lys Tyr Tyr Asn Gly Glu Ser Ser Pro Leu Lys Thr Leu Ser Glu Val
                325                 330                 335

Ser Ile Gln Thr Glu Asp Asn Tyr Ala Asn Leu Glu Gly Gln Val Val
            340                 345                 350

Thr Gly Glu Ala Val Thr Thr Ser Val Ile Asp Asn Ile Leu Ser Lys
        355                 360                 365

Ile Glu Asn Glu Tyr Glu Val Leu Tyr Leu Lys Pro Leu Ala Gly Val
    370                 375                 380

Tyr Arg Ser Leu Lys Lys Gln Leu Glu Asn Asn Val Met Thr Phe Asn
385                 390                 395                 400

Val Asn Val Lys Asp Ile Leu Asn Ser Arg Phe Asn Lys Arg Glu Asn
                405                 410                 415

Phe Lys Asn Val Leu Glu Ser Asp Leu Ile Pro Tyr Lys Asp Leu Thr
            420                 425                 430

Ser Ser Asn Tyr Val Val Lys Asp Pro Tyr Lys Phe Leu Asn Lys Glu
        435                 440                 445

Lys Arg Asp Lys Phe Leu Ser Ser Tyr Asn Tyr Ile Lys Asp Ser Ile
    450                 455                 460

Asp Thr Asp Ile Asn Phe Ala Asn Asp Val Leu Gly Tyr Tyr Lys Ile
465                 470                 475                 480

Leu Ser Glu Lys Tyr Lys Ser Asp Leu Asp Ser Ile Lys Lys Tyr Ile
                485                 490                 495

Asn Asp Lys Gln Gly Glu Asn Glu Lys Tyr Leu Pro Phe Leu Asn Asn
            500                 505                 510

Ile Glu Thr Leu Tyr Lys Thr Val Asn Asp Lys Ile Asp Leu Phe Val
        515                 520                 525

Ile His Leu Glu Ala Lys Val Leu Asn Tyr Thr Tyr Glu Lys Ser Asn
    530                 535                 540

Val Glu Val Lys Ile Lys Glu Leu Asn Tyr Leu Lys Thr Ile Gln Asp
545                 550                 555                 560

Lys Leu Ala Asp Phe Lys Lys Asn Asn Asn Phe Val Gly Ile Ala Asp
                565                 570                 575

Leu Ser Thr Asp Tyr Asn His Asn Asn Leu Leu Thr Lys Phe Leu Ser
            580                 585                 590

Thr Gly Met Val Phe Glu Asn Leu Leu Lys Ser Val Leu Ser Asn Leu
        595                 600                 605

Leu Asp Trp Lys Leu Ala Arg Tyr Val Lys His Phe Thr Thr Pro Met
    610                 615                 620

Arg Lys Lys Thr Met Ile Gln Gln Ser Gly Gly Pro Gly Gly Gly
625                 630                 635                 640

Asp Gln Val Val Thr Gly Glu Ala Ile Ser Val Thr Met Asp Asn Ile
                645                 650                 655

Leu Ser Gly Phe Glu Asn Glu Tyr Asp Val Ile Tyr Leu Lys Pro Leu
            660                 665                 670

Ala Gly Val Tyr Arg Ser Leu Lys Lys Gln Ile Glu Lys Asn Ile Phe
        675                 680                 685

Thr Phe Asn Leu Asn Leu Asn Asp Ile Leu Asn Ser Arg Leu Lys Lys
    690                 695                 700

Arg Lys Tyr Phe Leu Asp Val Leu Glu Ser Asp Leu Met Gln Phe Lys
705                 710                 715                 720

His Ile Ser Ser Asn Glu Tyr Ile Ile Glu Asp Ser Phe Lys Leu Leu
                725                 730                 735

Asn Ser Glu Gln Lys Asn Thr Leu Leu Lys Ser Tyr Lys Tyr Ile Lys
            740                 745                 750

Glu Ser Val Glu Asn Asp Ile Lys Phe Ala Gln Glu Gly Ile Ser Tyr
        755                 760                 765

Tyr Glu Lys Val Leu Ala Lys Tyr Lys Asp Asp Leu Glu Ser Ile Lys
    770                 775                 780

Lys Val Ile Lys Glu Glu Lys Glu Lys Phe Pro Ser Ser Pro Pro Thr
785                 790                 795                 800

Thr Pro Pro Ser Pro Ala Lys Thr Asp Glu Gln Lys Lys Glu Ser Lys
                805                 810                 815

Phe Leu Pro Phe Leu Thr Asn Ile Glu Thr Leu Tyr Asn Asn Leu Val
            820                 825                 830

Asn Lys Ile Asp Asp Tyr Leu Ile Asn Leu Lys Ala Lys Ile Asn Asp
        835                 840                 845

Cys Asn Val Glu Lys Asp Glu Ala His Val Lys Ile Thr Lys Leu Ser
850                 855                 860

Asp Leu Lys Ala Ile Asp Asp Lys Ile Asp Leu Phe Lys Asn Pro Tyr
865                 870                 875                 880

Asp Phe Glu Ala Ile Lys Lys Leu Ile Asn Asp Asp Thr Lys Lys Asp
                885                 890                 895

Met Leu Gly Lys Leu Leu Ser Thr Gly Leu Val Gln Asn Phe Pro Asn
            900                 905                 910

Thr Ile Ile Ser Lys Leu Ile Glu Gly Lys Phe Gln Asp Met Leu Asn
        915                 920                 925

Ile Ala Gln His Gln Cys Val Lys Lys Gln Ile Pro Glu Asn Ser Gly
    930                 935                 940

Cys Phe Arg His Leu Asp Glu Arg Glu Glu Trp Lys Cys Leu Leu Asn
945                 950                 955                 960

Tyr Lys Gln Glu Gly Asp Lys Cys Val Glu Asn Pro Asn Pro Thr Cys
                965                 970                 975

Asn Glu Asn Asn Gly Gly Cys Asp Ala Asp Ala Thr Cys Thr Glu Glu
            980                 985                 990

Asp Ser Gly Ser Ser Arg Lys Lys Ile Thr Cys Glu Cys Thr Lys Pro

```
                995               1000              1005
Asp Ser Tyr Pro Leu Phe Asp Gly Ile Phe Cys Ser Ser Ser Asn Leu
    1010              1015              1020

Ile Leu Tyr Ser Phe Ile
1025            1030

<210> SEQ ID NO 7
<211> LENGTH: 1947
<212> TYPE: DNA
<213> ORGANISM: Artificial Sequence
<220> FEATURE:
<223> OTHER INFORMATION: Synthetic Sequence

<400> SEQUENCE: 7
tgtgagtttc tgtgtaactg atatcgccat ttttccaaaa gtgattttg ggcatacgcg      60 atatctggcg atagcgctta tatcgtttac gggggatggc gatagacgac tttggtgact     120
tgggcgattc tgtgtgtcgc aaatatcgca gtttcgatat aggtgacaga cgatatgagg     180
ctatatcgcc gatagaggcg acatcaagct ggcacatggc caatgcatat cgatctatac     240
attgaatcaa tattggccat tagccatatt attcattggt tatatagcat aaatcaatat     300
tggctattgg ccattgcata cgttgtatcc atatcataat atgtacattt atattggctc     360
atgtccaaca ttaccgccat gttgacattg attattgact agttattaat agtaatcaat     420
tacggggtca ttagttcata gcccatatat ggagttccgc gttacataac ttacggtaaa     480
tggcccgcct ggctgaccgc ccaacgaccc cgcccattg acgtcaataa tgacgtatgt      540
tcccatagta acgccaatag ggactttcca ttgacgtcaa tgggtggagt atttacggta     600
aactgcccac ttggcagtac atcaagtgta tcatatgcca gtacgcccc ctattgacgt      660 caatgacggt aaatggcccg cctggcatta tgcccagtac atgaccttat gggactttcc     720
tacttggcag tacatctacg tattagtcat cgctattacc atggtgatgc ggttttggca     780
gtacatcaat gggcgtggat agcggtttga ctcacgggga tttccaagtc tccaccccat     840
tgacgtcaat gggagtttgt tttggcacca aaatcaacgg gactttccaa aatgtcgtaa     900
caactccgcc ccattgacgc aaatgggcgg taggcgtgta cggtgggagg tctatataag     960
cagagctcgt ttagtgaacc gtcagatcgc ctggagacgc catccacgct gttttgacct    1020
ccatagaaga caccgggacc gatccagcct ccgcggccgg aacggtgca ttggaacgcg    1080 gattccccgt gccaagagtg acgtaagtac cgcctataga gtctataggc ccacccccctt    1140 ggcttcttat gcatgctata ctgttttggg cttgggtct atacaccccc gcttcctcat    1200
gttataggtg atggtatagc ttagcctata ggtgtgggtt attgaccatt attgaccact    1260
cccctattgg tgacgatact ttccattact aatccataac atggctcttt gccacaactc    1320
tctttattgg ctatatgcca atacactgtc cttcagagac tgacacggac tctgtatttt    1380
tacaggatgg ggtctcattt attatttaca aattcacata caacacca ccgtccccag      1440 tgcccgcagt ttttattaaa cataacgtgg gatctccacg cgaatctcgg gtacgtgttc    1500
cggacatggg ctcttctccg gtagcggcgg agcttctaca tccgagccct gctcccatgc    1560
ctccagcgac tcatggtcgc tcggcagctc cttgctccta acagtggagg ccagacttag    1620
gcacagcacg atgcccacca ccaccagtgt gccgcacaag gccgtggcgg tagggtatgt     1680
gtctgaaaat gagctcgggg agcgggcttg caccgctgac gcatttggaa gacttaaggc    1740
agcggcagaa gaagatgcag gcagctgagt tgttgtgttc tgataagagt cagaggtaac    1800
tcccgttgcg gtgctgttaa cggtggaggg cagtgtagtc tgagcagtac tcgttgctgc    1860
```

```
cgcgcgcgcc accagacata atagctgaca gactaacaga ctgttccttt ccatgggtct    1920
tttctgcagt caccgtcctt gacacga                                        1947

<210> SEQ ID NO 8
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 8

Ile Pro Asn Pro Leu Leu Gly Leu Asp
1               5

<210> SEQ ID NO 9
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 9

Ile His Leu Tyr Val Asn Val Phe Ser Asn Asn Ala Lys Glu Ile
1               5                   10                  15

<210> SEQ ID NO 10
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 10

Asn Val Ala Phe Asn Arg Phe Leu Val
1               5

<210> SEQ ID NO 11
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 11

Asp Ala Ser Lys Asn Lys Glu Lys Ala Leu
1               5                   10

<210> SEQ ID NO 12
<211> LENGTH: 9
<212> TYPE: PRT
<213> ORGANISM: Artificial Sequence
<220> FEATURE:
<223> OTHER INFORMATION: epitope Pb9

<400> SEQUENCE: 12

Ser Tyr Ile Pro Ser Ala Glu Lys Ile
1               5
```